US012604659B2

(12) United States Patent
Moon et al.

(10) Patent No.: US 12,604,659 B2
(45) Date of Patent: Apr. 14, 2026

(54) ORGANIC ELECTROLUMINESCENT COMPOUND AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Doo-Hyeon Moon, Gyeonggi-do (KR); Hyo-Nim Shin, Gyeonggi-do (KR); Hong-Se Oh, Gyeonggi-do (KR); Dong-Hyung Lee, Gyeonggi-do (KR); So-Mi Park, Gyeonggi-do (KR); Du-Yong Park, Gyeonggi-do (KR)

(73) Assignee: Dupont Specialty Materials Korea Ltd. (KR)

( * ) Notice: Subject to any disclaimer, the term of this patent is extended or adjusted under 35 U.S.C. 154(b) by 431 days.

(21) Appl. No.: 18/184,868

(22) Filed: Mar. 16, 2023

(65) Prior Publication Data

US 2023/0225197 A1 Jul. 13, 2023

Related U.S. Application Data

(63) Continuation of application No. 17/322,420, filed on May 17, 2021, now abandoned.

(30) Foreign Application Priority Data

May 20, 2020 (KR) ........................ 10-2020-0060388

(51) Int. Cl.

| | |
|---|---|
| ***H10K 85/60*** | (2023.01) |
| ***C07C 211/61*** | (2006.01) |
| ***C09K 11/06*** | (2006.01) |
| ***H10K 50/16*** | (2023.01) |
| *H10K 50/15* | (2023.01) |

(52) U.S. Cl.

CPC .......... *H10K 85/633* (2023.02); *C07C 211/61* (2013.01); *C09K 11/06* (2013.01); *H10K 50/16* (2023.02); *H10K 85/621* (2023.02); *H10K 85/631* (2023.02); *H10K 85/636* (2023.02); *H10K 85/6572* (2023.02); *H10K 85/6574* (2023.02); *H10K 85/6576* (2023.02); *C07C 2603/18* (2017.05); *C07C 2603/26* (2017.05); *C09K 2211/1007* (2013.01); *C09K 2211/1011* (2013.01); *C09K 2211/1014* (2013.01); *H10K 50/15* (2023.02); *H10K 85/626* (2023.02)

(58) Field of Classification Search

None

See application file for complete search history.

(56) References Cited

U.S. PATENT DOCUMENTS

| | | | | |
|---|---|---|---|---|
| 2007/0029927 | A1 | 2/2007 | Kawamura et al. | |
| 2017/0018710 | A1* | 1/2017 | Mujica-Fernaud | ... C07C 211/54 |
| 2023/0371374 | A1* | 11/2023 | Cho | ..................... H10K 85/633 |

FOREIGN PATENT DOCUMENTS

| | | | | |
|---|---|---|---|---|
| JP | 2020019748 A | * 2/2020 | | |
| KR | 20090132352 A | * 12/2009 | ............. H10K 50/00 | |

OTHER PUBLICATIONS

CAS Abstract and Indexed Compounds, J. Park et al., KR 2009132352 (2009) (Year: 2009).*
Search Report from CNIPA for Chinese application No. 202110463707.6; Application Date: Apr. 25, 2021.
JP2020019748 Translation.
Request for the Submission of an Opinion from Korea Intellectual Property Office, Application No. 10-2020-0060388, Filing Date: May 20, 2020.

* cited by examiner

*Primary Examiner* — Alexander R Pagano
(74) *Attorney, Agent, or Firm* — G. Creston Campbell

(57) ABSTRACT

The present disclosure relates to an organic electroluminescent compound and an organic electroluminescent device comprising the same. The organic electroluminescent device with improved driving voltage and/or power efficiency can be provided by using the organic electroluminescent compound according to the present disclosure.

8 Claims, No Drawings

ORGANIC ELECTROLUMINESCENT COMPOUND AND ORGANIC ELECTROLUMINESCENT DEVICE COMPRISING THE SAME

CLAIM OF BENEFIT OF PRIOR APPLICATION

This application claims priority under 35 U.S.C. § 120 from U.S. patent application Ser. No. 17/322,420, filed May 17, 2021, which is the U.S. Entry of KR 10-2020-0060388, filed May 20, 2020, all of which are incorporated by reference herein in their entirety.

TECHNICAL FIELD

The present disclosure relates to an organic electroluminescent compound and an organic electroluminescent device comprising the same.

BACKGROUND ART

An electroluminescent device (EL device) is a self-light-emitting display device which has advantages in that it provides a wider viewing angle, a greater contrast ratio, and a faster response time. The first organic EL device was developed by Eastman Kodak in 1987, by using small aromatic diamine molecules and aluminum complexes as materials for forming a light-emitting layer (see Appl. Phys. Lett. 51, 913, 1987).

An organic electroluminescent device has a multilayer structure including a hole injection layer, a hole transport layer, a light-emitting layer, an electron transport layer, an electron injection layer, etc. in order to increase the efficiency and stability thereof. In this case, selection of a compound included in the hole transport layer, etc. is recognized as one of the means for improving device characteristics such as hole transport efficiency to the light-emitting layer, light emission efficiency, and lifetime.

In this regard, copper phthalocyanine (CuPc), 4,4'-bis[N-(1-naphthyl)-N-phenylamino]biphenyl (NPB), N,N'-diphenyl-N,N'-bis(3-methylphenyl)-(1,1'-biphenyl)-4,4'-diamine (TPD), 4,4',4"-tris(3-methylphenylamino)triphenylamine (MTDATA), etc. have been used as a hole injection and transport material in an organic electroluminescent device; however, there has been a problem that the quantum efficiency and lifetime of the organic electroluminescent device were deteriorated when such a material is used. The reason is that when the organic electroluminescent device is driven at a high current, thermal stress occurs between an anode and a hole injection layer, and the lifetime of the device is drastically reduced by such thermal stress. In addition, since the holes in the organic material used in a hole injection layer has very high mobility, the hole-electron charge balance is broken, which results in lowering the quantum efficiency (cd/A).

Therefore, there is still a need to develop a hole transport material for improving the performance of an organic electroluminescent device.

KR Patent No. 1756611 discloses phenanthrene derivatives, but fails to specifically disclose the organic electroluminescent compound according to the present disclosure.

DISCLOSURE OF INVENTION

Technical Problems

The objective of the present disclosure is, firstly, to provide an organic electroluminescent compound effective to prepare an organic electroluminescent device with improved driving voltage and/or power efficiency properties, and secondly, to provide an organic electroluminescent device comprising the organic electroluminescent compound.

Solution to Problem

As a result of intensive research to solve the above technical problems, the present inventors have completed the present invention by finding that the organic electroluminescent compound represented by the following formula 1 achieves the above objective.

(1)

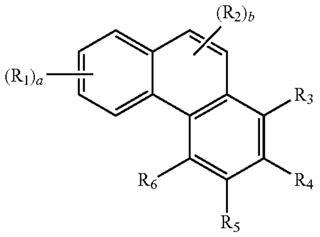

wherein $R_3$ to $R_6$ each independently represent hydrogen, deuterium, a halogen, a cyano, a substituted or unsubstituted (C1-C30)alkyl, a substituted or unsubstituted (C6-C30) aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, or the group represented by the following formula A;

(A)

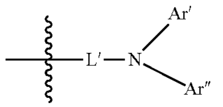

at least two of $R_3$ to $R_6$ each independently are represented by formula A, with a proviso that both $R_3$ and $R_6$ are not simultaneously represented by formula A;

L' each independently represents a single bond, a substituted or unsubstituted (C1-C30)alkylene, a substituted or unsubstituted (C6-C30)arylene, a substituted or unsubstituted (3- to 30-membered)heteroarylene, or a substituted or unsubstituted (C3-C30)cycloalkylene;

Ar' and Ar" each independently represent a substituted or unsubstituted (C6-C30)aryl, a substituted or unsubstituted (3- to 30-membered)heteroaryl, or a substituted or unsubstituted fused ring of a (C3-C30)aliphatic ring(s) and a (C6-C30)aromatic ring(s);

$R_1$ and $R_2$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, or -$L_3$-N—($Ar_5$)($Ar_6$); or may be linked to an adjacent substituent to form a ring;

$L_3$ each independently represents a single bond, a substituted or unsubstituted (C6-C30)arylene, or a substituted or unsubstituted (3- to 30-membered)heteroarylene;

$Ar_5$ and $Ar_6$ each independently represent hydrogen, a substituted or unsubstituted (C1-C30)alkyl, a substituted or unsubstituted (C2-C30)alkenyl, a substituted or unsubstituted fused ring of a (C3-C30)aliphatic ring(s) and a (C6-C30)aromatic ring(s), a substituted or unsubstituted (C6-C30)aryl, or a substituted or unsubstituted (3- to 30-membered)heteroaryl;

a is an integer of 1 to 4, b is 1 or 2, and when a and b are each an integer of 2 or more, each of $R_1$ and $R_2$ may be the same or different from each other; and when there are a plurality of substituents represented by the same symbol, each of the substituents represented by the same symbol may be the same or different from each other.

Advantageous Effects of Invention

The present disclosure provides an organic electroluminescent device with improved driving voltage and/or power efficiency properties by using the organic electroluminescent compound according to the present disclosure.

MODE FOR THE INVENTION

Hereinafter, the present disclosure will be described in detail. However, the following description is intended to explain the invention, and is not meant to restrict the scope of the invention.

The term "organic electroluminescent compound" in the present disclosure means a compound that may be used in an organic electroluminescent device, and may be comprised in any layer constituting an organic electroluminescent device, as necessary.

The term "organic electroluminescent material" in the present disclosure means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material, an electron buffer material, a hole blocking material, an electron transport material, or an electron injection material.

The organic electroluminescent material of the present disclosure may comprise one or more types of the compound represented by formula 1. The compound of formula 1 may be comprised in one or more layers constituting an organic electroluminescent device, and may be comprised in at least one layer of the layers constituting a hole transport zone, but is not limited thereto. When the compound of formula 1 is comprised in a hole transport layer, a hole auxiliary layer, a light-emitting auxiliary layer, or an electron blocking layer, it may be comprised as a hole transport material, a hole auxiliary material, a light-emitting auxiliary material, or an electron blocking material.

Hereinafter, the compound represented by formula 1 will be described in more detail.

Herein, the term "(C1-C30)alkyl" is meant to be a linear or branched alkyl having 1 to 30 carbon atoms constituting the chain, in which the number of carbon atoms is preferably 1 to 20, and more preferably 1 to 10. The above alkyl may include methyl, ethyl, n-propyl, isopropyl, n-butyl, isobutyl, tert-butyl, sec-butyl, etc. The term "(C2-C30)alkenyl" is meant to be a linear or branched alkenyl having 2 to 30 carbon atoms constituting the chain, in which the number of carbon atoms is preferably 2 to 20, and more preferably 2 to 10. The above alkenyl may include vinyl, 1-propenyl, 2-propenyl, 1-butenyl, 2-butenyl, 3-butenyl, 2-methylbut-2-enyl, etc. The term "(C2-C30)alkynyl" is meant to be a linear or branched alkynyl having 2 to 30 carbon atoms constituting the chain, in which the number of carbon atoms is preferably 2 to 20, and more preferably 2 to 10. The above alkynyl may include ethynyl, 1-propynyl, 2-propynyl, 1-butynyl, 2-butynyl, 3-butynyl, 1-methylpent-2-ynyl, etc. The term "(C3-C30)cycloalkyl" is meant to be a mono- or polycyclic hydrocarbon having 3 to 30 ring backbone carbon atoms, in which the number of carbon atoms is preferably 3 to 20, and more preferably 3 to 7. The above cycloalkyl may include cyclopropyl, cyclobutyl, cyclopentyl, cyclohexyl, cyclopentylmethyl, cyclohexylmethyl, etc. The term "(3- to 7-membered)heterocycloalkyl" is meant to be a cycloalkyl having 3 to 7, preferably 5 to 7 ring backbone atoms, and including at least one heteroatom selected from the group consisting of B, N, O, S, Si, and P, preferably at least one heteroatom selected from the group consisting of O, S, and N. The above heterocycloalkyl may include tetrahydrofuran, pyrrolidine, thiolane, tetrahydropyran, etc. The term "(C6-C30)aryl(ene) or (C6-C50)aryl(ene)" is meant to be a monocyclic or fused ring radical derived from an aromatic hydrocarbon having 6 to 30 or 6 to 50 ring backbone carbon atoms, which may be partially saturated. The number of ring backbone carbon atoms is preferably 6 to 25, and more preferably 6 to 18. The above aryl comprises those having a spiro structure. The above aryl may include phenyl, biphenyl, terphenyl, naphthyl, binaphthyl, phenylnaphthyl, naphthylphenyl, phenylterphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, azulenyl, tetramethyldihydrophenanthrenyl, etc. More specifically, the aryl may include phenyl, 1-naphthyl, 2-naphthyl, 1-anthryl, 2-anthryl, 9-anthryl, benzanthryl, 1-phenanthryl, 2-phenanthryl, 3-phenanthryl, 4-phenanthryl, 9-phenanthryl, naphthacenyl, pyrenyl, 1-chrysenyl, 2-chrysenyl, 3-chrysenyl, 4-chrysenyl, 5-chrysenyl, 6-chrysenyl, benzo[c]phenanthryl, benzo[g]chrysenyl, 1-triphenylenyl, 2-triphenylenyl, 3-triphenylenyl, 4-triphenylenyl, 1-fluorenyl, 2-fluorenyl, 3-fluorenyl, 4-fluorenyl, 9-fluorenyl, benzo[a]fluorenyl, benzo[b]fluorenyl, benzo[c]fluorenyl, dibenzofluorenyl, 2-biphenylyl, 3-biphenylyl, 4-biphenylyl, o-terphenyl, m-terphenyl-4-yl, m-terphenyl-3-yl, m-terphenyl-2-yl, p-terphenyl-4-yl, p-terphenyl-3-yl, p-terphenyl-2-yl, m-quaterphenyl, 3-fluoranthenyl, 4-fluoranthenyl, 8-fluoranthenyl, 9-fluoranthenyl, benzofluoranthenyl, o-tolyl, m-tolyl, p-tolyl, 2,3-xylyl, 3,4-xylyl, 2,5-xylyl, mesityl, o-cumenyl, m-cumenyl, p-cumenyl, p-tert-butylphenyl, p-(2-phenylpropyl)phenyl, 4'-methylbiphenylyl, 4"-tert-butyl-p-terphenyl-4-yl, 9,9-dimethyl-1-fluorenyl, 9,9-dimethyl-2-fluorenyl, 9,9-dimethyl-3-fluorenyl, 9,9-dimethyl-4-fluorenyl, 9,9-diphenyl-1-fluorenyl, 9,9-diphenyl-2-fluorenyl, 9,9-diphenyl-3-fluorenyl, 9,9-diphenyl-4-fluorenyl, 11,11-dimethyl-1-benzo

[a]fluorenyl, 11,11-dimethyl-2-benzo[a]fluorenyl, 11,11-dimethyl-3-benzo[a]fluorenyl, 11,11-dimethyl-4-benzo[a]fluorenyl, 11,11-dimethyl-5-benzo[a]fluorenyl, 11,11-dimethyl-6-benzo[a]fluorenyl, 11,11-dimethyl-7-benzo[a]fluorenyl, 11,11-dimethyl-8-benzo[a]fluorenyl, 11,11-dimethyl-9-benzo[a]fluorenyl, 11,11-dimethyl-10-benzo[a]fluorenyl, 11,11-dimethyl-1-benzo[b]fluorenyl, 11,11-dimethyl-2-benzo[b]fluorenyl, 11,11-dimethyl-3-benzo[b]fluorenyl, 11,11-dimethyl-4-benzo[b]fluorenyl, 11,11-dimethyl-5-benzo[b]fluorenyl, 11,11-dimethyl-6-benzo[b]fluorenyl, 11,11-dimethyl-7-benzo[b]fluorenyl, 11,11-dimethyl-8-benzo[b]fluorenyl, 11,11-dimethyl-9-benzo[b]fluorenyl, 11,11-dimethyl-10-benzo[b]fluorenyl, 11,11-dimethyl-1-benzo[c]fluorenyl, 11,11-dimethyl-2-benzo[c]fluorenyl, 11,11-dimethyl-3-benzo[c]fluorenyl, 11,11-dimethyl-4-benzo[c]fluorenyl, 11,11-dimethyl-5-benzo[c]fluorenyl, 11,11-dimethyl-6-benzo[c]fluorenyl, 11,11-dimethyl-7-benzo[c]fluorenyl, 11,11-dimethyl-8-benzo[c]fluorenyl, 11,11-dimethyl-9-benzo[c]fluorenyl, 11,11-dimethyl-10-benzo[c]fluorenyl, 11,11-diphenyl-1-benzo[a]fluorenyl, 11,11-diphenyl-2-benzo[a]fluorenyl, 11,11-diphenyl-3-benzo[a]fluorenyl, 11,11-diphenyl-4-benzo[a]fluorenyl, 11,11-diphenyl-5-benzo[a]fluorenyl, 11,11-diphenyl-6-benzo[a]fluorenyl, 11,11-diphenyl-7-benzo[a]fluorenyl, 11,11-diphenyl-8-benzo[a]fluorenyl, 11,11-diphenyl-9-benzo[a]fluorenyl, 11,11-diphenyl-10-benzo[a]fluorenyl, 11,11-diphenyl-1-benzo[b]fluorenyl, 11,11-diphenyl-2-benzo[b]fluorenyl, 11,11-diphenyl-3-benzo[b]fluorenyl, 11,11-diphenyl-4-benzo[b]fluorenyl, 11,11-diphenyl-5-benzo[b]fluorenyl, 11,11-diphenyl-6-benzo[b]fluorenyl, 11,11-diphenyl-7-benzo[b]fluorenyl, 11,11-diphenyl-8-benzo[b]fluorenyl, 11,11-diphenyl-9-benzo[b]fluorenyl, 11,11-diphenyl-10-benzo[b]fluorenyl, 11,11-diphenyl-1-benzo[c]fluorenyl, 11,11-diphenyl-2-benzo[c]fluorenyl, 11,11-diphenyl-3-benzo[c]fluorenyl, 11,11-diphenyl-4-benzo[c]fluorenyl, 11,11-diphenyl-5-benzo[c]fluorenyl, 11,11-diphenyl-6-benzo[c]fluorenyl, 11,11-diphenyl-7-benzo[c]fluorenyl, 11,11-diphenyl-8-benzo[c]fluorenyl, 11,11-diphenyl-9-benzo[c]fluorenyl, 11,11-diphenyl-10-benzo[c]fluorenyl, 9,9,10,10-tetramethyl-9,10-dihydro-1-phenanthrenyl, 9,9,10,10-tetramethyl-9,10-dihydro-2-phenanthrenyl, 9,9,10,10-tetramethyl-9,10-dihydro-3-phenanthrenyl, 9,9,10,10-tetramethyl-9,10-dihydro-4-phenanthrenyl, etc.

The term "(3- to 30-membered)heteroaryl(ene) or (3- to 50-membered)heteroaryl(ene)" means an aryl group having 3 to 30 or 3 to 50 ring backbone atoms and including at least one heteroatom(s) selected from the group consisting of B, N, O, S, Si, and P. The number of heteroatoms is preferably 1 to 4. The above heteroaryl(ene) may be a monocyclic ring or a fused ring condensed with at least one benzene ring, and may be partially saturated. In addition, the above heteroaryl (ene) comprises the form in which at least one heteroaryl or aryl group is linked to a heteroaryl group via a single bond(s), and also comprises those having a spiro structure. The above heteroaryl may include a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl such as benzofuranyl, benzothiophenyl, isobenzofuranyl, dibenzofuranyl, dibenzothiophenyl, dibenzoselenophenyl, naphthobenzofuranyl, naphthobenzothiophenyl, benzofuroquinolyl, benzofuroquinazolinyl, benzofuronaphthyridinyl, benzofuropyrimidinyl, naphthofuropyrimidinyl, benzothienoquinolyl, benzothienoquinazolinyl, benzothienonaphthyridinyl, benzothienopyrimidinyl, naphthothienopyrimidinyl, pyrimidoindolyl, benzopyrimidoindolyl, benzofuropyrazinyl, naphthofuropyrazinyl, benzothienopyrazinyl, naphthothienopyrazinyl, pyrazinoindolyl, benzopyrazinoindolyl, benzimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, benzoquinazolinyl, quinoxalinyl, benzoquinoxalinyl, naphthyridinyl, carbazolyl, benzocarbazolyl, dibenzocarbazolyl, phenoxazinyl, phenothiazinyl, phenanthridinyl, benzodioxolyl, dihydroacridinyl, benzotriazolephenazinyl, imidazopyridyl, chromenoquinazolinyl, thiochromenoquinazolinyl, dimethylbenzoperimidinyl, indolocarbazolyl, indenocarbazolyl, etc. More specifically, the heteroaryl may include 1-pyrrolyl, 2-pyrrolyl, 3-pyrrolyl, pyrazinyl, 2-pyridyl, 2-pyrimidinyl, 4-pyrimidinyl, 5-pyrimidinyl, 6-pyrimidinyl, 1,2,3-triazin-4-yl, 1,2,4-triazin-3-yl, 1,3,5-triazin-2-yl, 1-imidazolyl, 2-imidazolyl, 1-pyrazolyl, 1-indolidinyl, 2-indolidinyl, 3-indolidinyl, 5-indolidinyl, 6-indolidinyl, 7-indolidinyl, 8-indolidinyl, 2-imidazopyridyl, 3-imidazopyridyl, 5-imidazopyridyl, 6-imidazopyridyl, 7-imidazopyridyl, 8-imidazopyridyl, 3-pyridyl, 4-pyridyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, azacarbazolyl-1-yl, azacarbazolyl-2-yl, azacarbazolyl-3-yl, azacarbazolyl-4-yl, azacarbazolyl-5-yl, azacarbazolyl-6-yl, azacarbazolyl-7-yl, azacarbazolyl-8-yl, azacarbazolyl-9-yl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrol-1-yl, 2-methylpyrrol-3-yl, 2-methylpyrrol-4-yl, 2-methylpyrrol-5-yl, 3-methylpyrrol-1-yl, 3-methylpyrrol-2-yl, 3-methylpyrrol-4-yl, 3-methylpyrrol-5-yl, 2-tert-butylpyrrol-4-yl, 3-(2-phenylpropyl)pyrrol-1-yl, 2-methyl-1-indolyl, 4-methyl-1-indolyl, 2-methyl-3-indolyl, 4-methyl-3-indolyl, 2-tert-butyl-1-indolyl, 4-tert-butyl-1-indolyl, 2-tert-butyl-3-indolyl, 4-tert-butyl-3-indolyl, 1-dibenzofuranyl, 2-dibenzofuranyl, 3-dibenzofuranyl, 4-dibenzofuranyl, 1-dibenzothiophenyl, 2-dibenzothiophenyl, 3-dibenzothiophenyl, 4-dibenzothiophenyl, 1-naphtho-[1,2-b]-benzofuranyl, 2-naphtho-[1,2-b]-benzofuranyl, 3-naphtho-[1,2-b]-benzofuranyl, 4-naphtho-[1,2-b]-benzofuranyl, 5-naphtho-[1,2-b]-benzofuranyl, 6-naphtho-[1,2-b]-benzofuranyl, 7-naphtho-[1,2-b]-benzofuranyl, 8-naphtho-[1,2-b]-benzofuranyl, 9-naphtho-[1,2-b]-benzofuranyl, 10-naphtho-[1,2-b]-benzofuranyl, 1-naphtho-[2,3-b]-benzofuranyl, 2-naphtho-[2,3-b]-benzofuranyl, 3-naphtho-[2,3-b]-benzofuranyl, 4-naphtho-[2,3-b]-benzofuranyl, 5-naphtho-[2,3-b]-benzofuranyl, 6-naphtho-[2,3-b]-benzofuranyl, 7-naphtho-[2,3-b]-benzofuranyl, 8-naphtho-[2,3-b]-benzofuranyl, 9-naphtho-[2,3-b]-benzofuranyl, 10-naphtho-[2,3-b]-benzofuranyl, 1-naphtho-[2,1-b]-benzofuranyl, 2-naphtho-[2,1-b]-benzofuranyl, 3-naphtho-[2,1-b]-benzofuranyl, 4-naphtho-[2,1-b]-benzofuranyl, 5-naphtho-[2,1-b]-benzofuranyl, 6-naphtho-[2,1-b]-benzofuranyl, 7-naphtho-[2,1-b]-benzofuranyl, 8-naphtho-[2,1-b]-benzofuranyl, 9-naphtho-[2,1-b]-benzofuranyl, 10-naphtho-[2,1-b]-benzofuranyl, 1-naphtho-[1,2-b]-benzothiophenyl, 2-naphtho-[1,2-b]-benzothiophenyl, 3-naphtho-[1,2-b]-benzothiophenyl, 4-naphtho-[1,2-b]-benzothiophenyl, 5-naphtho-[1,2-b]-benzothiophenyl, 6-naphtho-[1,2-b]-benzothiophenyl, 7-naphtho-[1,2-b]-benzothiophenyl, 8-naphtho-[1,2-b]-benzothiophenyl, 9-naphtho-[1,2-b]-benzothiophenyl, 10-naphtho-[1,2-b]-benzothiophenyl, 1-naphtho-[2,3-b]-benzothiophenyl, 2-naphtho-[2,3-b]-benzothiophenyl, 3-naphtho-[2,3-b]-benzothiophenyl, 4-naphtho-[2,3-b]-benzothiophenyl, 5-naphtho-[2,3-b]-benzothiophenyl, 1-naphtho-[2,1-b]-benzothiophenyl, 2-naphtho-[2,1-b]-benzothiophenyl, 3-naphtho-[2,1-b]-benzothiophenyl, 4-naphtho-[2,1-b]-benzothiophenyl, 5-naphtho-[2,1-b]-benzothiophenyl, 6-naphtho-[2,1-b]-benzothiophenyl, 7-naphtho-[2,1-b]-benzothiophenyl, 8-naphtho-[2,1-b]-benzothiophenyl, 9-naphtho-[2,1-b]-benzothiophenyl, 10-naphtho-[2,1-b]-benzothiophenyl, 2-benzofuro[3,2-d]pyrimidinyl, 6-benzofuro[3,2-d]pyrimidinyl, 7-benzofuro[3,2-d]pyrimidinyl, 8-benzofuro[3,2-d]pyrimidinyl, 9-benzofuro[3,2-d]pyrimidinyl, 2-benzothio[3,2-d]pyrimidinyl, 6-benzothio[3,2-d]pyrimidinyl, 7-benzothio[3,2-d]pyrimidinyl, 8-benzothio[3,2-d]pyrimidinyl, 9-benzothio[3,2-d]pyrimidinyl, 2-benzofuro[3,2-d]pyrazinyl, 6-benzofuro[3,2-d]pyrazinyl, 7-benzofuro[3,2-d]pyrazinyl, 8-benzofuro[3,2-d]pyrazinyl, 9-benzofuro[3,2-d]pyrazinyl, 2-benzothio[3,2-d]pyrazinyl, 6-benzothio[3,2-d]pyrazinyl, 7-benzothio[3,2-d]pyrazinyl, 8-benzothio[3,2-d]pyrazinyl, 9-benzothio[3,2-d]pyrazinyl, 1-silafluorenyl, 2-silafluorenyl, 3-silafluorenyl, 4-silafluorenyl, 1-germafluorenyl, 2-germafluorenyl, 3-germafluorenyl, 4-germafluorenyl, 1-dibenzoselenophenyl, 2-dibenzoselenophenyl, 3-dibenzoselenophenyl, 4-dibenzoselenophenyl, etc.

The term "a fused ring of a (C3-C30)aliphatic ring(s) and a (C6-C30)aromatic ring(s)" means a functional group of a fused ring of one or more aliphatic ring(s) having 3 to 30, preferably 3 to 25, and more preferably 3 to 18 ring backbone carbon atoms and one or more aromatic ring(s) having 6 to 30, preferably 6 to 25, and more preferably 6 to 18 ring backbone carbon atoms. For example, a fused ring of a (C3-C30)aliphatic ring(s) and a (C6-C30)aromatic ring(s) may be a fused ring of one or more benzene(s) and one or more cyclohexane(s), a fused ring of one or more naphthalene(s) and one or more cyclopentane(s), etc. In the present disclosure, carbon atom in a fused ring of a (C3-C30)aliphatic ring(s) and a (C6-C30)aromatic ring(s) may be replaced with one or more heteroatoms selected from B, N, O, S, Si, and P, preferably with one or more heteroatoms selected from N, O, and S. In the present disclosure, "halogen" includes F, Cl, Br, and I.

In addition, "ortho (o-)," "meta (m-)," and "para (p-)" are prefixes, which represent the relative positions of substituents, respectively. Ortho indicates that two substituents are adjacent to each other, and for example, when two substituents in a benzene derivative occupy positions 1 and 2, it is called an ortho position. Meta indicates that two substituents are at positions 1 and 3, and for example, when two substituents in a benzene derivative occupy positions 1 and 3, it is called a meta position. Para indicates that two substituents are at positions 1 and 4, and for example, when two substituents in a benzene derivative occupy positions 1 and 4, it is called a para position.

In addition, "substituted" in the expression "substituted or unsubstituted" means that a hydrogen atom in a certain functional group is replaced with another atom or another functional group (i.e., a substituent), and also comprises being substituted with a group in which two or more of the substituents are linked. For example, "a substituent in which two or more substituents are linked" may be pyridine-triazine. That is, pyridine-triazine may be interpreted as one heteroaryl substituent or the substituent in which two heteroaryl substituents are linked. In formulas of the present disclosure, the substituents of the substituted alkyl, the substituted alkylene, the substituted alkenyl, the substituted aryl, the substituted arylene, the substituted heteroaryl, the substituted heteroarylene, the substituted cycloalkyl, the substituted cycloalkylene, the substituted alkoxy, the substituted trialkylsilyl, the substituted dialkylarylsilyl, the substituted alkyldiarylsilyl, the substituted triarylsilyl, and the substituted fused ring of an aliphatic ring(s) and an aromatic ring(s) each independently, are at least one selected from the group consisting of deuterium; a halogen; a cyano; a carboxyl; a nitro; a hydroxyl; a phosphine oxide; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (5- to 50-membered)heteroaryl unsubstituted or substituted with at least one of a (C1-C30)alkyl(s), a (C6-C30)aryl(s), and a di(C6-C30)arylamino(s); a (C6-C30)aryl unsubstituted or substituted with at least one of a (C1-C30)alkyl(s), a (3- to 50-membered)heteroaryl(s), and a mono- or di-(C6-C30)arylamino(s); a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C2-C30)alkenylamino; a mono- or di-(C6-C30)arylamino unsubstituted or substituted with at least one of a (C1-C30)alkyl(s), a (5- to 30-membered)heteroaryl(s), and a di(C6-C30)arylamino(s); a mono- or di-(3- to 30-membered)heteroarylamino; a (C1-C30)alkyl(C2-C30)alkenylamino; a (C1-C30)alkyl(C6-C30)arylamino; a (C1-C30)alkyl(3- to 30-membered)heteroarylamino; a (C2-C30)alkenyl(C6-C30)arylamino; a (C2-C30)alkenyl(3- to 30-membered)heteroarylamino; a (C6-C30)aryl(3- to 30-membered)heteroarylamino; a (C1-C30)alkylcarbonyl; a (C1-C30)alkoxycarbonyl; a (C6-C30)arylcarbonyl; a (C6-C30)arylphosphine; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl. According to one embodiment of the present disclosure, the substituents, each independently, are at least one selected from the group consisting of deuterium, a (C1-C20)alkyl, and a (C6-C25)aryl. According to another embodiment of the present disclosure, the substituents, each independently, are at least one selected from the group consisting of a (C1-C6)alkyl and a (C6-C20)aryl. For example, the substituents may be methyl, phenyl, naphthyl, biphenyl, etc.

Formula 1 may be represented by the following formula 1-1 or 1-2:

(1-1)

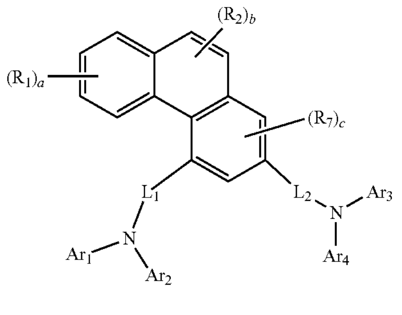

-continued (1-2)

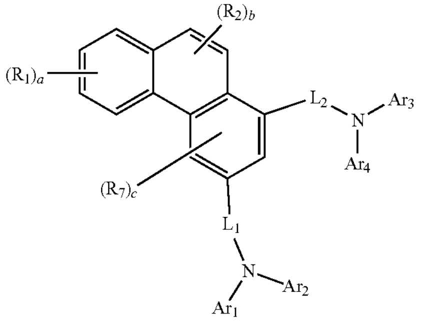

wherein $L_1$ and $L_2$ each independently are as L' defined in formula 1; $Ar_1$ to $Ar_4$ each independently are as Ar' and Ar" defined in formula 1; $R_7$ is as $R_1$ and $R_2$ defined in formula 1; c is 1 or 2, wherein in the case where c is 2, each $R_7$ may be the same of different from each other; and $R_1$, $R_2$, a, and b are as defined in formula 1.

In formula 1, $R_3$ to $R_6$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30) cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, or the group represented by formula A. At least two of $R_3$ to $R_6$ each independently are represented by formula A, with a proviso that both $R_3$ and $R_6$ are not simultaneously represented by formula A. According to one embodiment of the present disclosure, $R_3$ to $R_6$, which are not represented by formula A, represent hydrogen.

L' each independently represents a single bond, a substituted or unsubstituted (C1-C30)alkylene, a substituted or unsubstituted (C6-C30)arylene, a substituted or unsubstituted (3- to 30-membered)heteroarylene, or a substituted or unsubstituted (C3-C30)cycloalkylene. According to one embodiment of the present disclosure, L' each independently represents a single bond, or a substituted or unsubstituted (C6-C12)arylene. According to another embodiment of the present disclosure, L' each independently represents a single bond, or a substituted or unsubstituted (C6-C12)arylene. For example, L' may be each independently a single bond, phenylene, naphthylene, etc.

Ar' and Ar" each independently represent a substituted or unsubstituted (C6-C30)aryl, a substituted or unsubstituted (3- to 30-membered)heteroaryl, or a substituted or unsubstituted fused ring of a (C3-C30)aliphatic ring(s) and a (C6-C30)aromatic ring(s); or may be linked to an adjacent substituent to form a ring. According to another embodiment of the present disclosure, Ar' and Ar" each independently represent a substituted or unsubstituted (C6-C25)aryl, a substituted or unsubstituted (5- to 20-membered)heteroaryl, or a substituted or unsubstituted fused ring of a (C3-C10) aliphatic ring(s) and a (C6-C15)aromatic ring(s). According to another embodiment of the present disclosure, Ar' and Ar" each independently represent a (C6-C25)aryl unsubstituted or substituted with at least one of a (C1-C6)alkyl(s) and a (C6-C12)aryl(s); a (5- to 20-membered)heteroaryl unsubstituted or substituted with at least one (C6-C12)aryl(s); or a fused ring of a (C3-C10)aliphatic ring(s) and a (C6-C15) aromatic ring(s) unsubstituted or substituted with at least one (C1-C6)alkyl(s). For example, Ar' and Ar" may be each independently phenyl; naphthyl; biphenyl; phenanthrenyl; naphthylphenyl; phenylnaphthyl; diphenylfluorenyl unsubstituted or substituted with phenyl; dimethylfluorenyl unsubstituted or substituted with phenyl; dimethylbenzofluorenyl; dibenzofuranyl unsubstituted or substituted with phenyl; dibenzothiophenyl unsubstituted or substituted with phenyl; benzonaphthofuranyl; benzonaphthothiophenyl; carbazolyl unsubstituted or substituted with at least one of phenyl, naphthyl, and biphenyl; 9,10-tetramethylphenanthrenyl, etc.

$R_1$ and $R_2$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, or $-L_3-N-(Ar_5)(Ar_6)$; or may be linked to an adjacent substituent to form a ring. According to one embodiment of the present disclosure, $R_1$ and $R_2$ each independently represent hydrogen, deuterium, a substituted or unsubstituted (C6-C15)aryl, a substituted or unsubstituted (5- to 15-membered)heteroaryl, or $-L_3-N-(Ar_5)(Ar_6)$. According to another embodiment of the present disclosure, $R_1$ and $R_2$ each independently represent hydrogen; a (C6-C15)aryl unsubstituted or substituted with at least one (C1-C6)alkyl(s); a (5- to 15-membered)heteroaryl unsubstituted or substituted with at least one (C6-C12)aryl(s); or $-L_3-N-(Ar_5)(Ar_6)$. For example, $R_1$ and $R_2$ may be each independently hydrogen, phenyl, naphthyl, phenanthrenyl, dimethylfluorenyl, dibenzofuranyl, carbazolyl substituted with phenyl, diphenylamino, etc.

$L_3$ each independently represents a single bond, a substituted or unsubstituted (C6-C30)arylene, or a substituted or unsubstituted (3- to 30-membered)heteroarylene. According to one embodiment of the present disclosure, $L_3$ each independently represents a single bond.

$Ar_5$ and $Ar_6$ each independently represent hydrogen, a substituted or unsubstituted (C1-C30)alkyl, a substituted or unsubstituted (C2-C30)alkenyl, a substituted or unsubstituted fused ring of a (C3-C30)aliphatic ring(s) and a (C6-C30)aromatic ring(s), a substituted or unsubstituted (C6-C30)aryl, or a substituted or unsubstituted (3- to 30-membered)heteroaryl. According to one embodiment of the present disclosure, $Ar_5$ and $Ar_6$ each independently represent a substituted or unsubstituted (C6-C12)aryl. According to another embodiment of the present disclosure, $Ar_5$ and $Ar_6$ each independently represent an unsubstituted (C6-C12)aryl. For example, $Ar_5$ and $Ar_6$ may be each independently phenyl, etc.

According to one embodiment of the present disclosure, in formula 1, $R_3$ to $R_6$, which are not represented by formula A, represent hydrogen; L' each independently represents a single bond, or a substituted or unsubstituted (C6-C12) arylene; Ar' and Ar" each independently represent a substituted or unsubstituted (C6-C25)aryl, a substituted or unsubstituted (5- to 20-membered)heteroaryl, or a substituted or unsubstituted fused ring of a (C3-C10)aliphatic ring(s) and a (C6-C15)aromatic ring(s); $R_1$ and $R_2$ each independently represent hydrogen, deuterium, a substituted or unsubstituted (C6-C15)aryl, a substituted or unsubstituted (5- to 15-membered)heteroaryl, or $-L_3-N-(Ar_5)(Ar_6)$; $L_3$ each independently represents a single bond; and $Ar_5$ and $Ar_6$ each independently represent a substituted or unsubstituted (C6-C12)aryl.

According to another embodiment of the present disclosure, in formula 1, $R_3$ to $R_6$, which are not represented by formula A, represent hydrogen; L' each independently represents a single bond, or a substituted or unsubstituted (C6-C12)arylene; Ar' and Ar" each independently represent a (C6-C25)aryl unsubstituted or substituted with at least one of a (C1-C6)alkyl(s) and a (C6-C12)aryl(s); a (5- to 20-membered)heteroaryl unsubstituted or substituted with at least one (C6-C12)aryl(s); or a fused ring of a (C3-C10) aliphatic ring(s) and a (C6-C15)aromatic ring(s) unsubstituted or substituted with at least one (C1-C6)alkyl(s); $R_1$ and $R_2$ each independently represent hydrogen; a (C6-C15)aryl unsubstituted or substituted with at least one (C1-C6) alkyl(s); a (5- to 15-membered)heteroaryl unsubstituted or substituted with at least one (C6-C12)aryl(s); or $-L_3$-N—$(Ar_5)(Ar_6)$; $L_3$ each independently represents a single bond; and $Ar_5$ and $Ar_6$ each independently represent an unsubstituted (C6-C12)aryl.

In the formulas of the present disclosure, in case a substituent is linked to an adjacent substituent to form a ring, the ring may be a substituted or unsubstituted mono- or polycyclic (3- to 30-membered) alicyclic or aromatic ring, or the combination thereof formed from at least two adjacent substituents being linked. In addition, the formed ring may contain at least one heteroatom selected from B, N, O, S, Si, and P, preferably at least one heteroatom selected from N, O, and S. According to one embodiment of the present disclosure, the number of ring backbone atoms is (5- to 20-membered), and according to another embodiment of the present disclosure, the number of ring backbone atoms is (5- to 15-membered). For example, the fused ring may be in the form of a substituted or unsubstituted dibenzothiophene ring, a substituted or unsubstituted dibenzofuran ring, a substituted or unsubstituted naphthalene ring, a substituted or unsubstituted phenanthrene ring, a substituted or unsubstituted fluorene ring, a substituted or unsubstituted benzothiophene ring, a substituted or unsubstituted benzofuran ring, a substituted or unsubstituted indole ring, a substituted or unsubstituted indene ring, a substituted or unsubstituted benzene ring, or a substituted or unsubstituted carbazole ring.

In the formulas of the present disclosure, the heteroaryl and heteroarylene, each independently, may contain at least one heteroatom selected from B, N, O, S, Si, and P. Also, the heteroatom may be bonded to at least one selected from the group consisting of hydrogen, deuterium, a halogen, a cyano, a substituted or unsubstituted (C1-C30)alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted (C1-C30)alkoxy, a substituted or unsubstituted tri (C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, and a substituted or unsubstituted (C1-C30)alkyl(C6-C30)arylamino.

The compound represented by formula 1 may be specifically exemplified by the following compounds, but is not limited thereto.

A-1

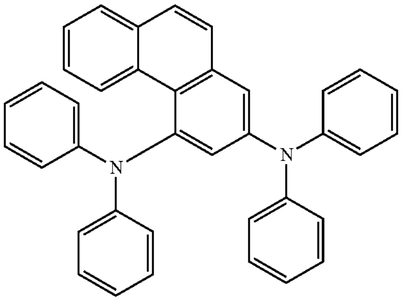

A-2

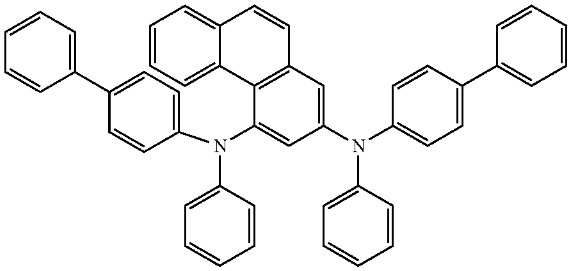

A-3

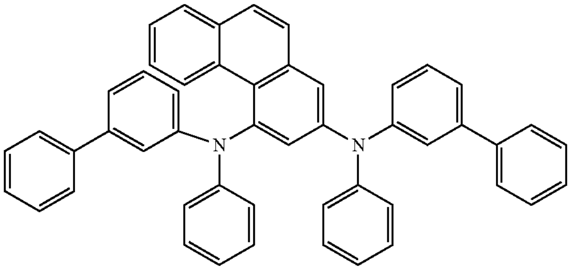

A-4

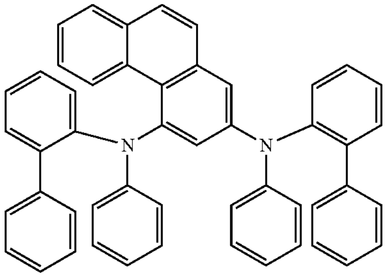

-continued
A-5
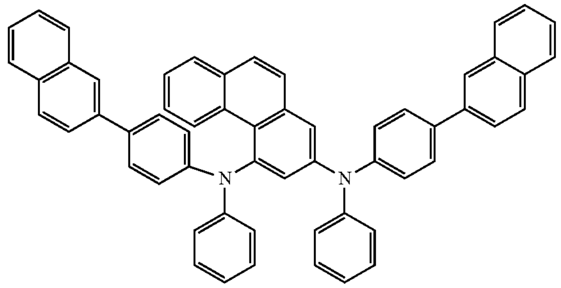
A-6
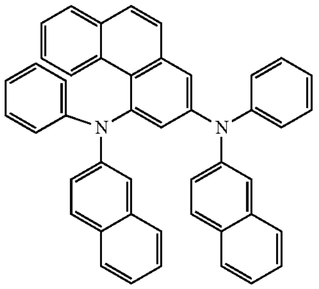
A-7
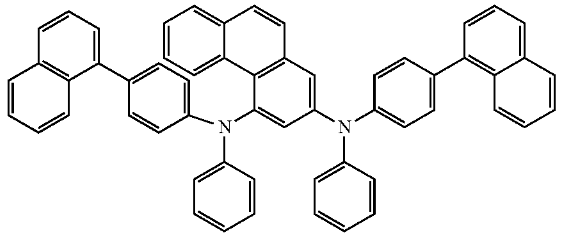
A-8
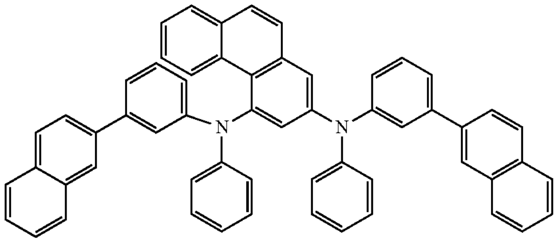
A-9
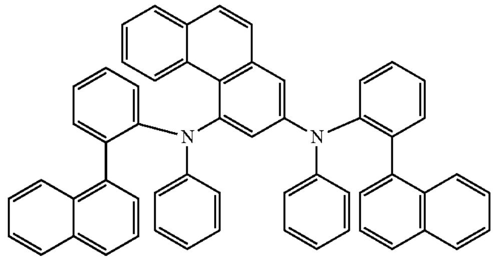
A-10
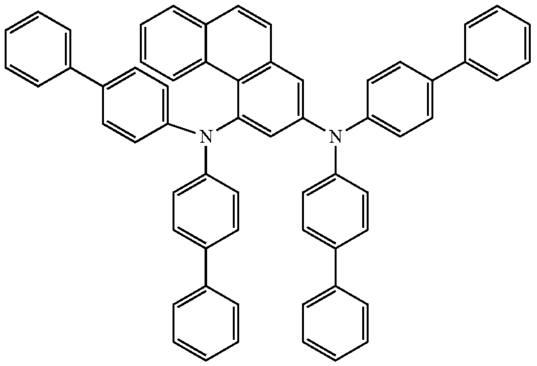
A-11
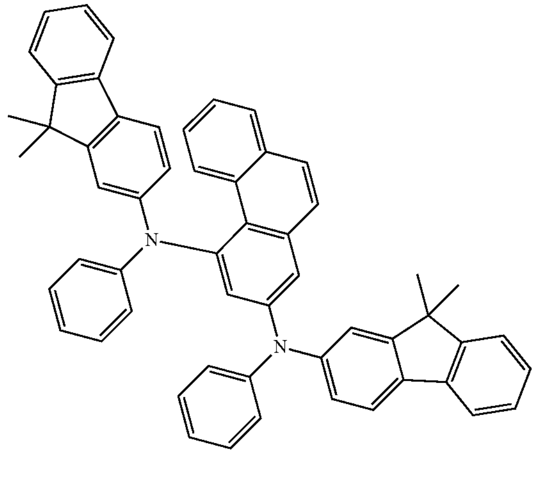

-continued
A-12
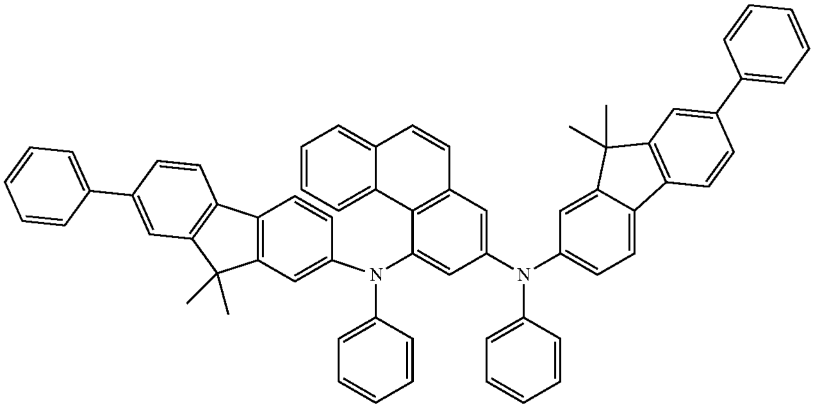
A-13
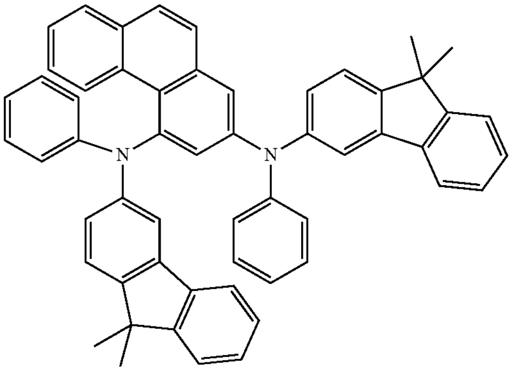
A-14
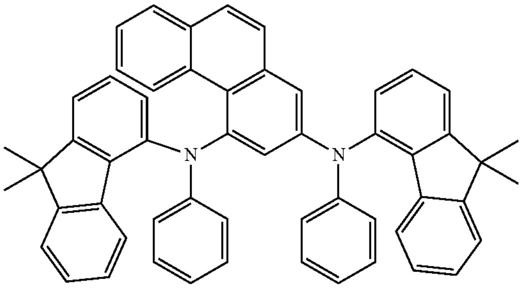
A-15
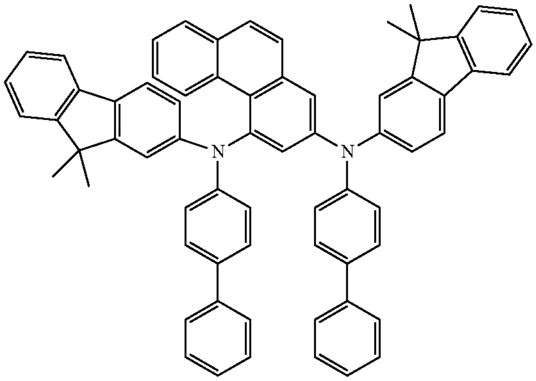
A-16
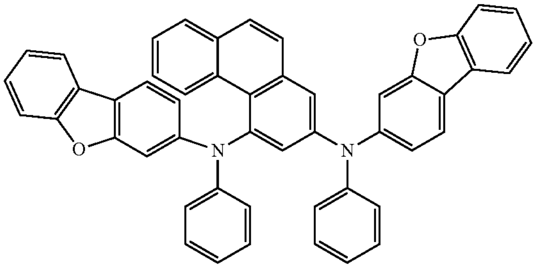
A-17
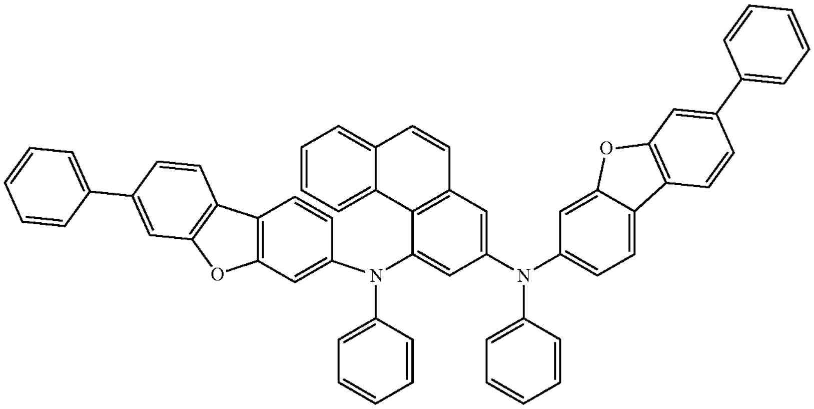

-continued
A-18
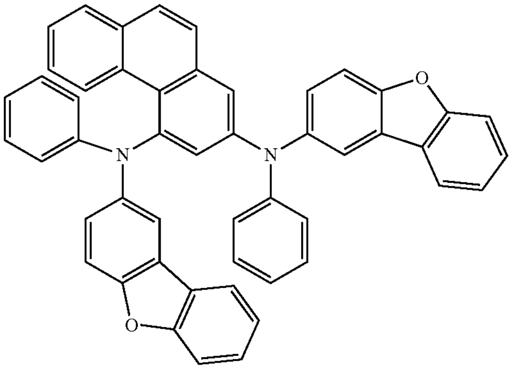
A-19
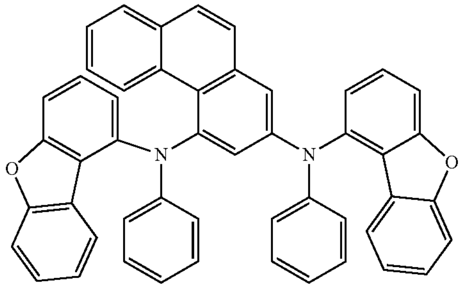
A-20
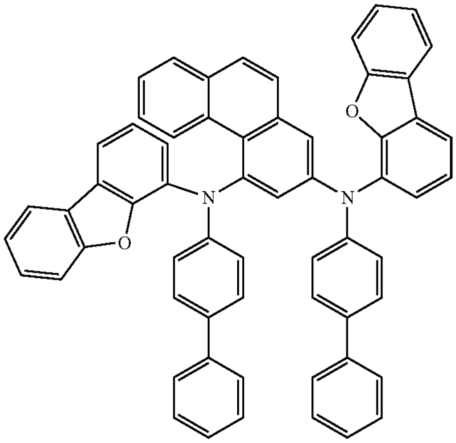
A-21
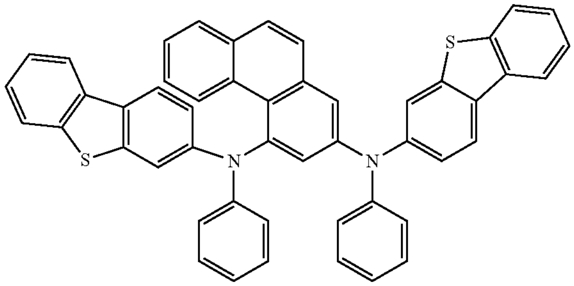
A-22
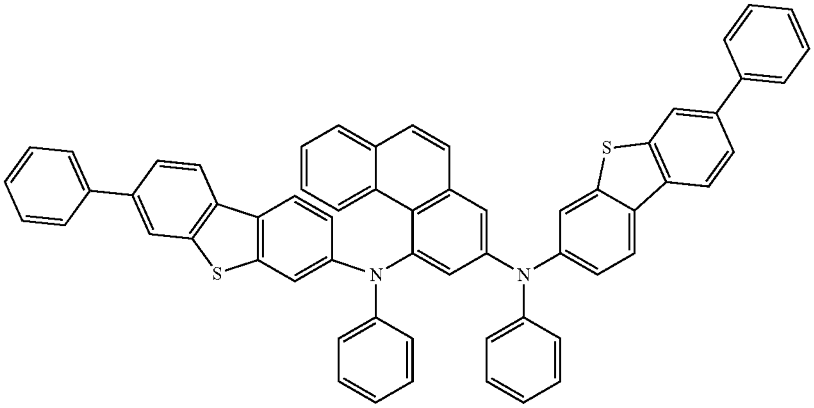
A-23
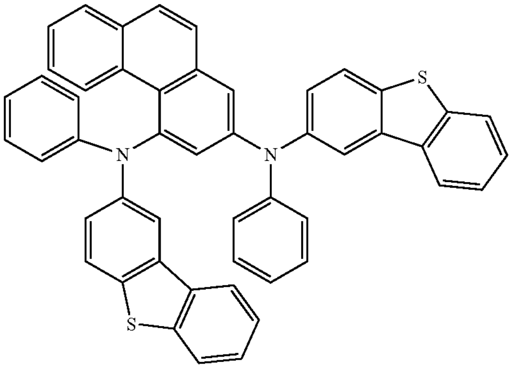
A-24
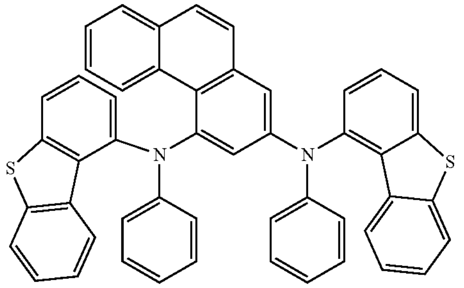

-continued
A-25
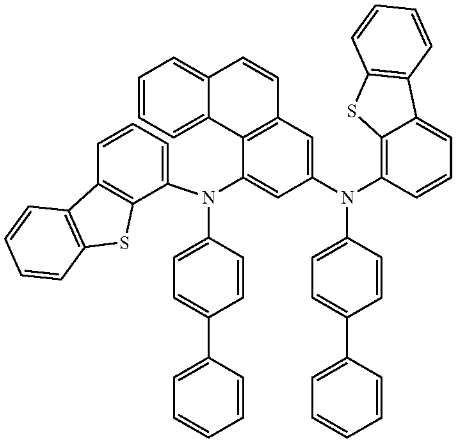
A-26
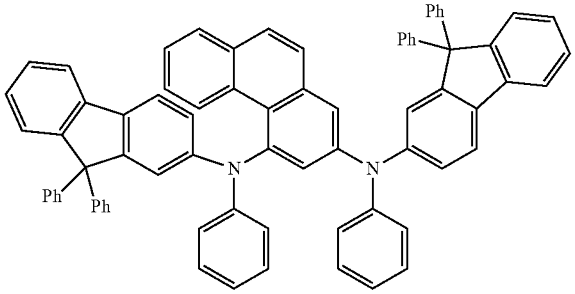
A-27
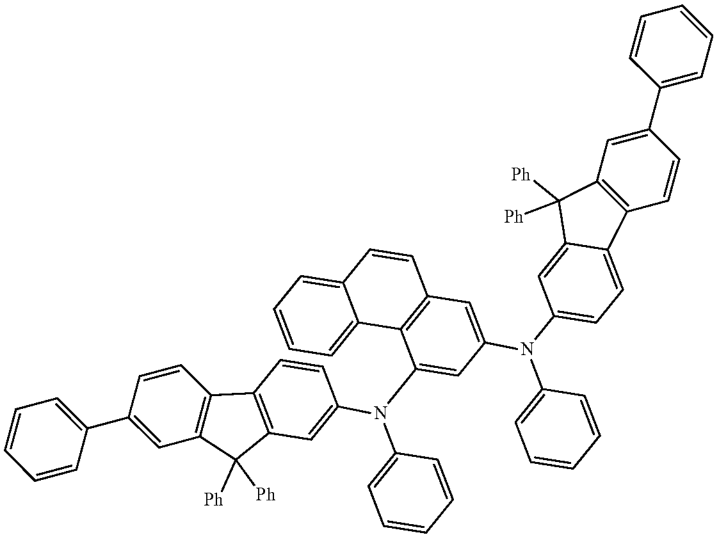
A-28
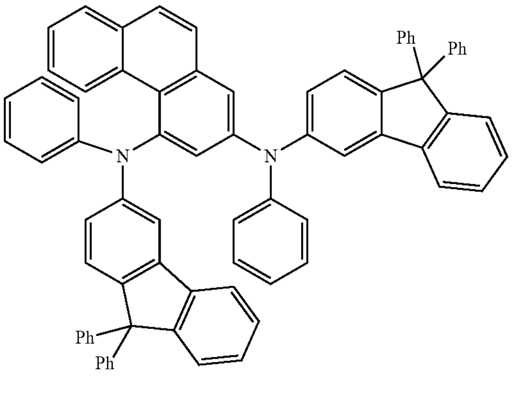
A-29
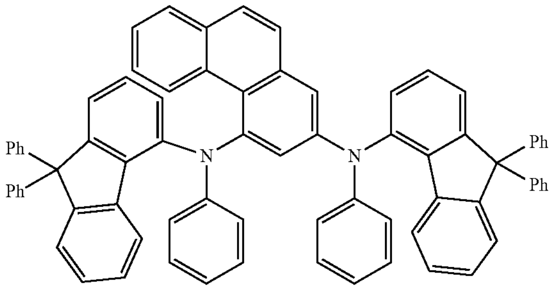

-continued
A-30
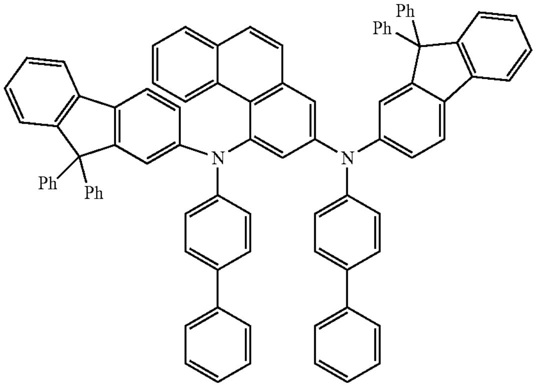
A-31
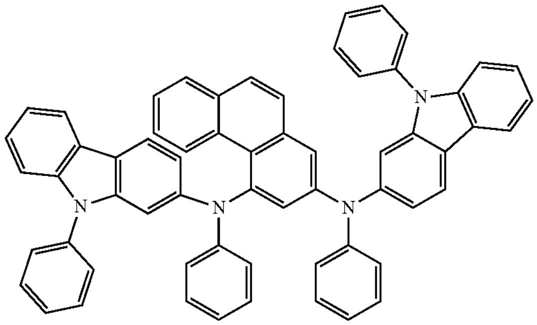
A-32
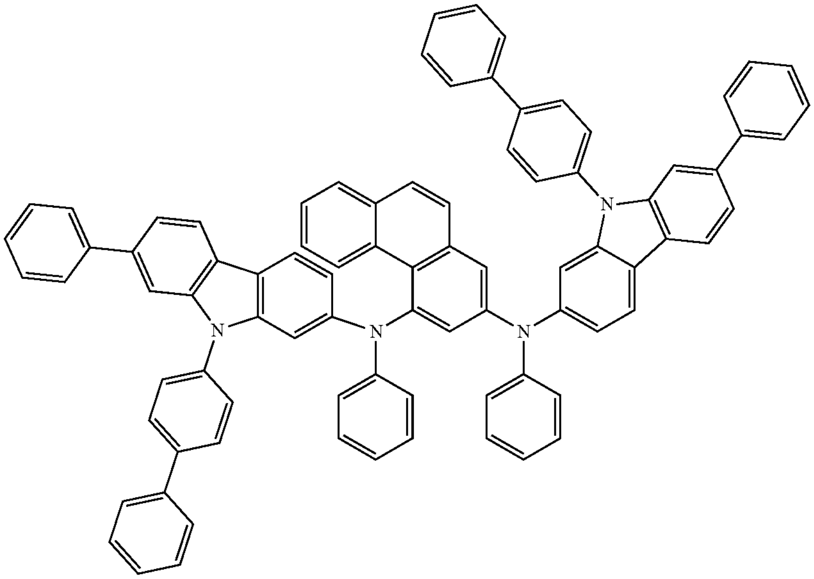
A-33
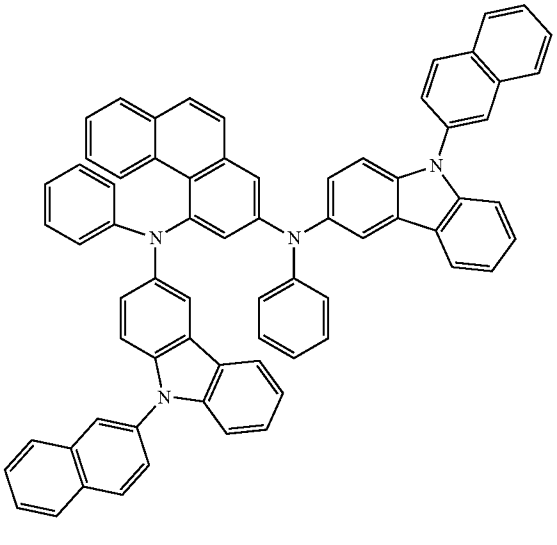
A-34
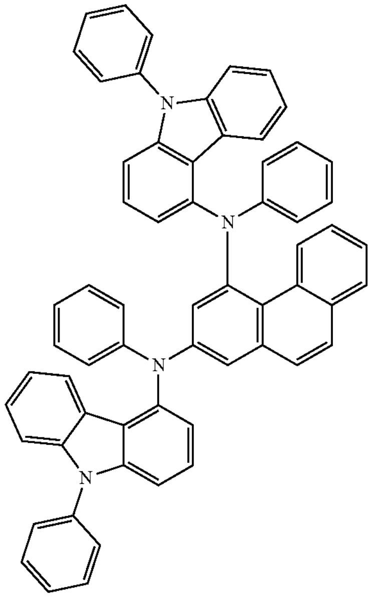

-continued
A-35
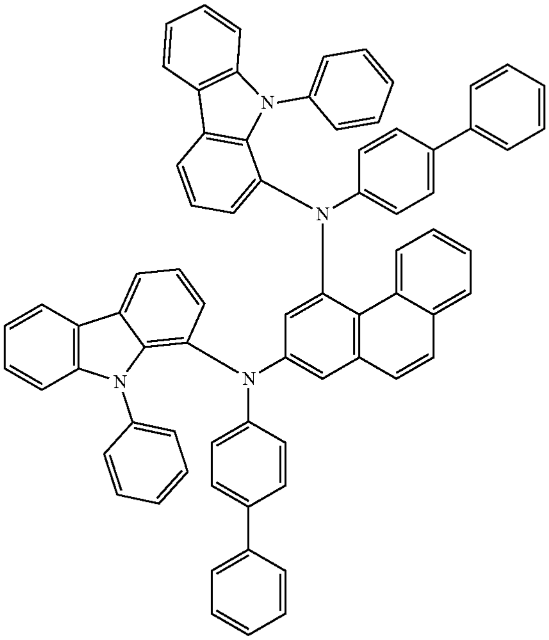
A-36
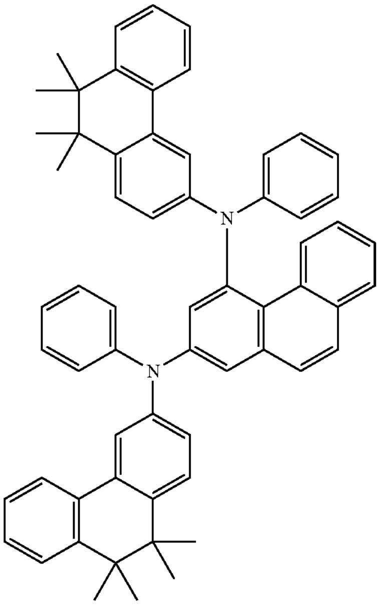
A-37
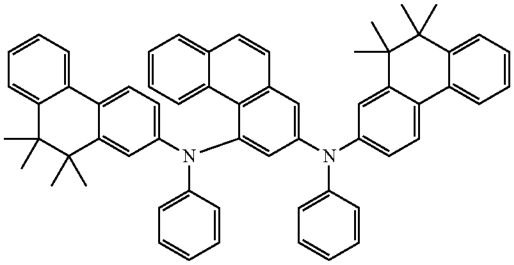
A-38
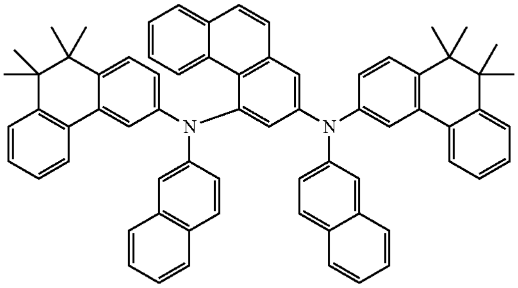
A-39
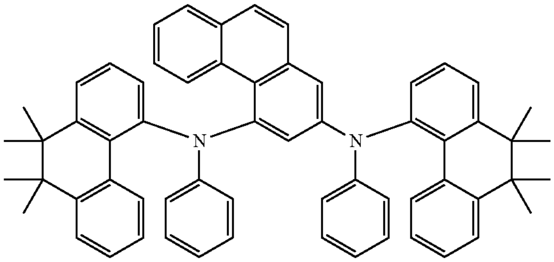
A-40
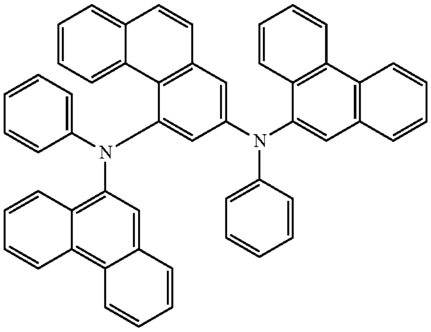

-continued
A-41
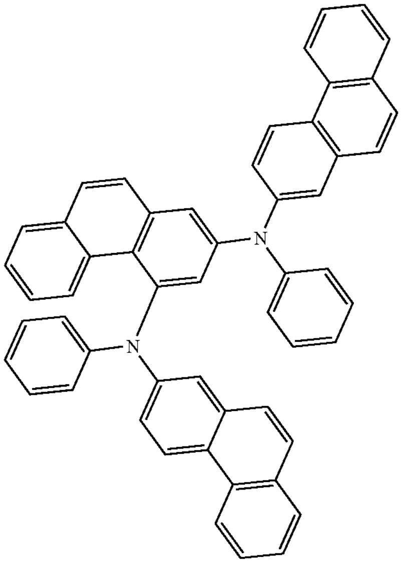
A-42
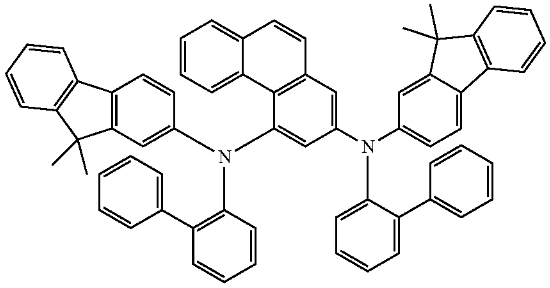
A-43
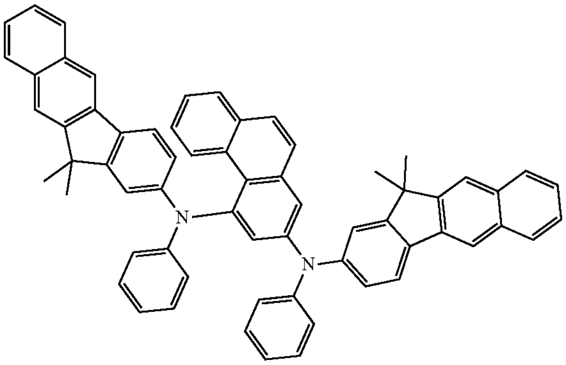
A-44
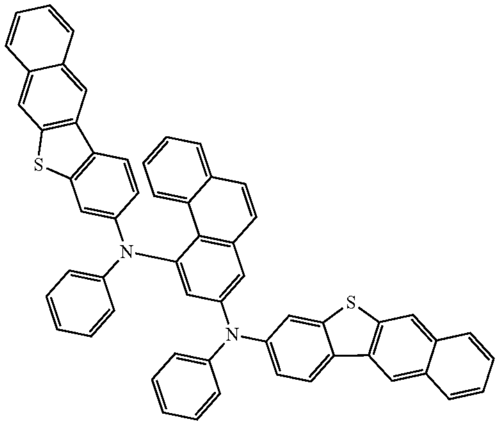
A-45
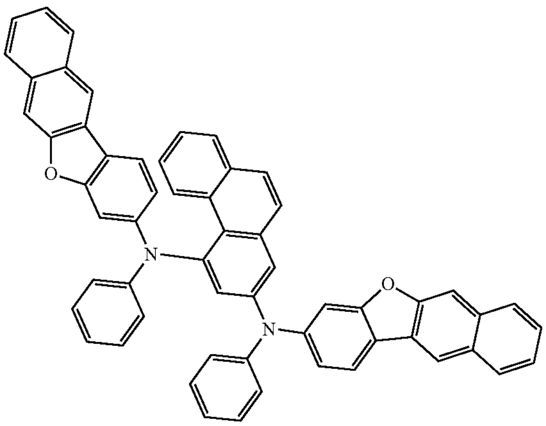
A-46
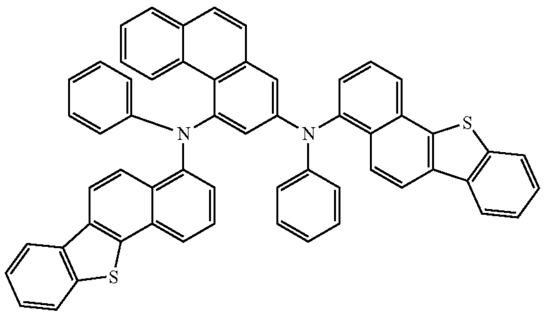

-continued
A-47
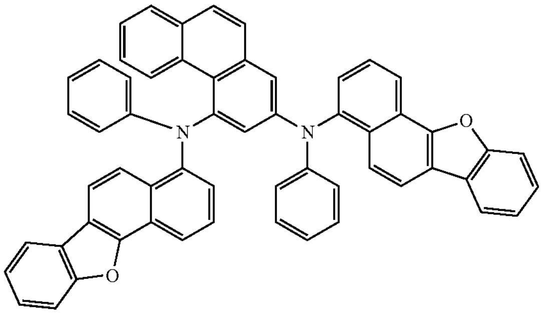
A-48
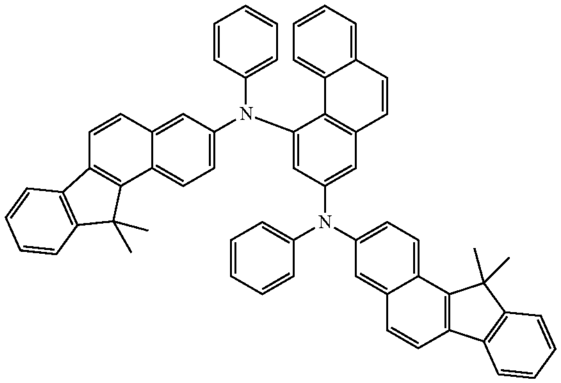
A-49
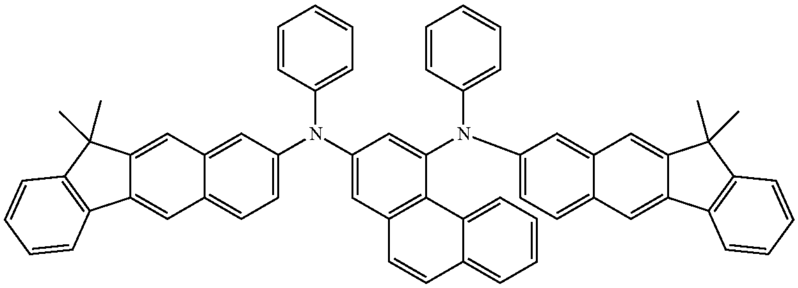
A-50
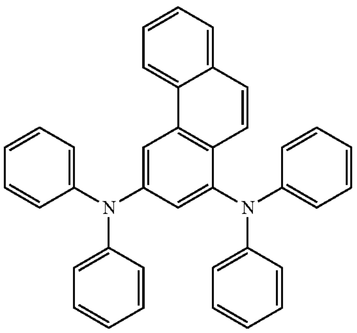
A-51
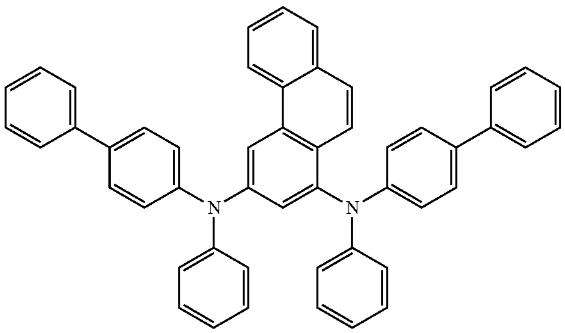
A-52
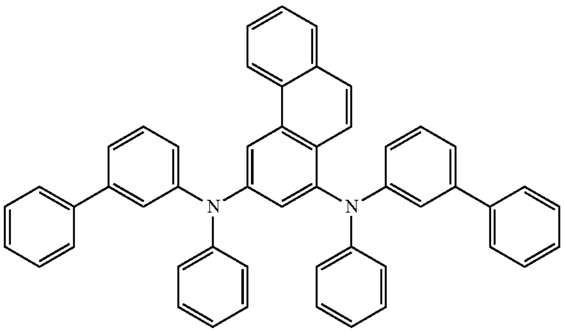
A-53
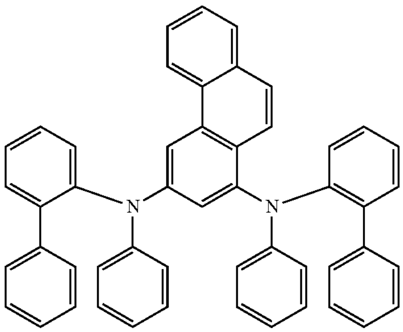

-continued
A-54
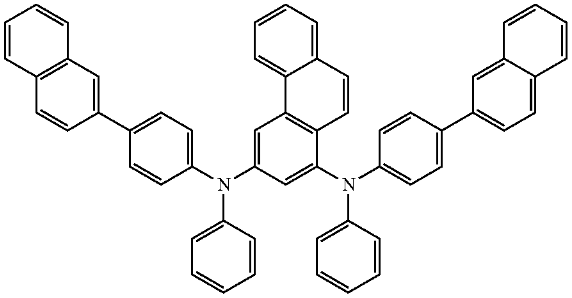
A-55
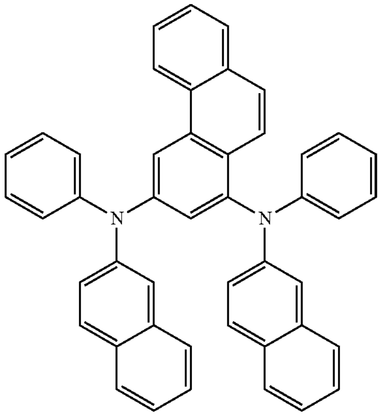
A-56
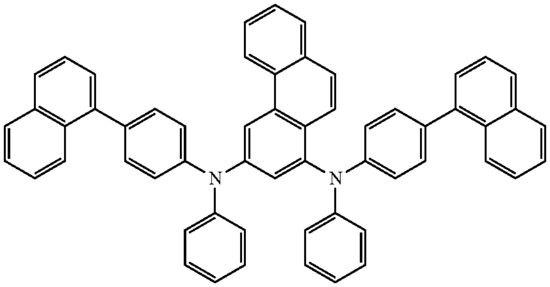
A-57
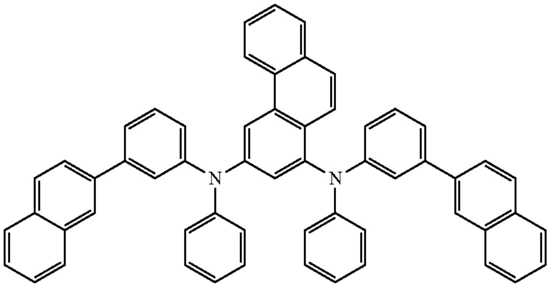
A-58
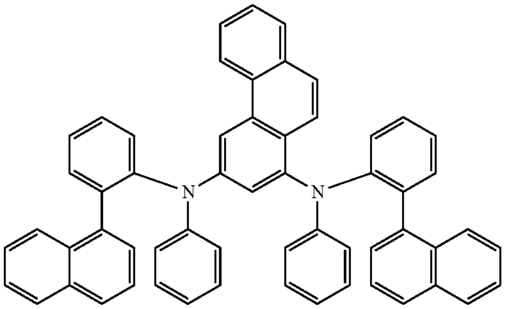
A-59
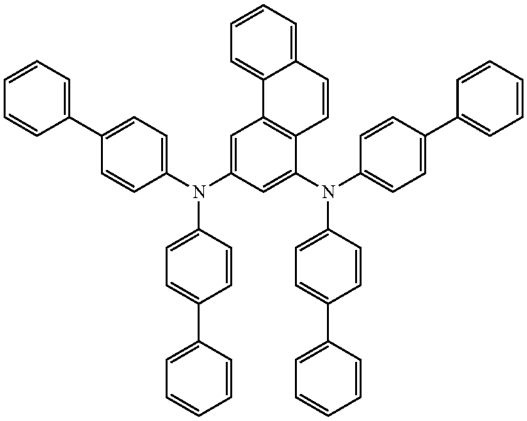
A-60
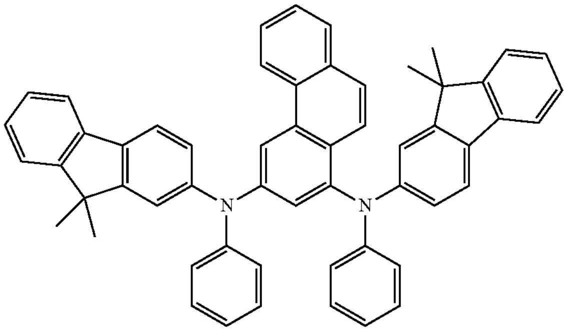

-continued
A-61
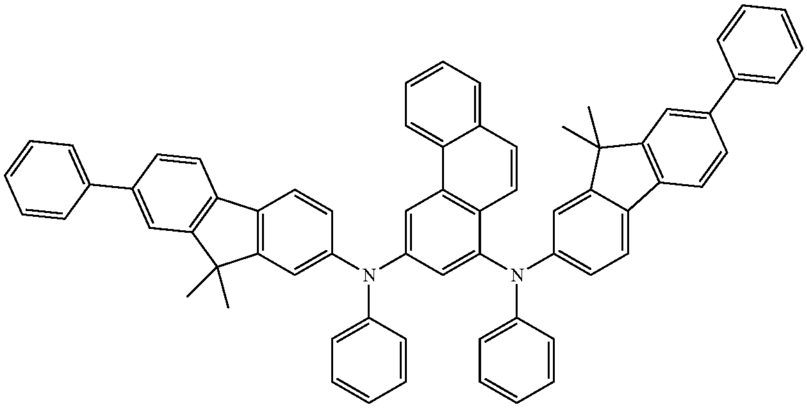
A-62
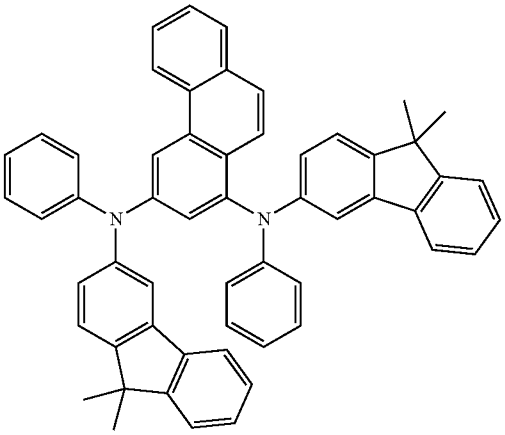
A-63
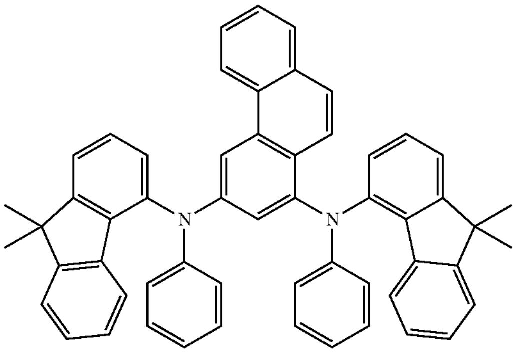
A-64
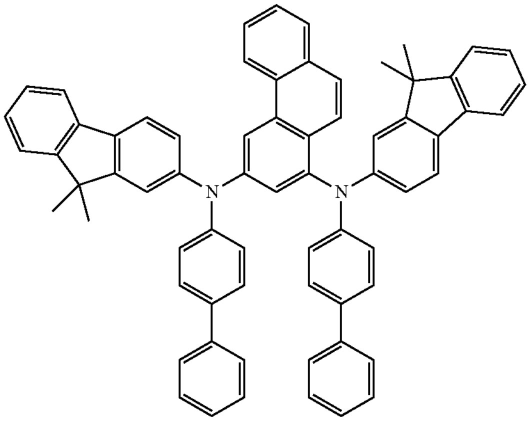
A-65
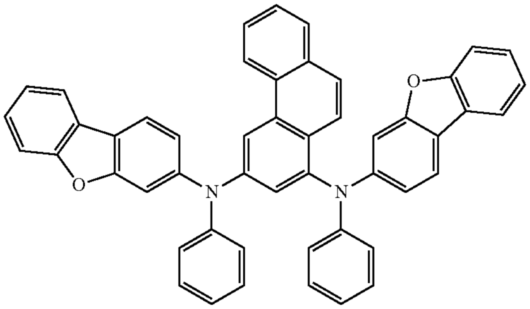

-continued
A-66
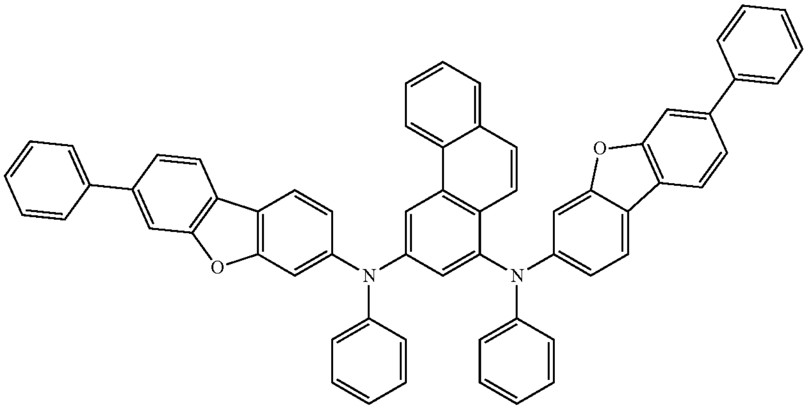
A-67
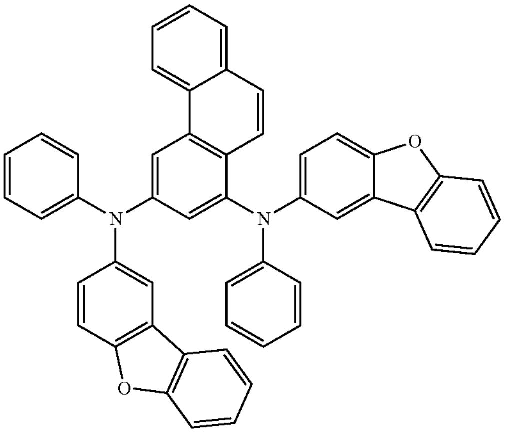
A-68
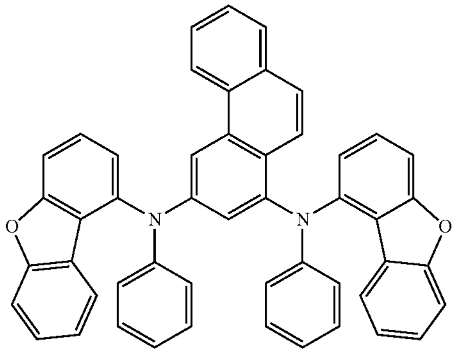
A-69
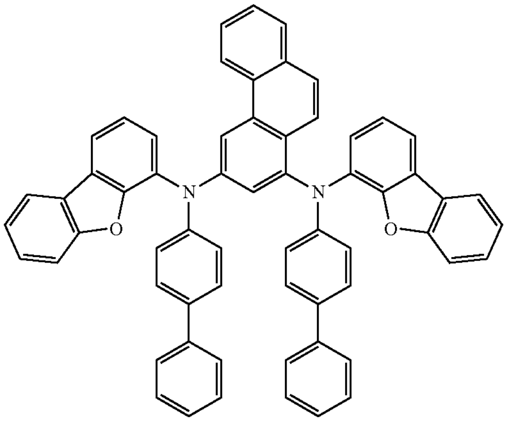
A-70
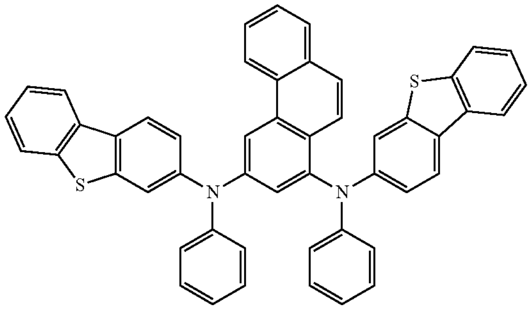

-continued
A-71
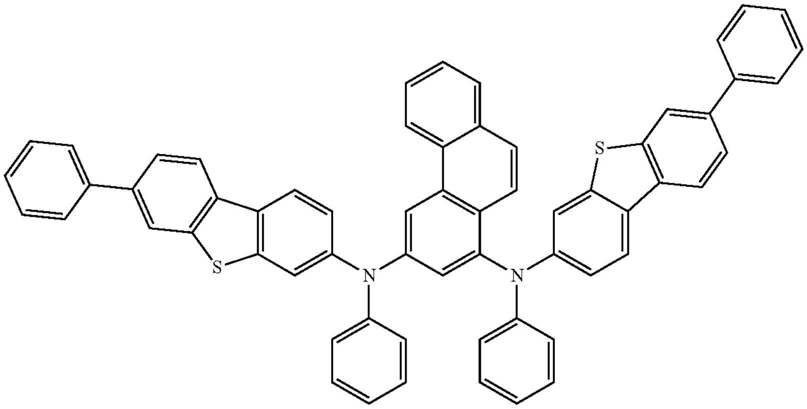
A-72
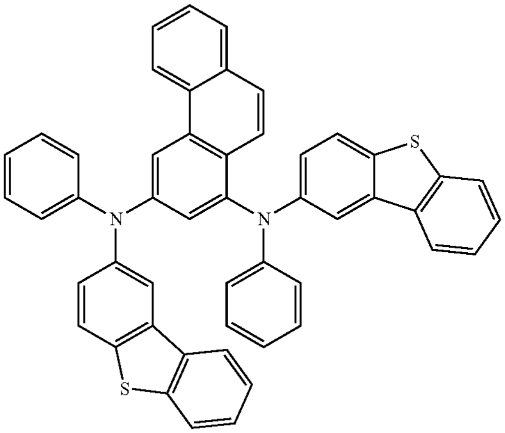
A-73
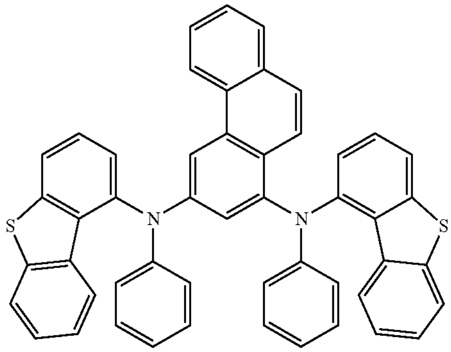
A-74
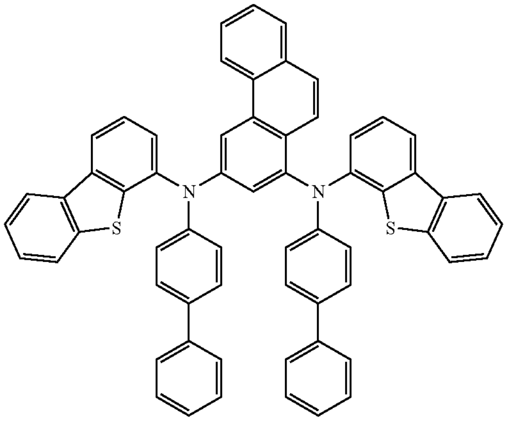
A-75
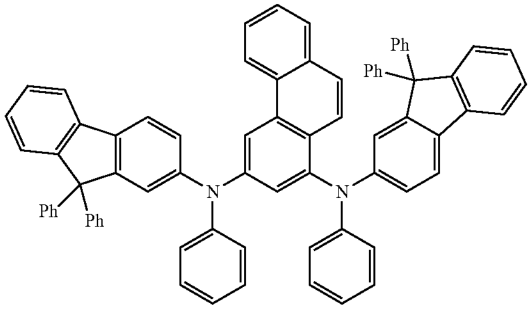

-continued
A-76
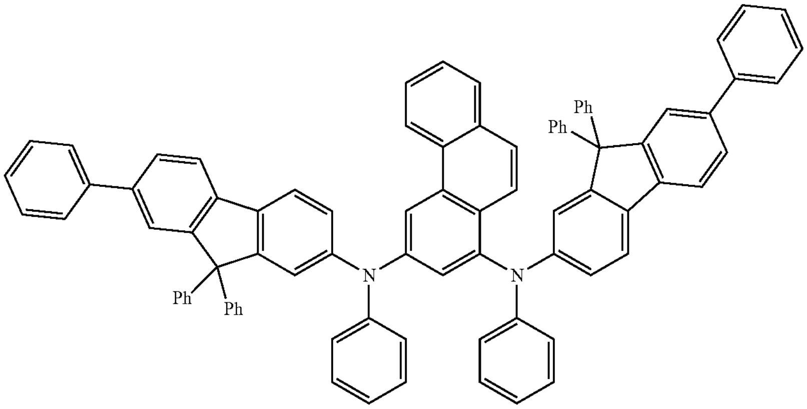
A-77
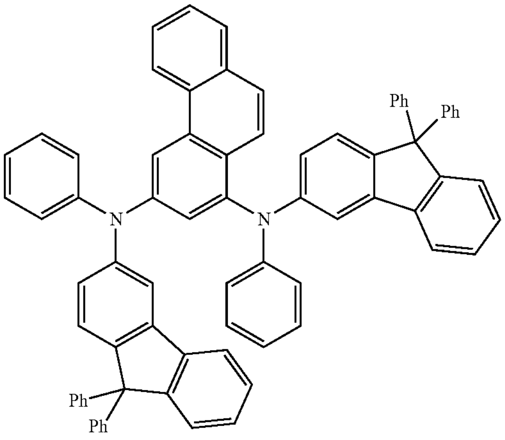
A-78
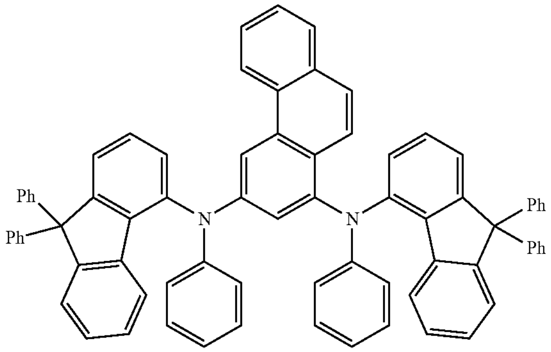
A-79
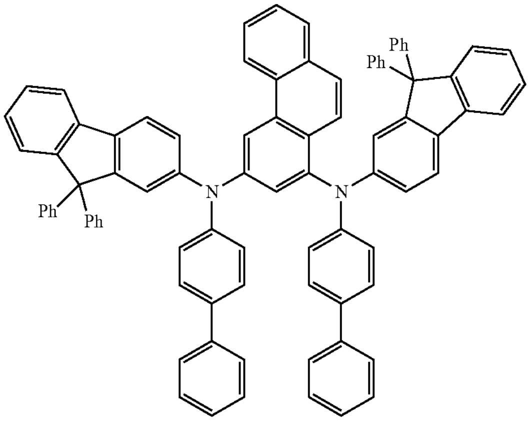
A-80
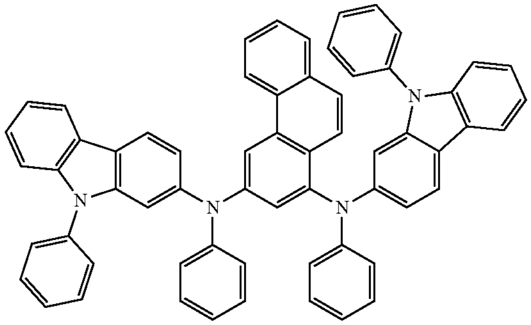

-continued
A-81
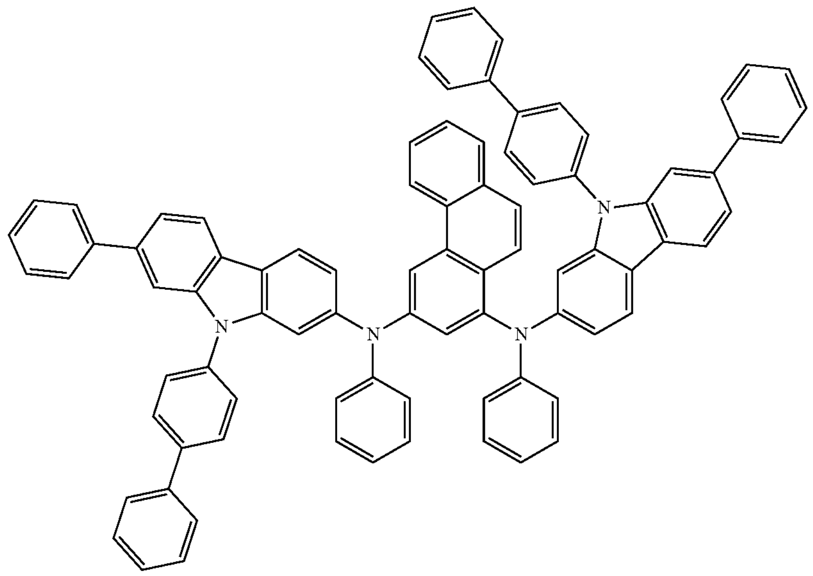
A-82
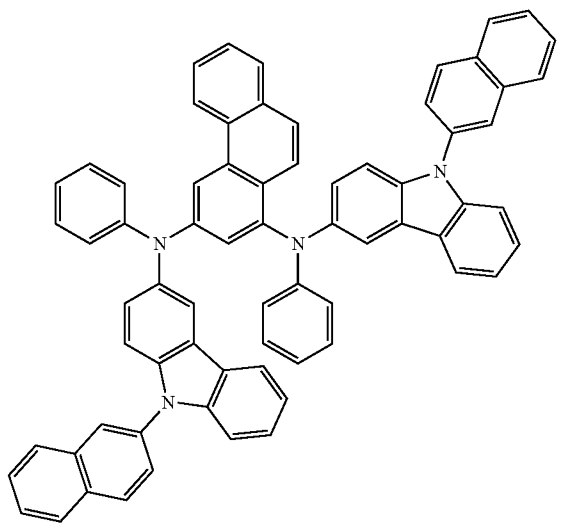
A-83
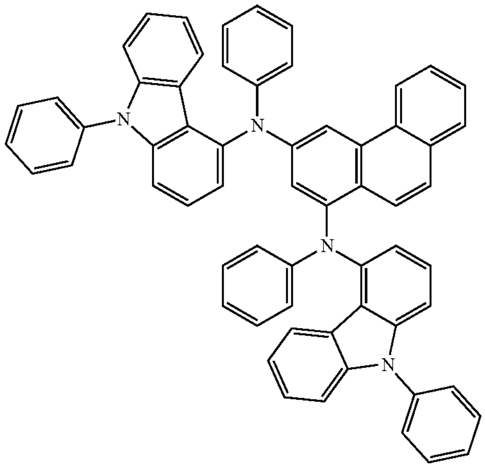

-continued
A-84
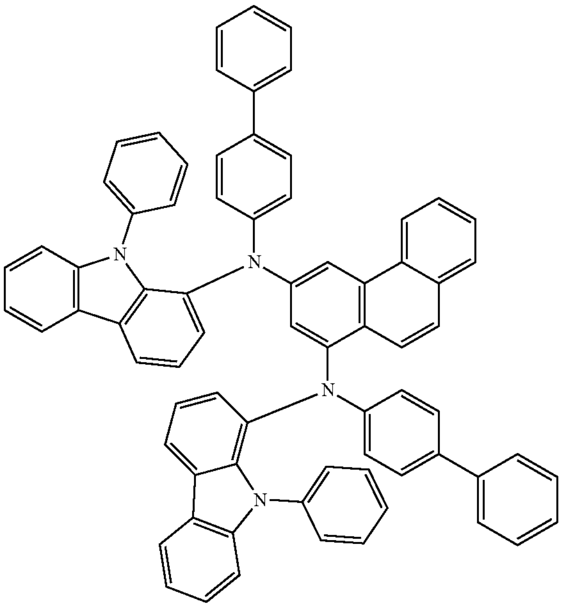
A-85
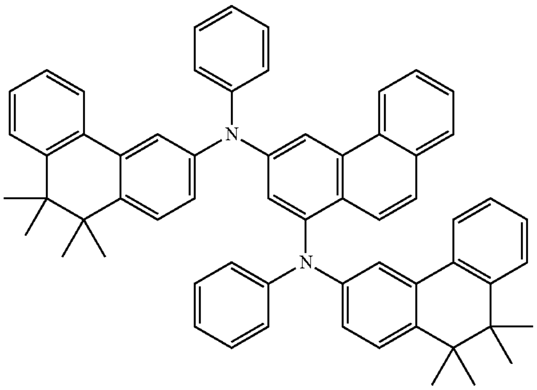
A-86
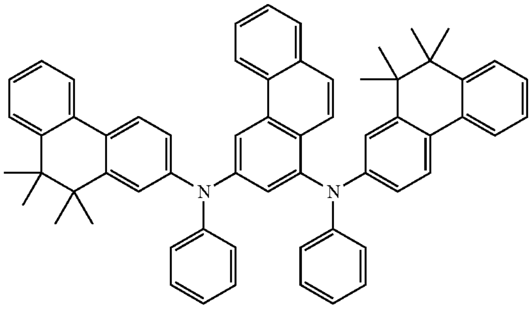
A-87
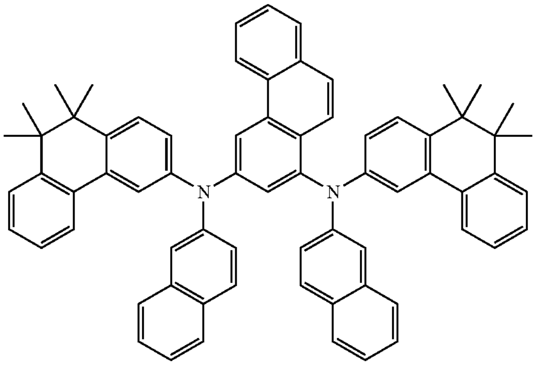
A-88
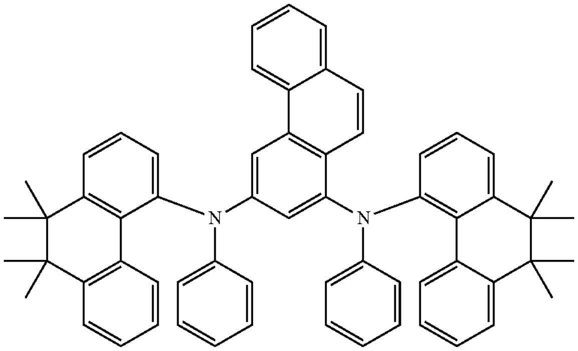
A-89
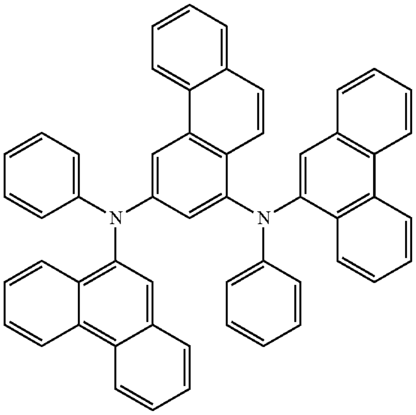

-continued
A-90
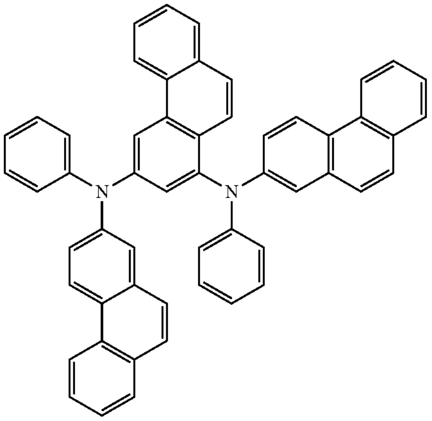
A-91
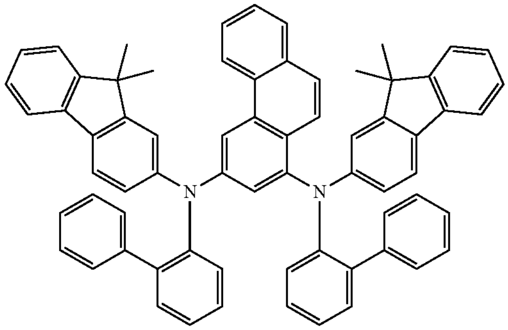
A-92
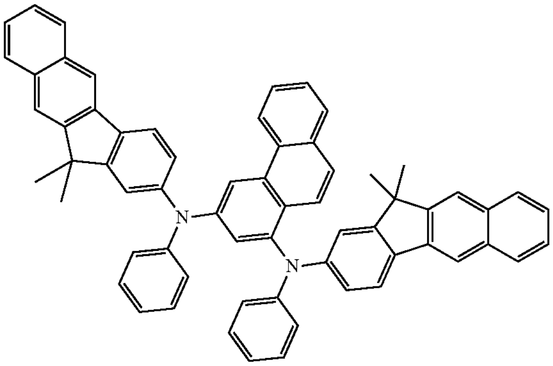
A-93
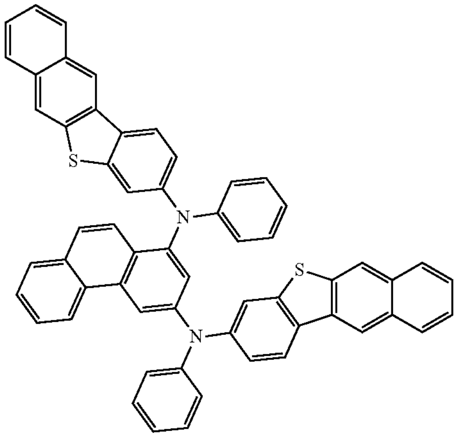
A-94
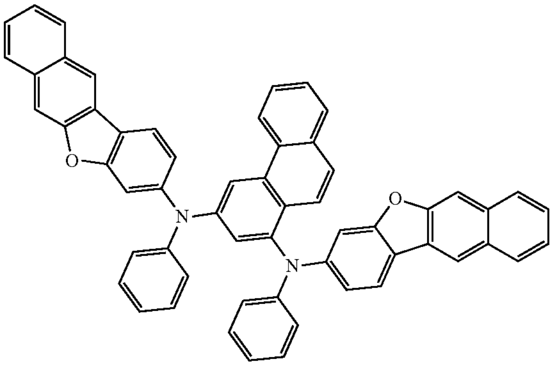
A-95
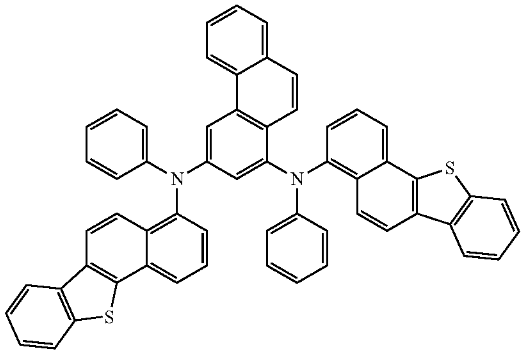

-continued
A-96
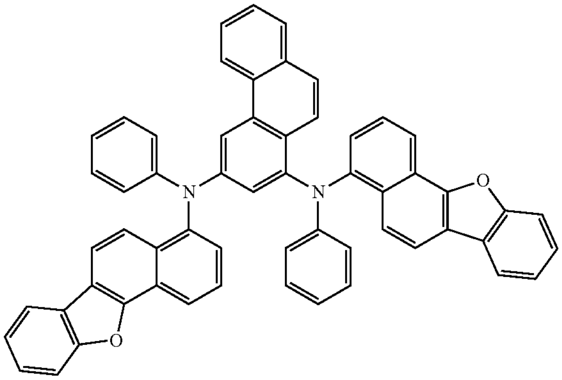
A-97
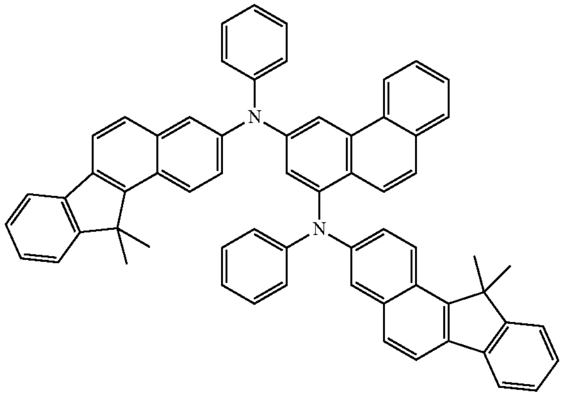
A-98
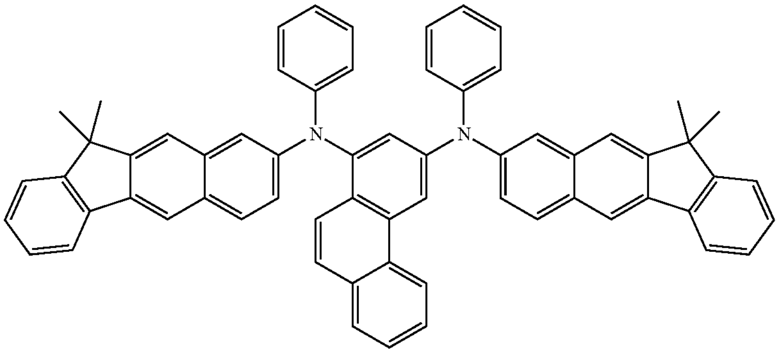
A-99
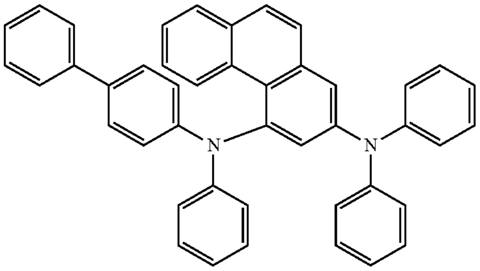
A-100
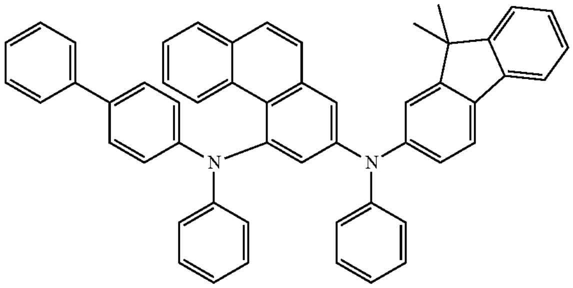
A-101
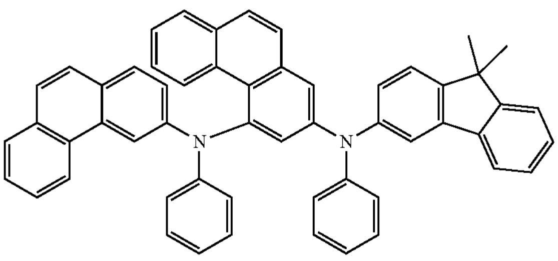
A-102
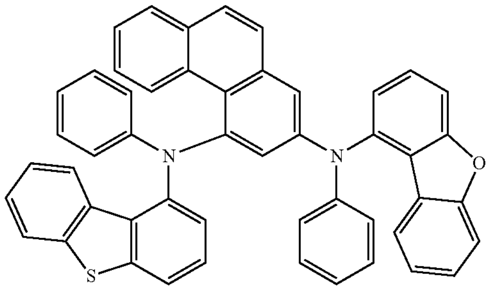

-continued
A-103
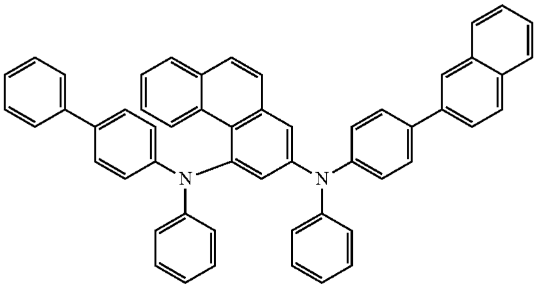
A-104
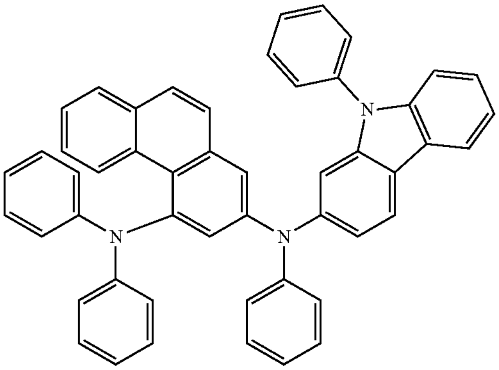
A-105
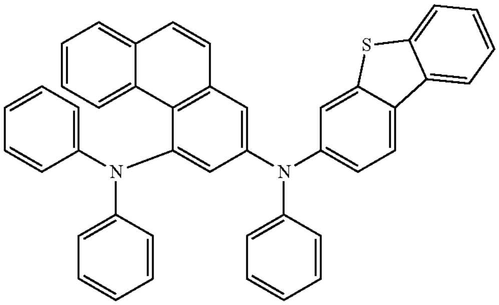
A-106
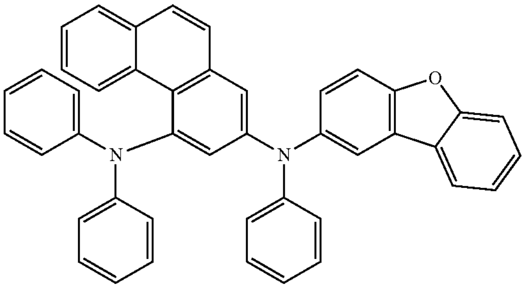
A-107
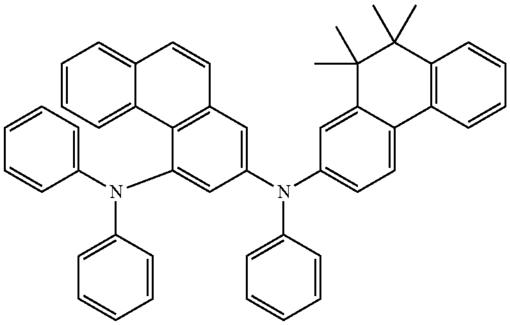
A-108
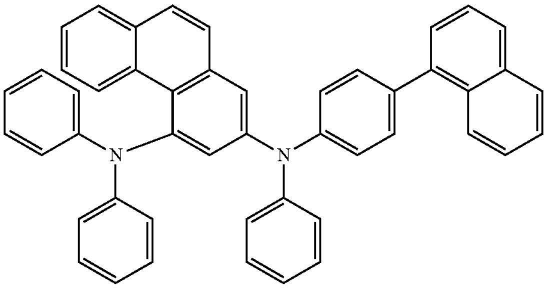
A-109
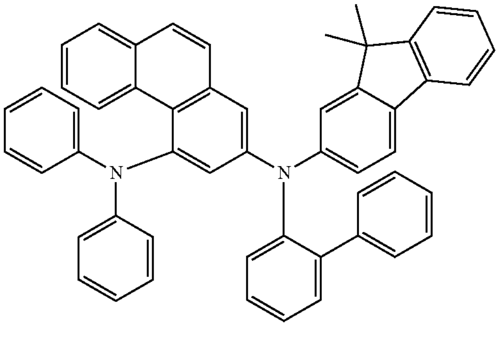
A-110
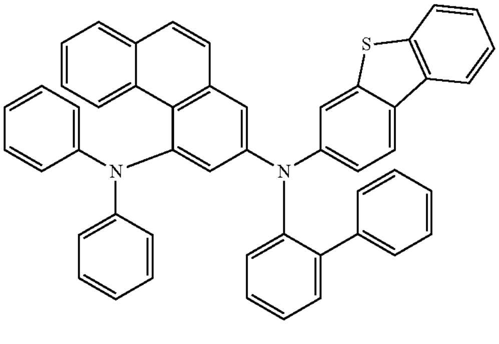

-continued
A-111
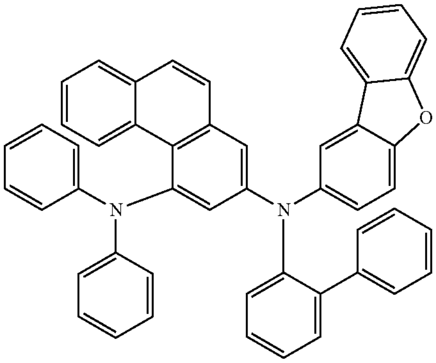
A-112
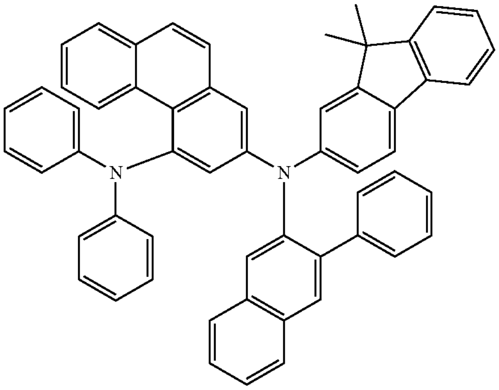
A-113
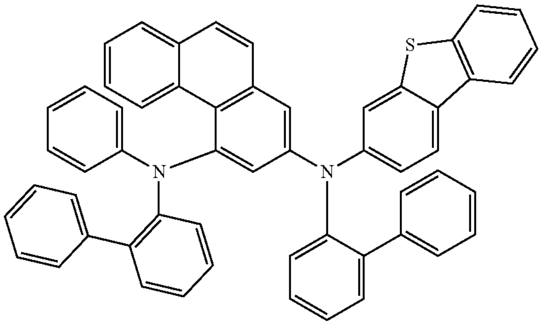
A-114
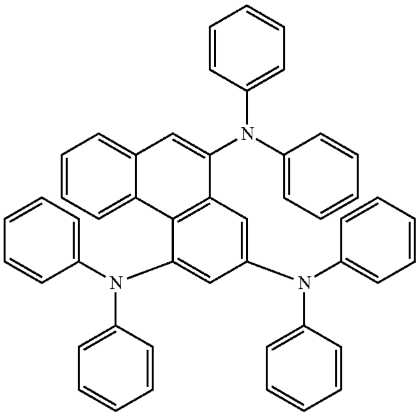
A-115
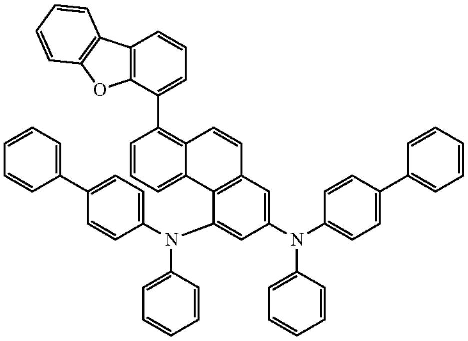
A-116
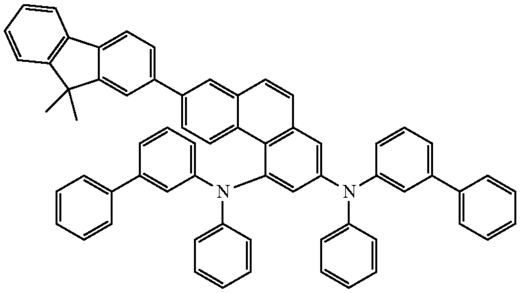
A-117
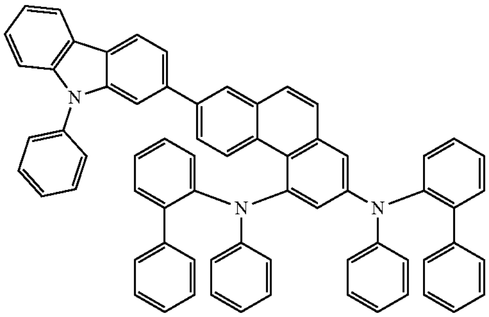
A-118
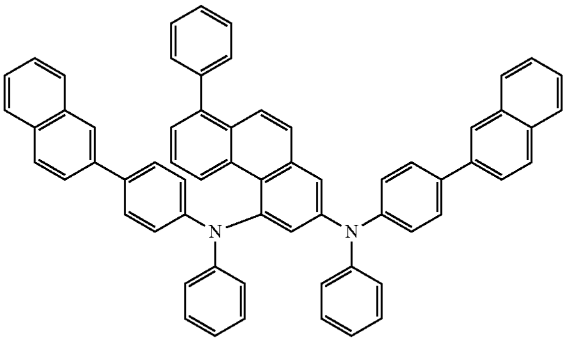

-continued
A-119
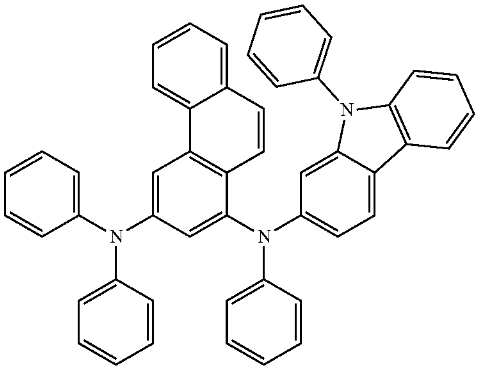
A-120
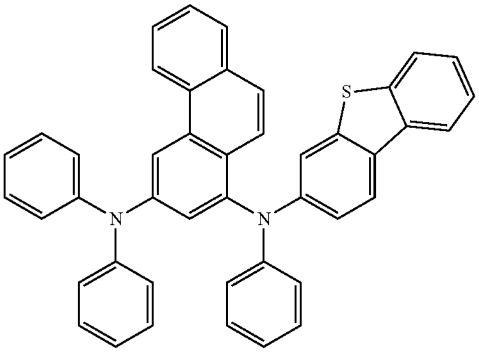
A-121
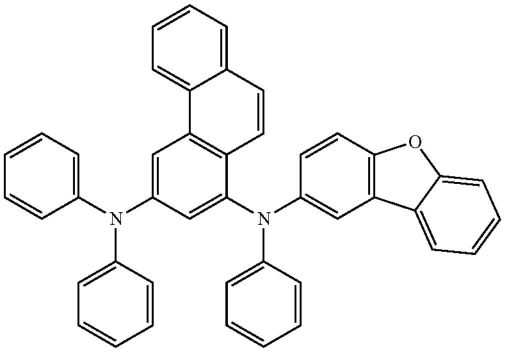
A-122
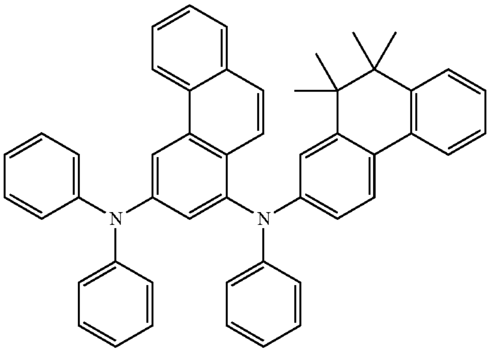
A-123
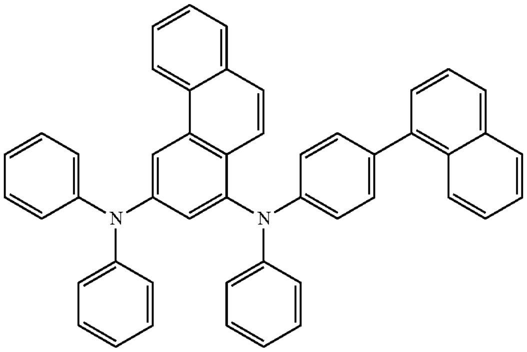
A-124
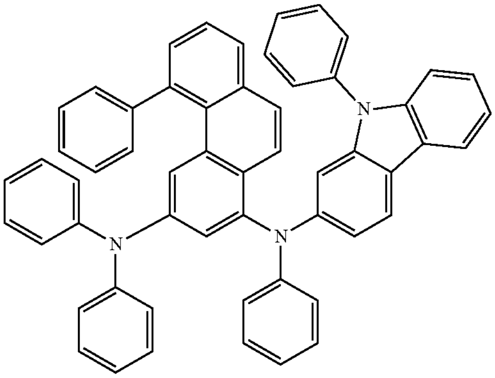
A-125
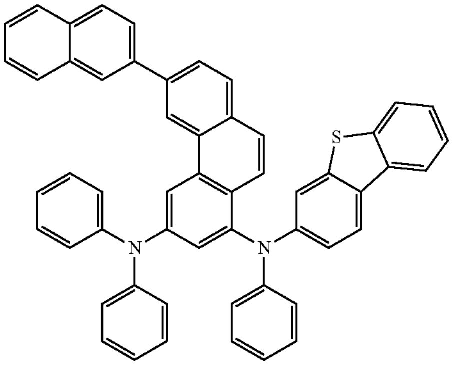
A-126
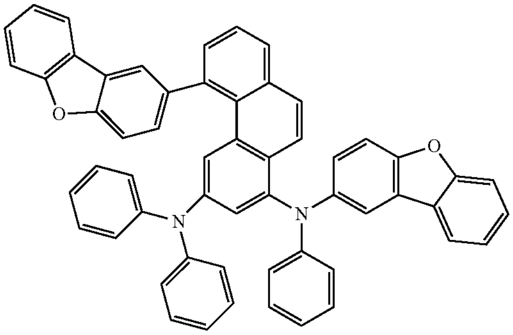

-continued
A-127
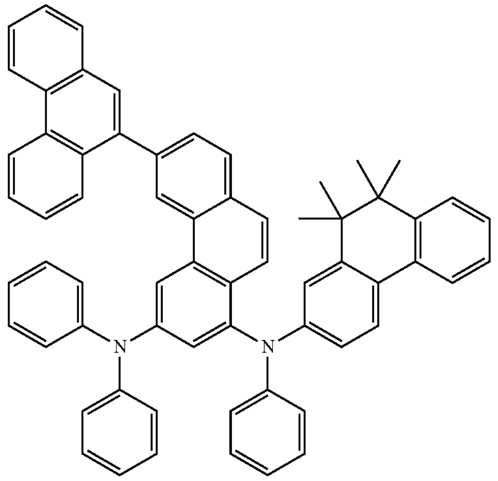
A-128
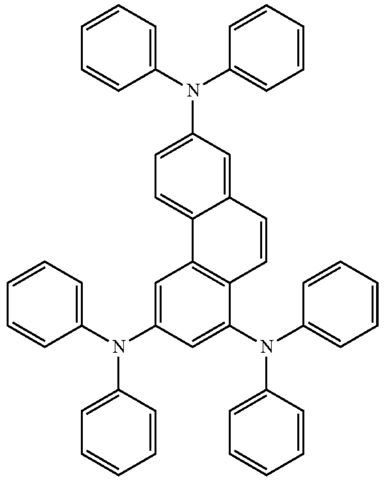
A-129
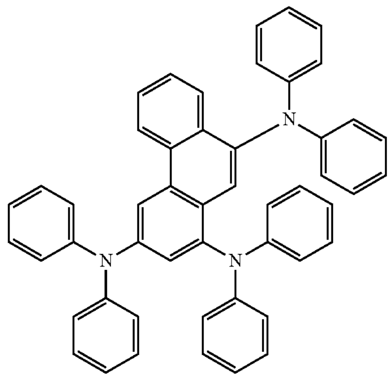
A-130
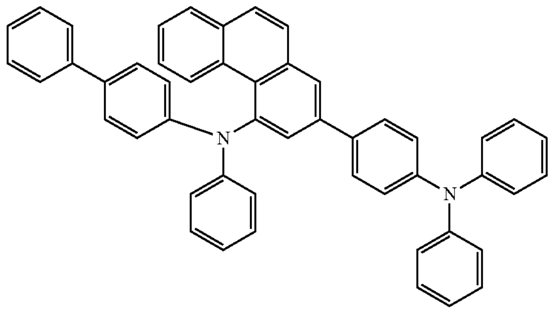
A-131
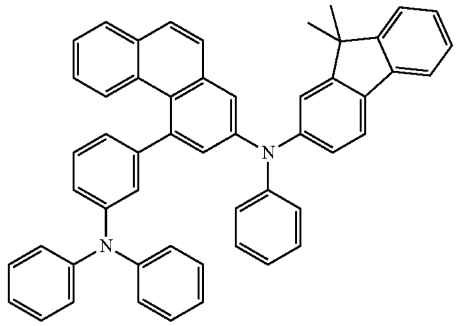
A-132
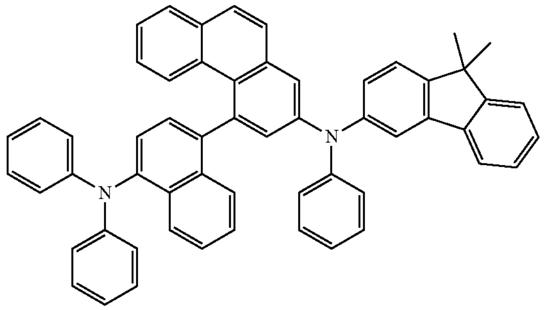
A-133
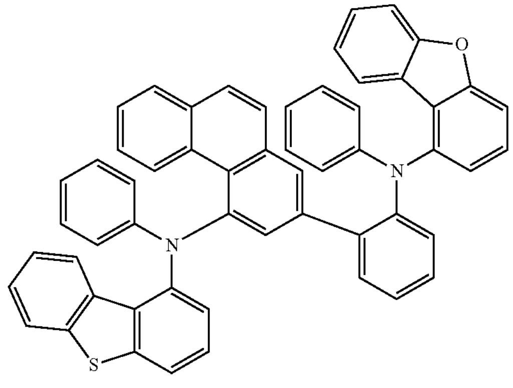
A-134
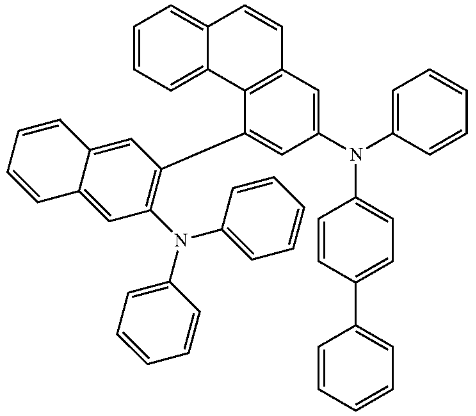

-continued
A-135
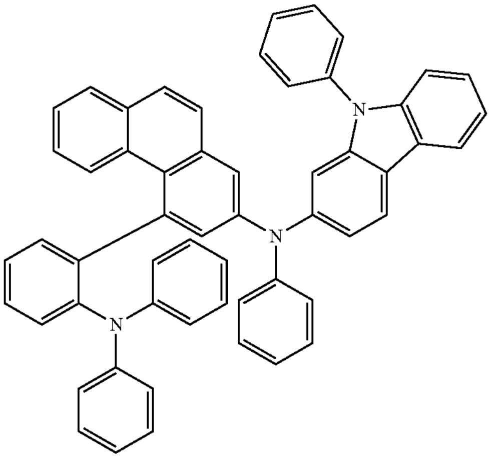
A-136
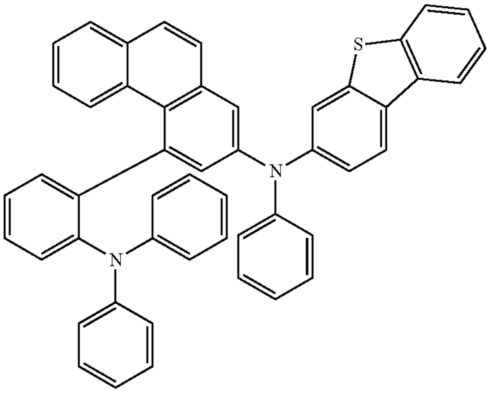
A-137
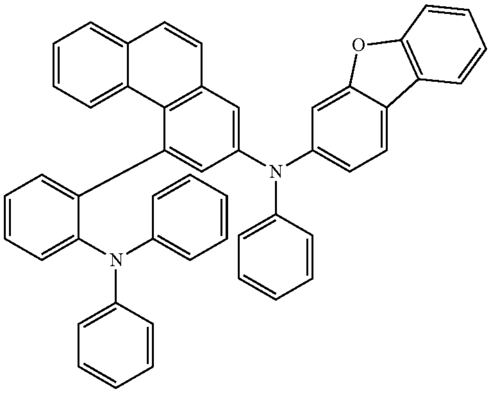
A-138
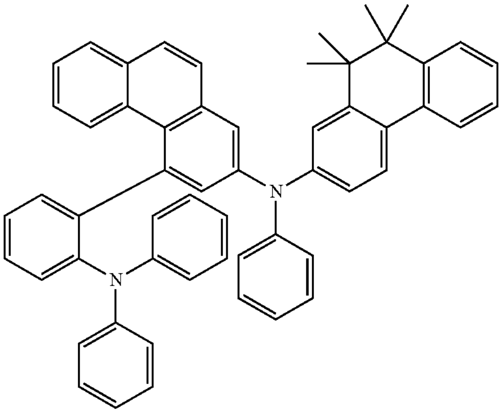
A-139
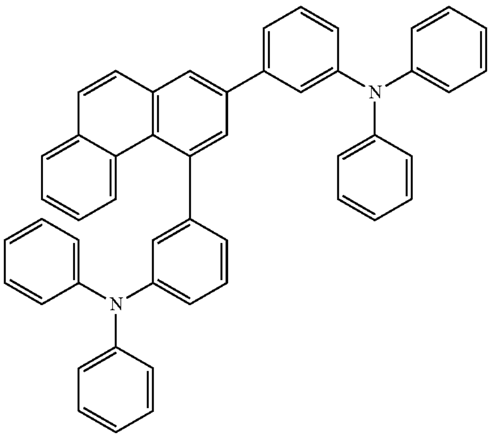

The compound of formula 1 according to the present disclosure may be prepared by a synthetic method known to one skilled in the art, for example, may be prepared as shown in the following reaction schemes 1 to 3, but is not limited thereto.

[Reaction Scheme 1]

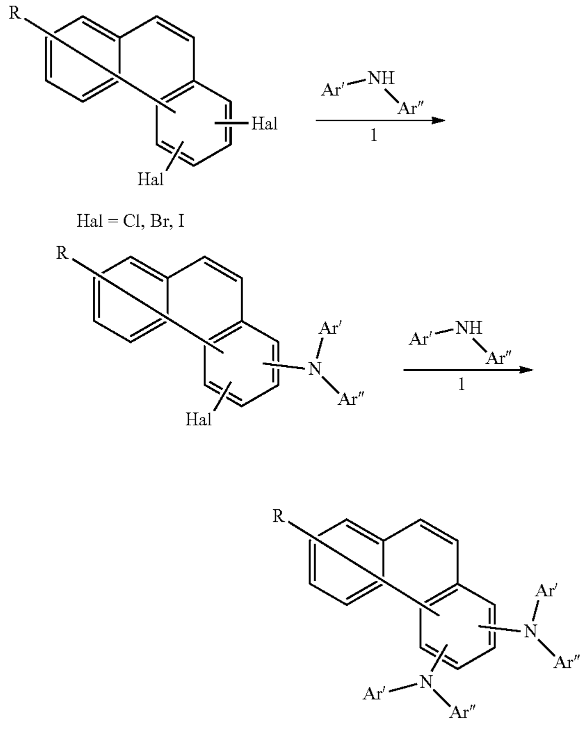

[Reaction Scheme 2]

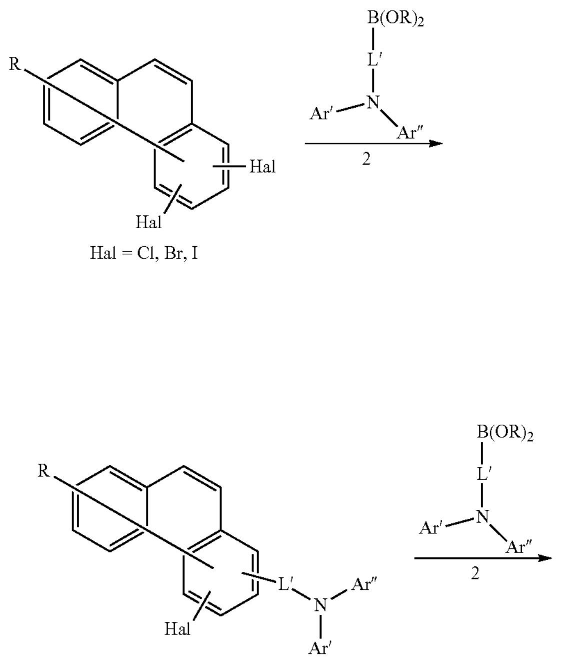

-continued

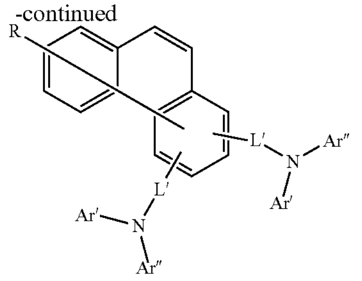

[Reaction Scheme 3]

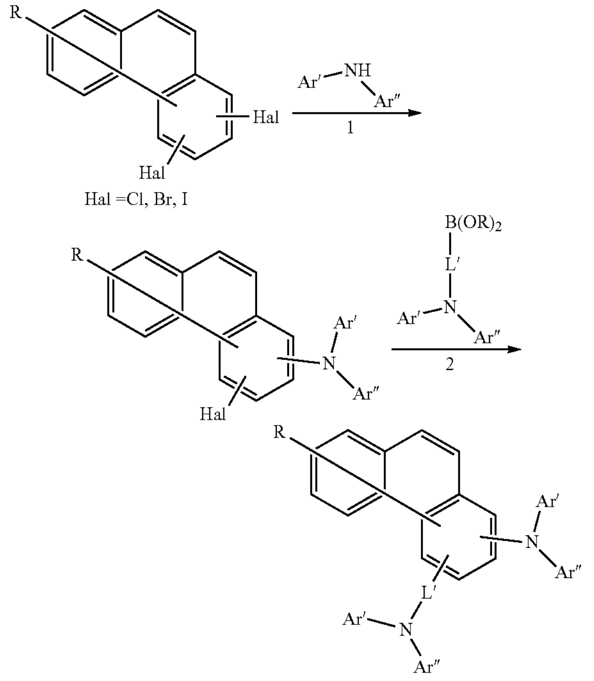

In reaction schemes 1 to 3, L', Ar', and Ar" are as defined in formula 1, and R is as $R_1$ and $R_2$ defined in formula 1.

Although illustrative synthesis examples of the compounds represented by formula 1 are described above, one skilled in the art will be able to readily understand that all of them are based on a Buchwald-Hartwig cross-coupling reaction, an N-arylation reaction, H-mont-mediated etherification reaction, a Miyaura borylation reaction, a Suzuki cross-coupling reaction, an intramolecular acid-induced cyclization reaction, a Pd(II)-catalyzed oxidative cyclization reaction, a Grignard reaction, a Heck reaction, a Cyclic Dehydration reaction, an $SN_1$ substitution reaction, an $SN_2$ substitution reaction, a Phosphine-mediated reductive cyclization reaction, etc., and the reactions above proceed even when substituents, which are defined in formula 1 but are not specified in the specific synthesis examples, are bonded.

The hole transport zone of the present disclosure may be constituted with at least one layer from the group consisting of a hole transport layer, a hole injection layer, an electron blocking layer, a hole auxiliary layer, and a light-emitting auxiliary layer, and each layer may consist of one or more layers.

According to one embodiment of the present disclosure, the hole transport zone comprises a hole transport layer. In addition, the hole transport zone comprises a hole transport layer, and may further comprise one or more layers of a hole injection layer, an electron blocking layer, a hole auxiliary layer, and a light-emitting auxiliary layer.

In addition, the present disclosure provides an organic electroluminescent material comprising the organic electroluminescent compound of formula 1, and an organic electroluminescent device comprising the material.

The material may be a hole transport material, a hole auxiliary material, a light-emitting auxiliary material, or an electron blocking material, for example, may be a hole transport material, a hole auxiliary material, a light-emitting auxiliary material, or an electron blocking material of a red light-emitting organic electroluminescent device, and may be a hole transport material (hole auxiliary material) comprised in a hole transport layer adjacent to a light-emitting layer if there are two or more layers in a hole transport layer.

The material may consists of the organic electroluminescent compound of the present disclosure alone, or may further comprise conventional materials included in the organic electroluminescent material.

The organic electroluminescent device according to the present disclosure has a first electrode; a second electrode; and at least one organic layer interposed between the first electrode and the second electrode, and the organic layer may comprise at least one organic electroluminescent compound of formula 1.

One of the first electrode and the second electrode may be an anode and the other may be a cathode. The organic layer includes a light-emitting layer, and may further include one or more layers selected from a hole injection layer, a hole transport layer, a hole auxiliary layer, a light-emitting auxiliary layer, an electron transport layer, an electron buffer layer, an electron injection layer, an interlayer, a hole blocking layer, and an electron blocking layer.

The first electrode and the second electrode may each be formed with a transparent conductive material, a transflective conductive material, or a reflective conductive material. The organic electroluminescent device may be a top emission type, a bottom emission type, or both-sides emission type according to the kinds of the material forming the first electrode and the second electrode. In addition, the hole injection layer may be further doped with a p-dopant, and the electron injection layer may be further doped with an n-dopant.

According to one embodiment of the present disclosure, the organic electroluminescent device of the present disclosure may further include an azine-based compound as at least one of an electron transport material, an electron injection material, an electron buffer material, and a hole blocking material in addition to the organic electroluminescent compound of the present disclosure.

The organic electroluminescent compound represented by formula 1 of the present disclosure may be comprised in at least one layer of a light-emitting layer, a hole injection layer, a hole transport layer, a hole auxiliary layer, a light-emitting auxiliary layer, an electron transport layer, an electron buffer layer, an electron injection layer, an interlayer, a hole blocking layer, and an electron blocking layer. In some cases, preferably, it may be comprised in at least one of a hole transport layer, a hole auxiliary layer, or a light-emitting auxiliary layer. When there are two or more layers in a hole transport layer, it may be used for at least one of them. For example, when used in a hole transport layer, the organic electroluminescent compound of the present disclosure may be included as a hole transport material.

The light-emitting layer may comprise one or more host and one or more dopant. If necessary, the light-emitting layer may comprise a co-host material, i.e., two or more of plurality of host materials.

The host used in the present disclosure may be a phosphorescent host compound or fluorescent host compound, but the host compounds are not limited thereto.

Dopants that can be comprised in the organic electroluminescent device of the present disclosure may be at least one phosphorescent or fluorescent dopant, preferably a phosphorescent dopant. The phosphorescent dopant materials applied to the organic electroluminescent device according to the present disclosure are not particularly limited, but may be selected from metallated complex compounds of iridium (Ir), osmium (Os), copper (Cu), and platinum (Pt), may be preferably selected from ortho-metallated complex compounds of iridium (Ir), osmium (Os), copper (Cu), and platinum (Pt), and may be more preferably an ortho-metallated iridium complex compound.

The dopant comprised in the organic electroluminescent device of the present disclosure may be the compound represented by the following formula 101, but is not limited thereto.

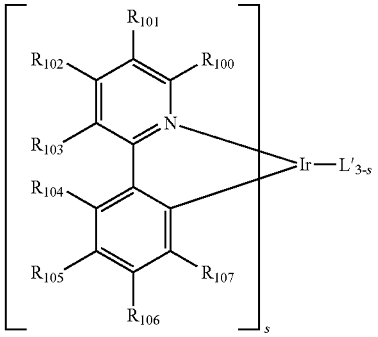

(101)

In formula 101,

L' is selected from the following structures 1 to 3:

[Structure 1]

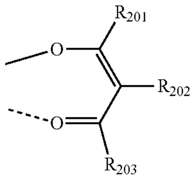

[Structure 2]

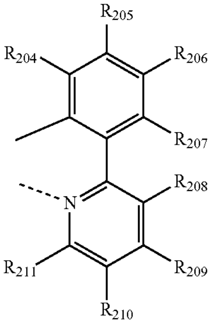

-continued

[Structure 3]

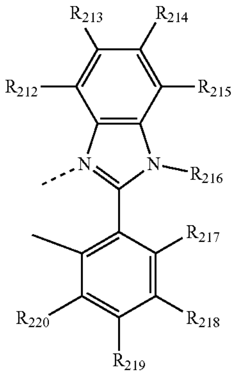

$R_{100}$ to $R_{103}$, each independently, represent hydrogen, deuterium, a halogen, a (C1-C30)alkyl unsubstituted or substituted with deuterium(s) and/or a halogen(s), a substituted or unsubstituted (C3-C30)cycloalkyl, a substituted or unsubstituted (C6-C30)aryl, a cyano, a substituted or unsubstituted (3- to 30-membered)heteroaryl, or a substituted or unsubstituted (C1-C30)alkoxy; or may be linked to an adjacent substituent to form a ring(s), e.g., a substituted or unsubstituted, quinoline, isoquinoline, benzofuropyridine, benzothienopyridine, indenopyridine, benzofuroquinoline, benzothienoquinoline, or indenoquinoline ring, together with pyridine;

$R_{104}$ to $R_{107}$, each independently, represent hydrogen, deuterium, a halogen, a (C1-C30)alkyl unsubstituted or substituted with deuterium(s) and/or a halogen(s), a substituted or unsubstituted (C3-C30)cycloalkyl, a substituted or unsubstituted (C6-C30)aryl, a substituted or unsubstituted (3- to 30-membered)heteroaryl, a cyano, or a substituted or unsubstituted (C1-C30)alkoxy; or may be linked to an adjacent substituent to form a ring, e.g., a substituted or unsubstituted, naphthalene, fluorene, dibenzothiophene, dibenzofuran, indenopyridine, benzofuropyridine, or benzothienopyridine ring, together with benzene;

$R_{201}$ to $R_{220}$, each independently, represent hydrogen, deuterium, a halogen, a (C1-C30)alkyl unsubstituted or substituted with deuterium(s) and/or a halogen(s), a substituted or unsubstituted (C3-C30)cycloalkyl, or a substituted or unsubstituted (C6-C30)aryl; or may be linked to an adjacent substituent to form a ring; and s represents an integer of 1 to 3.

The specific examples of the dopant compound are as follows, but are not limited thereto.

D-1

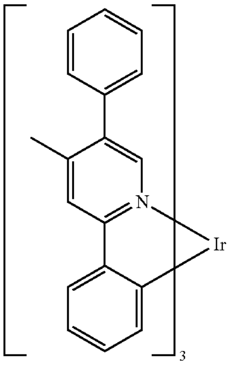

-continued

D-2

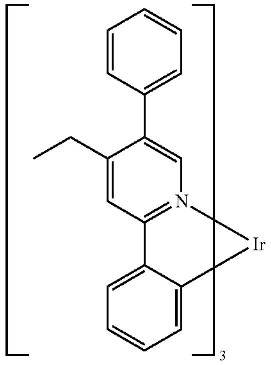

D-3

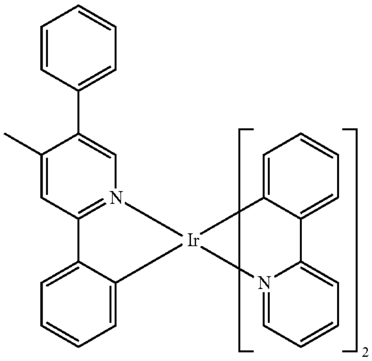

D-4

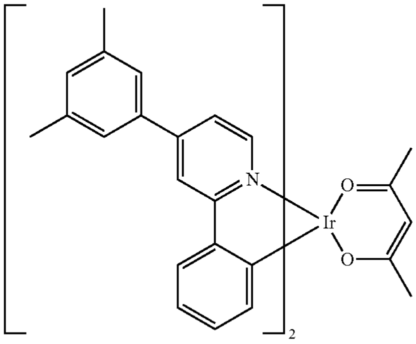

D-5

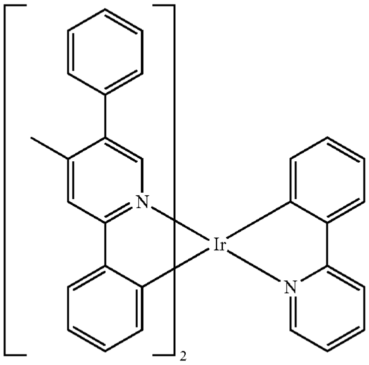

-continued
D-6
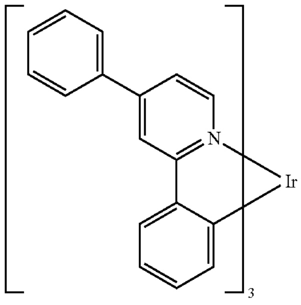
D-7
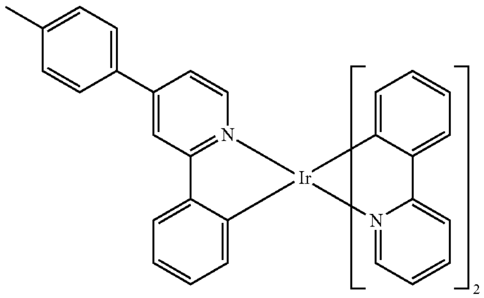
D-8
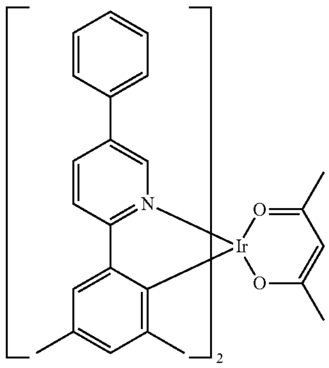
D-9
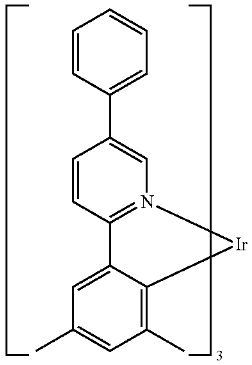
-continued
D-10
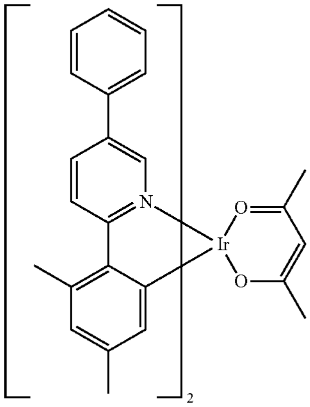
D-11
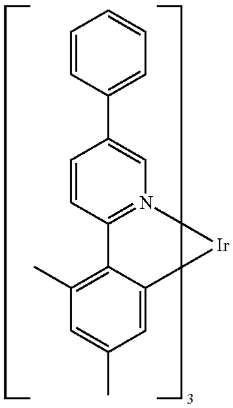
D-12
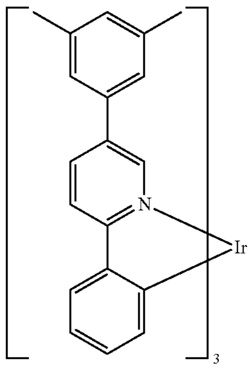
D-13
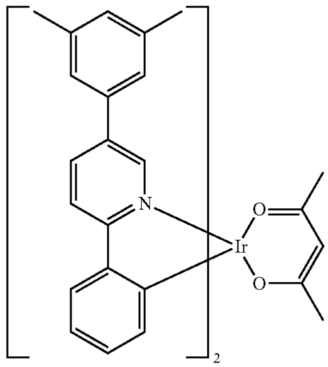

-continued
D-14
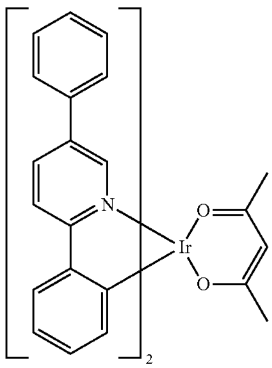
D-15
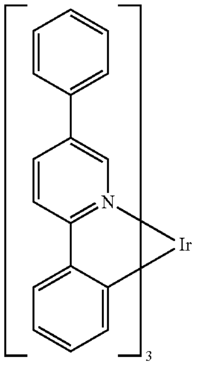
D-16
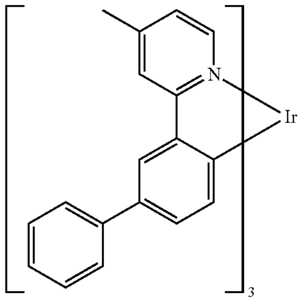
D-17
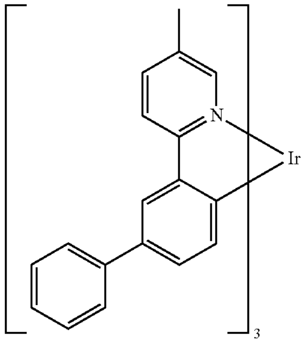
-continued
D-18
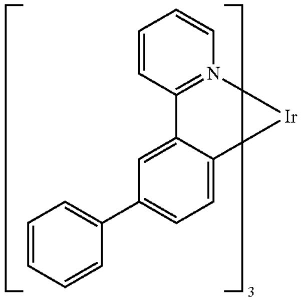
D-19
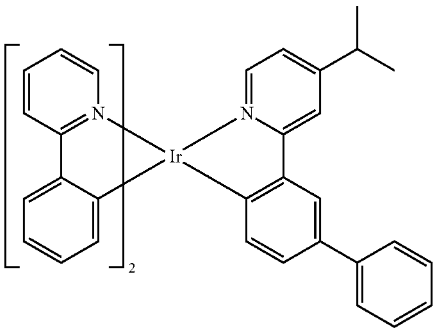
D-20
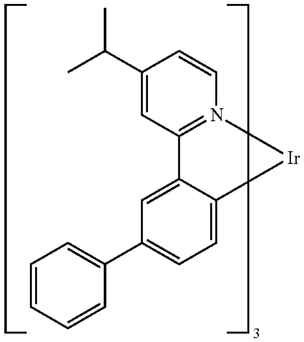
D-21
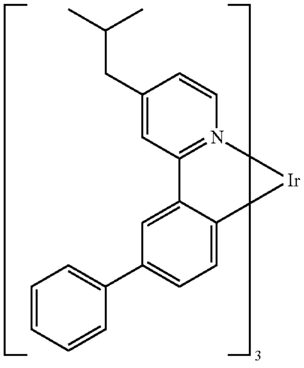

-continued
D-22
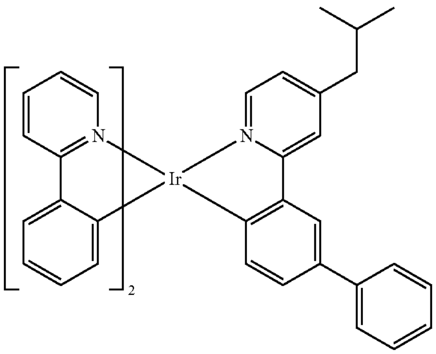
D-23
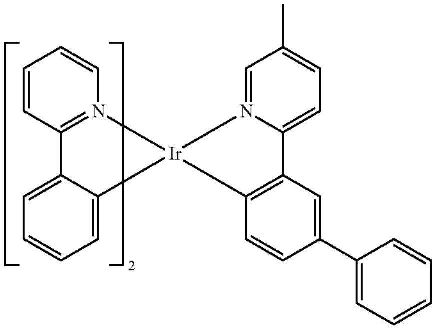
D-24
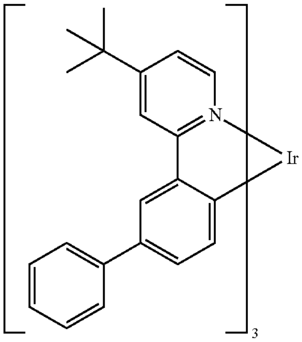
D-25
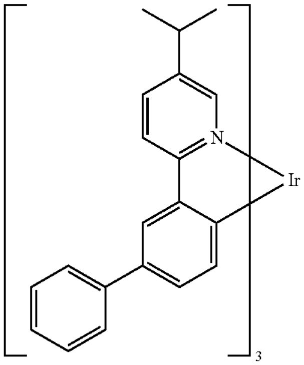
-continued
D-26
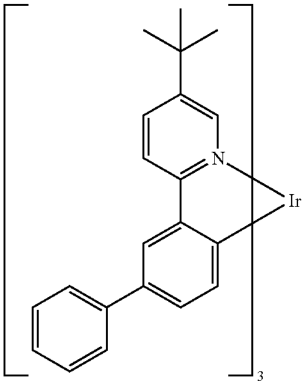
D-27
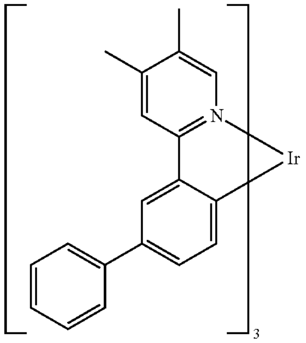
D-28
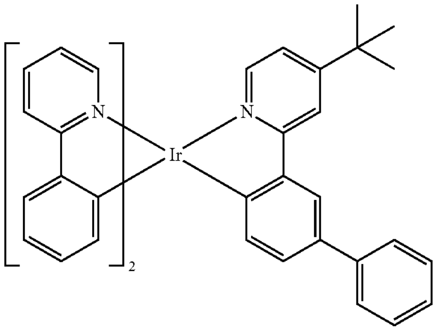
D-29
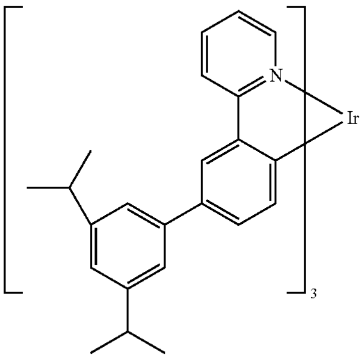

-continued
D-30
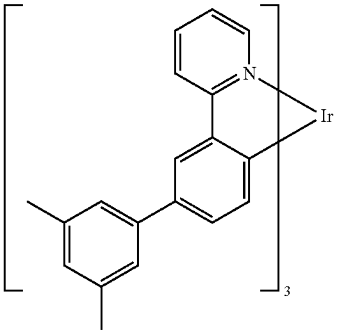
D-31
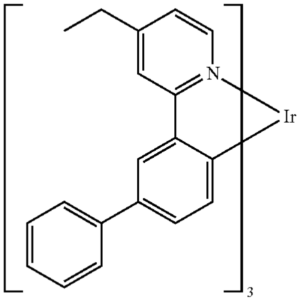
D-32
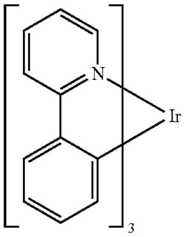
D-33
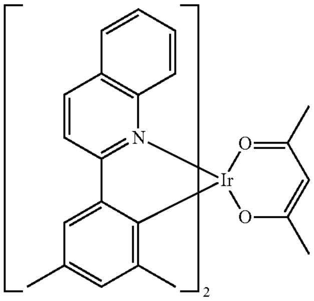
D-34
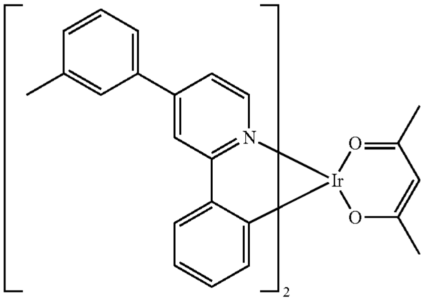
-continued
D-35
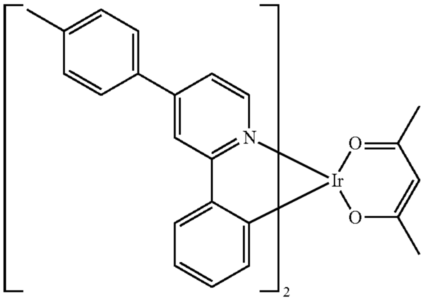
D-36
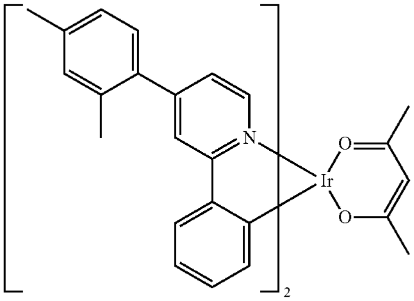
D-37
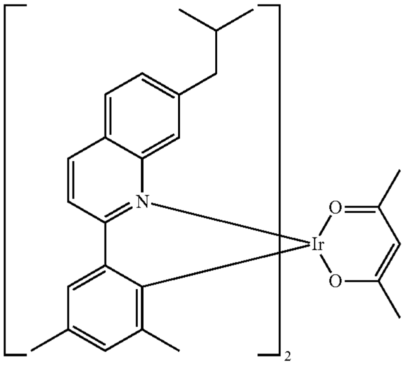
D-38
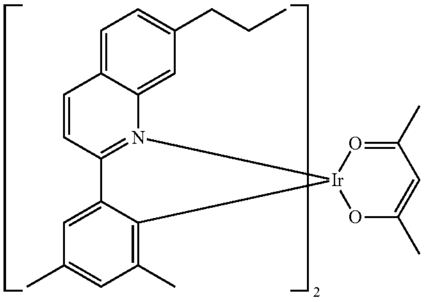

D-39
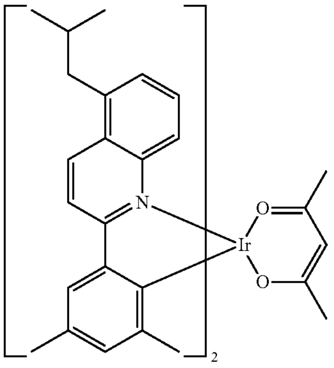
D-40
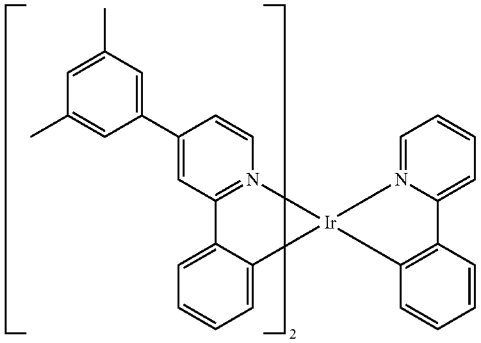
D-41
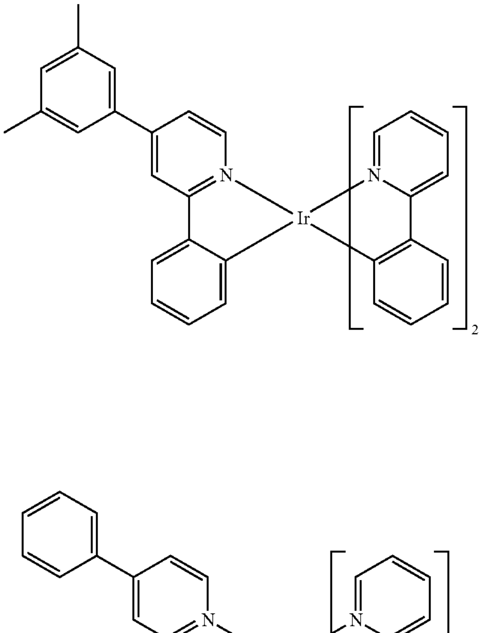
D-42
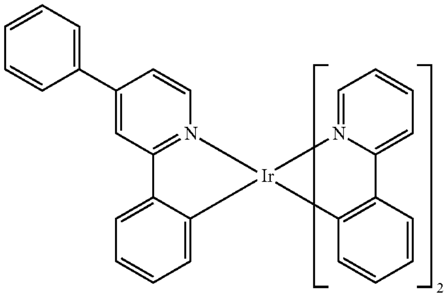
D-43
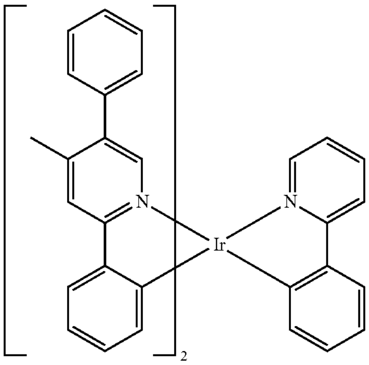
D-44
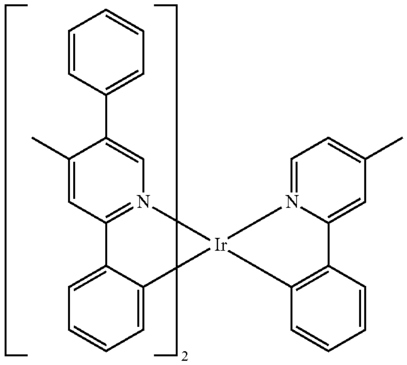
D-45
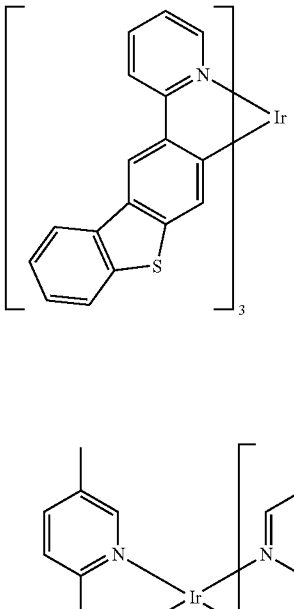
D-46
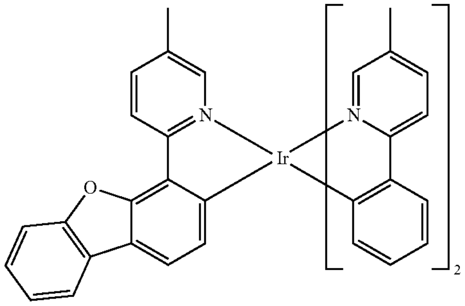

-continued
D-47
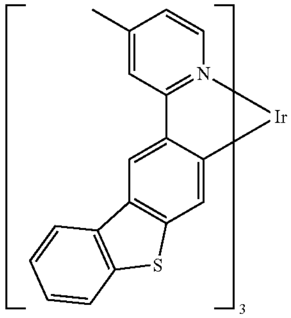
D-48
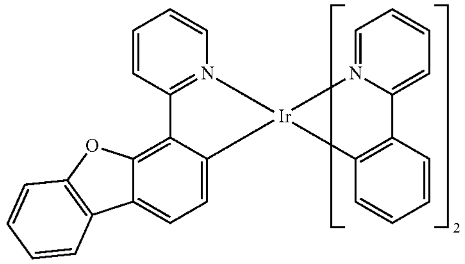
D-49
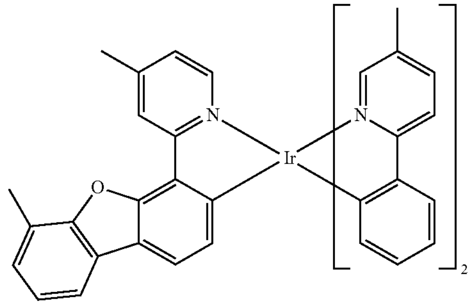
D-50
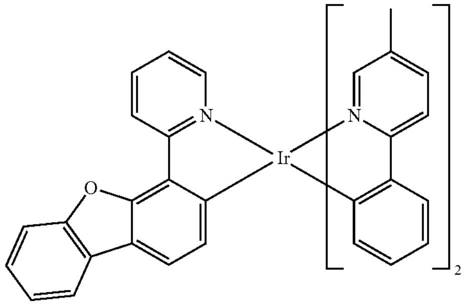
D-51
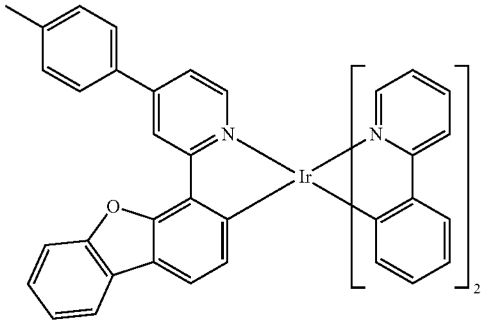
-continued
D-52
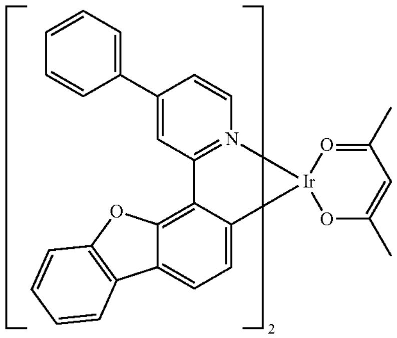
D-53
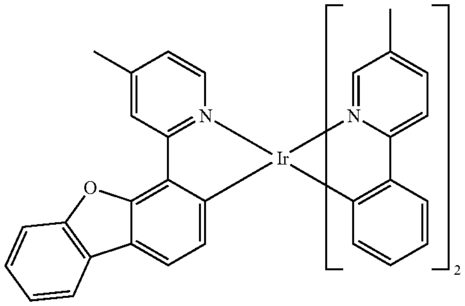
D-54
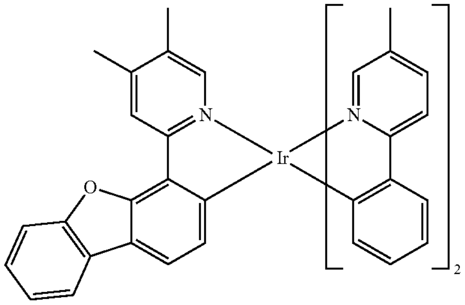
D-55
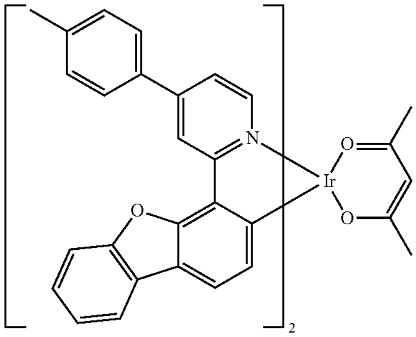
D-56
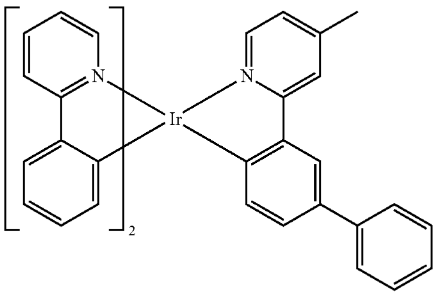

-continued
D-57
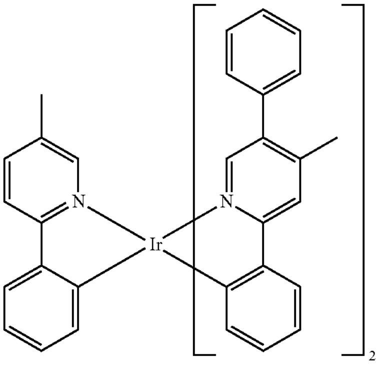
D-58
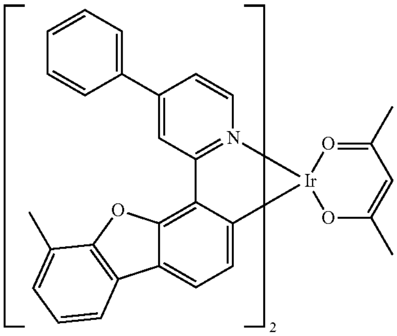
D-59
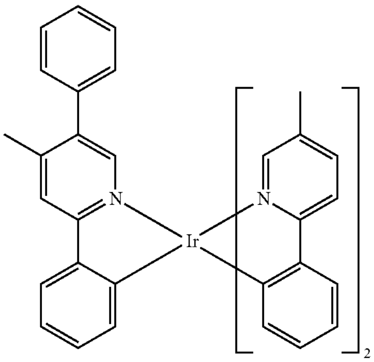
D-60
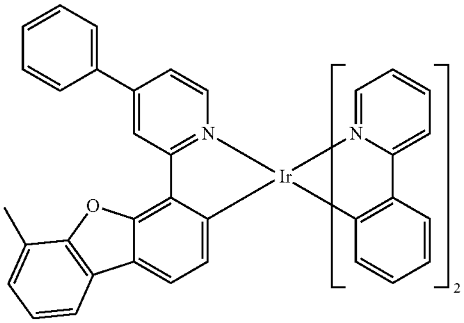
-continued
D-61
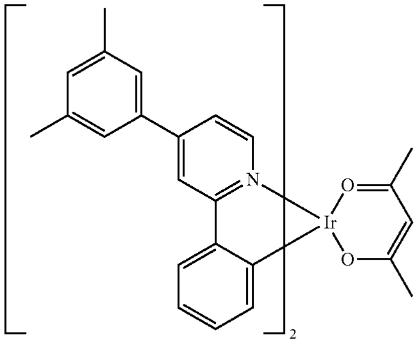
D-62
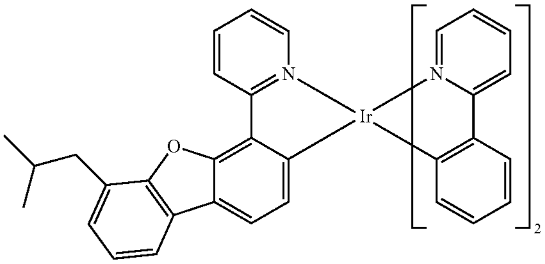
D-63
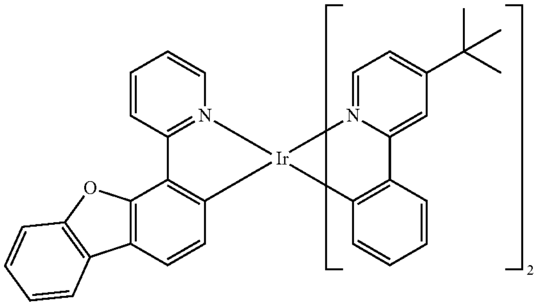
D-64
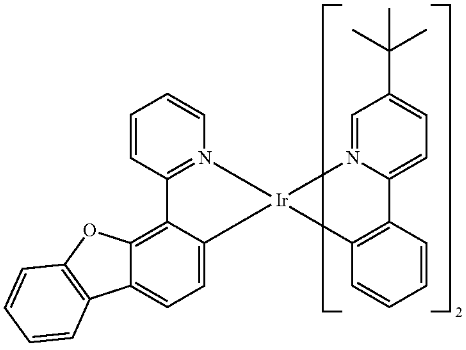

-continued
D-65
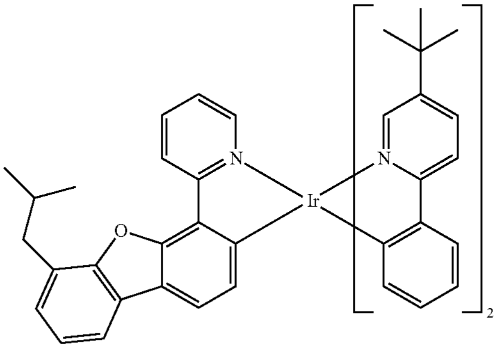
D-66
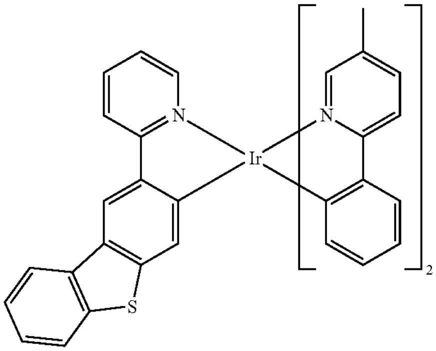
D-67
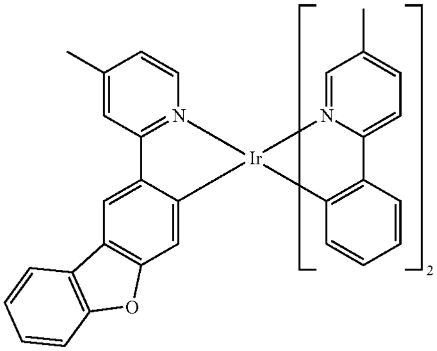
D-68
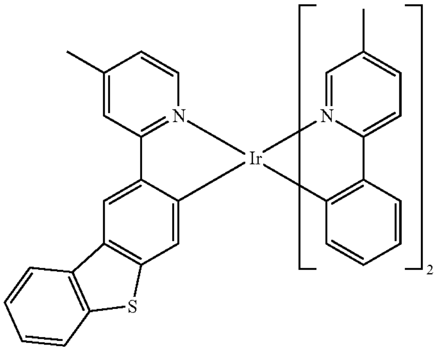
-continued
D-69
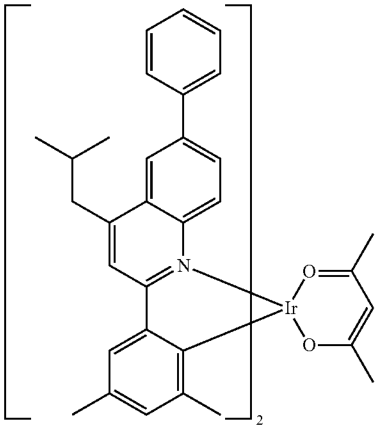
D-70
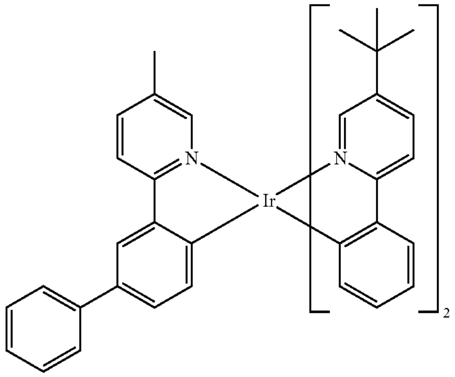
D-71
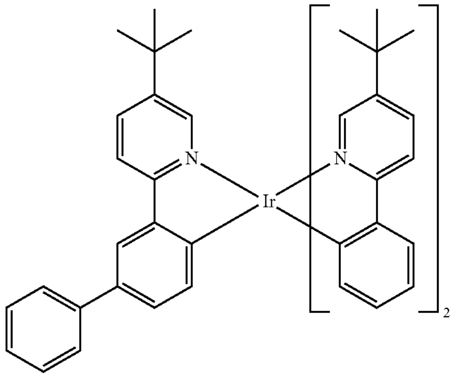
D-72
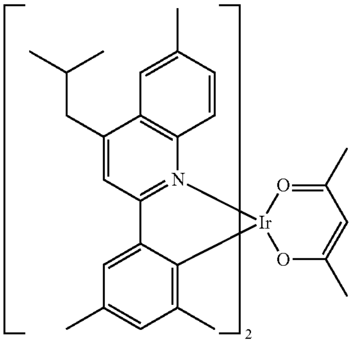

-continued
D-73
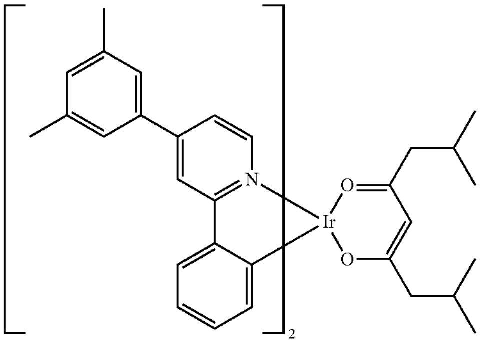
D-74
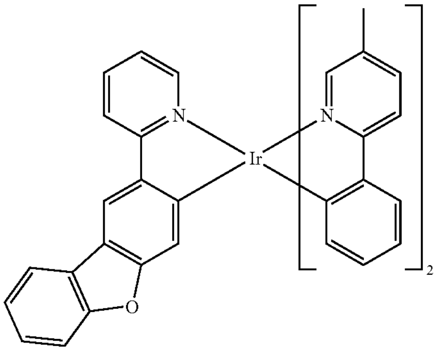
D-75
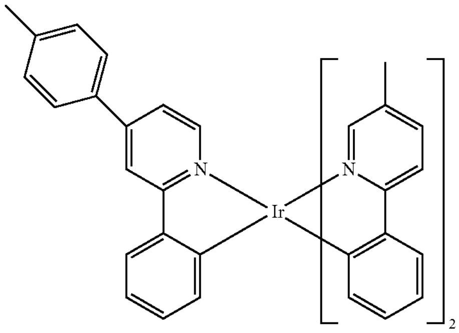
D-76
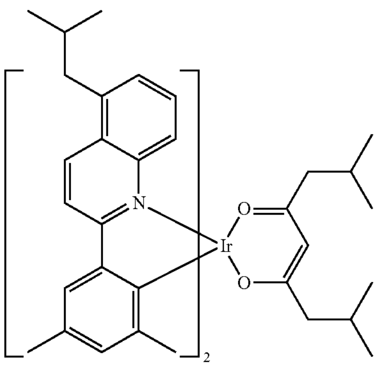
-continued
D-77
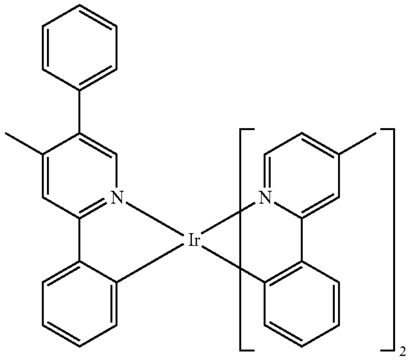
D-78
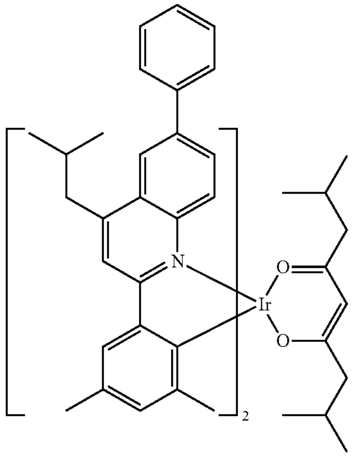
D-79
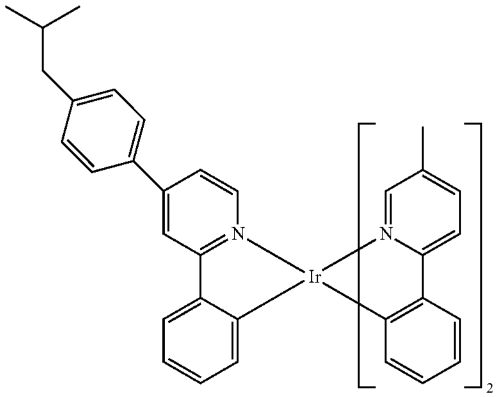
D-80
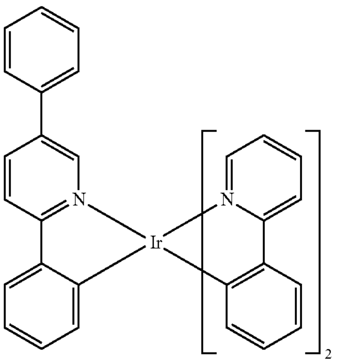

-continued
D-81
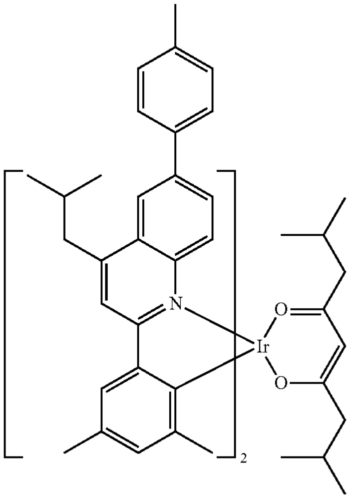
D-82
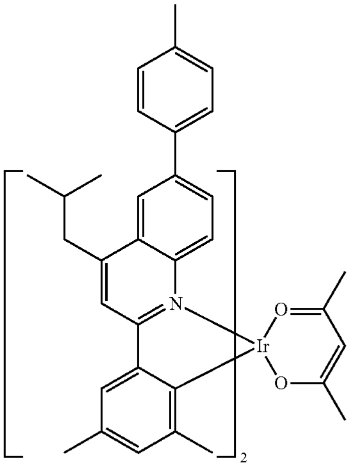
D-83
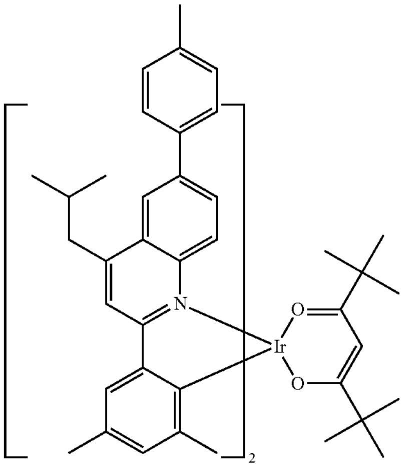
-continued
D-84
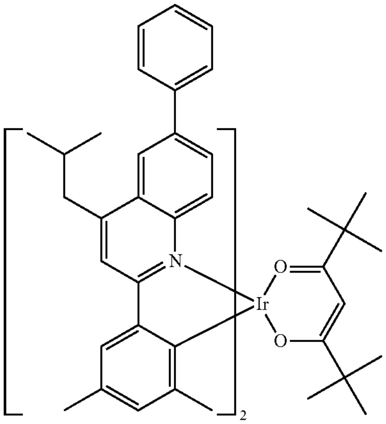
D-85
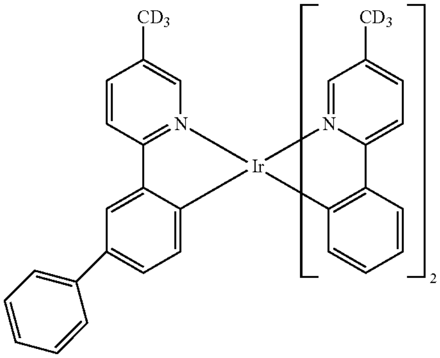
D-86
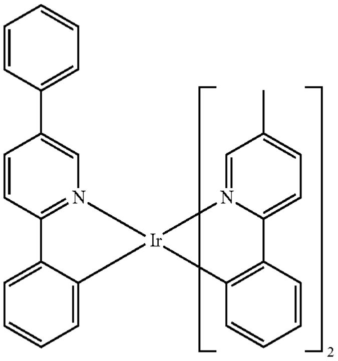
D-87
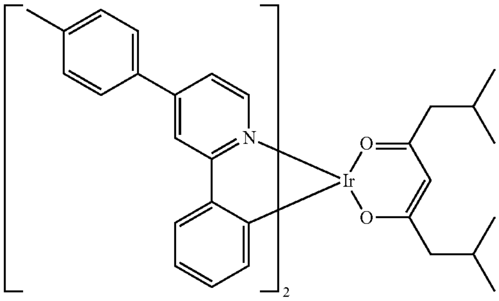

-continued
D-88
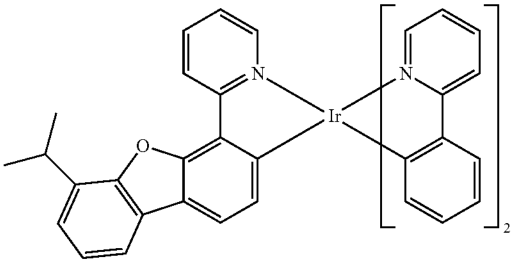
D-89
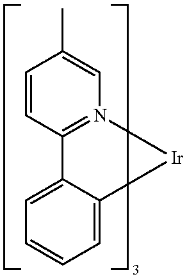
D-90
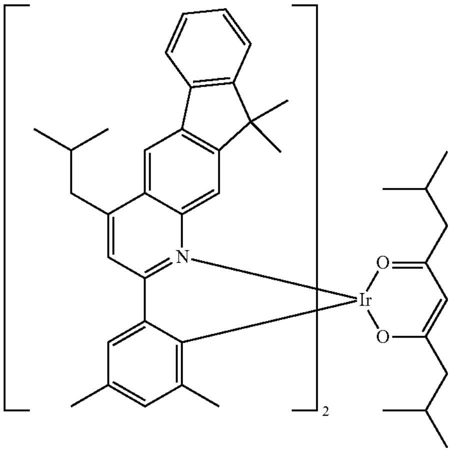
D-91
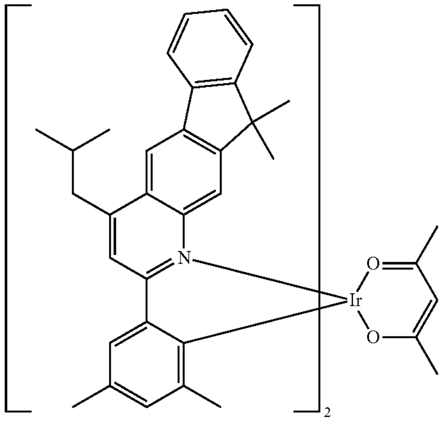
-continued
D-92
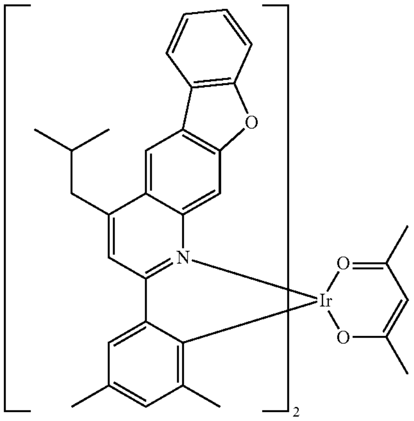
D-93
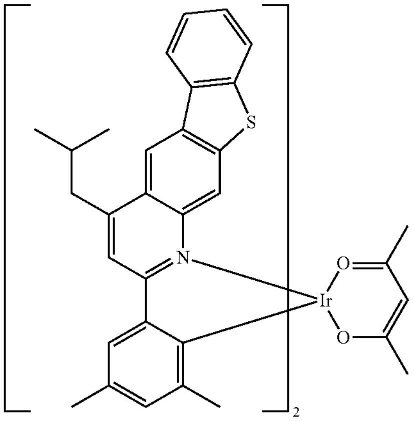
D-94
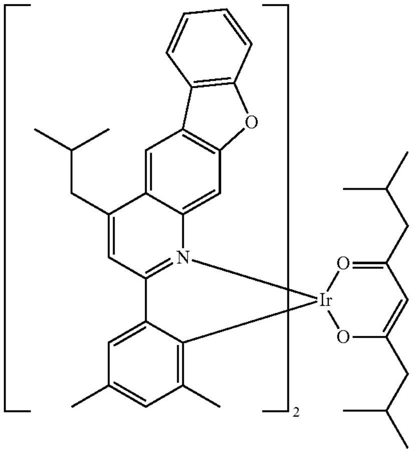

-continued
D-95
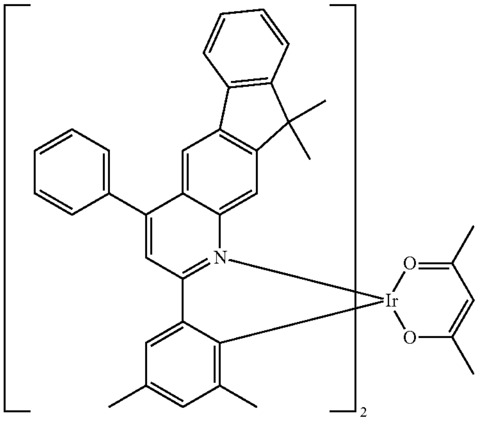
D-96
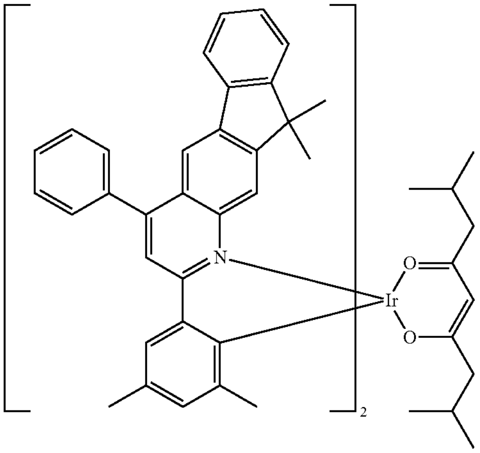
D-97
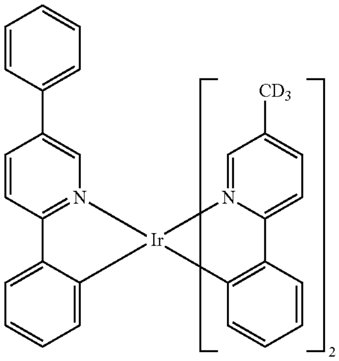
D-98
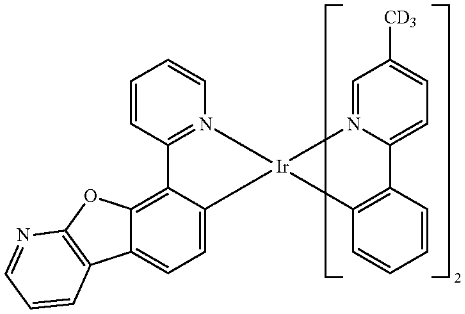
-continued
D-99
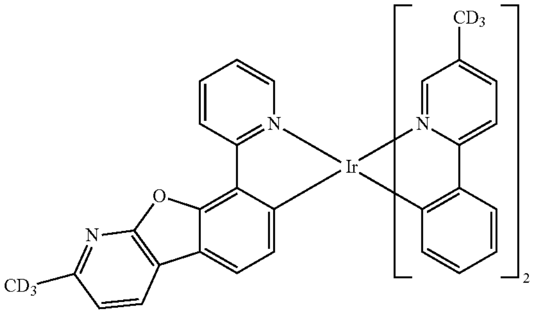
D-100
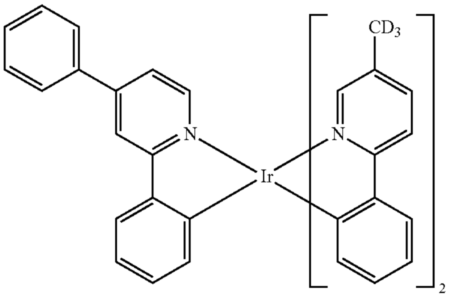
D-101
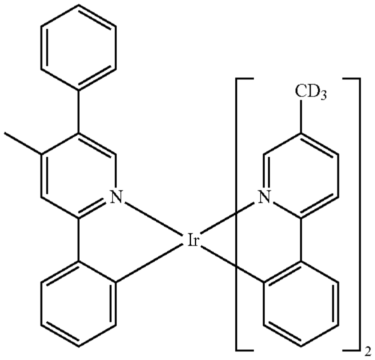
D-102
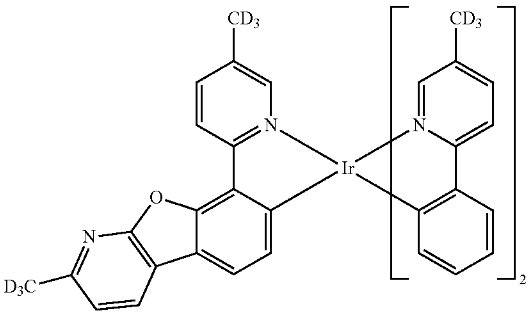

D-103
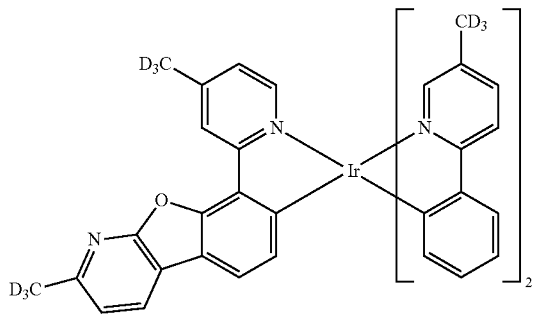
D-104
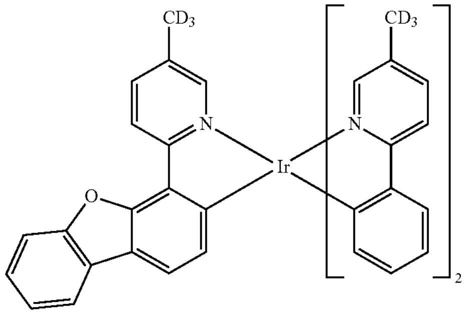
D-105
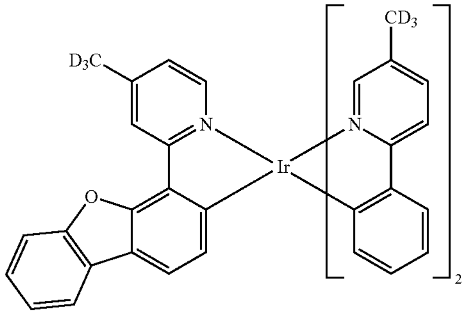
D-106
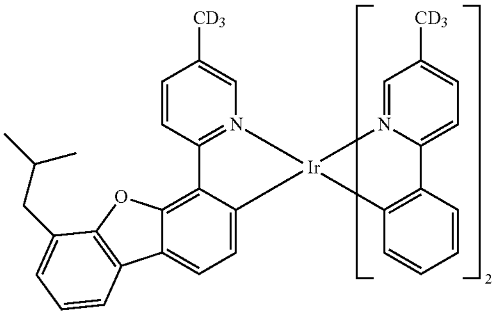
D-107
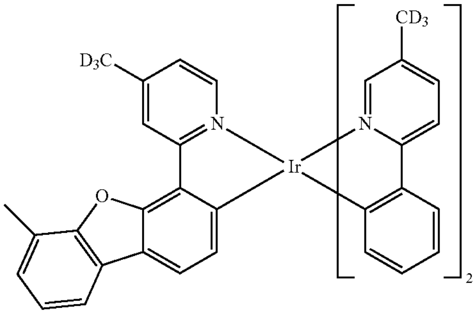
D-108
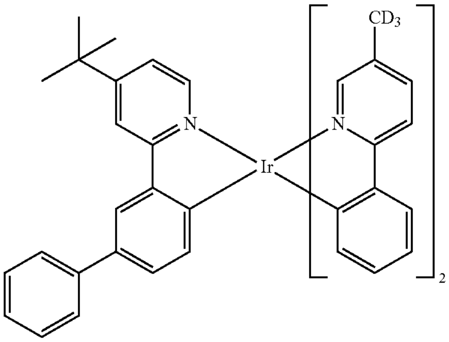
D-109
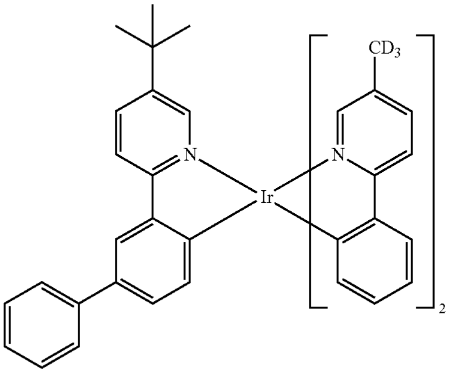
D-110
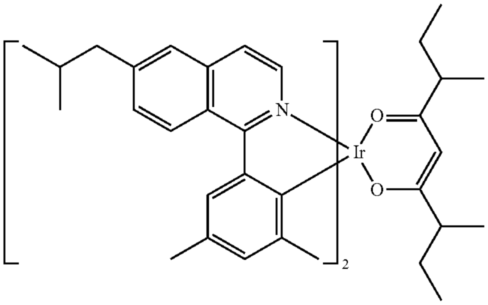
lp;3p
D-111
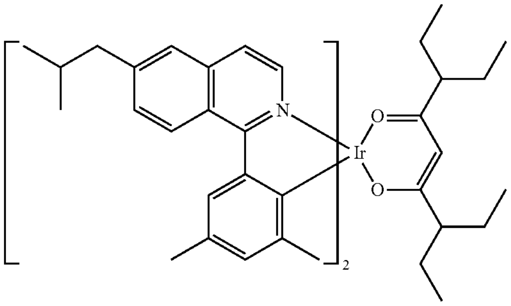

D-112
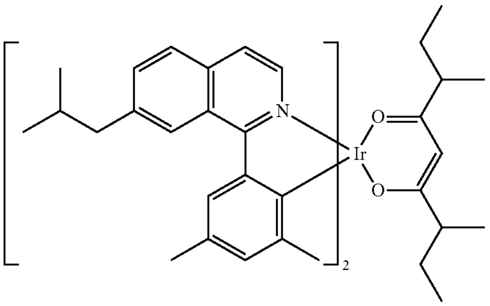
D-113
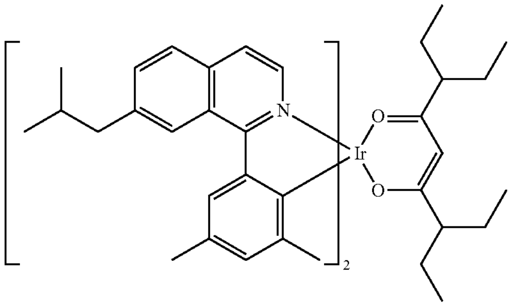
D-114
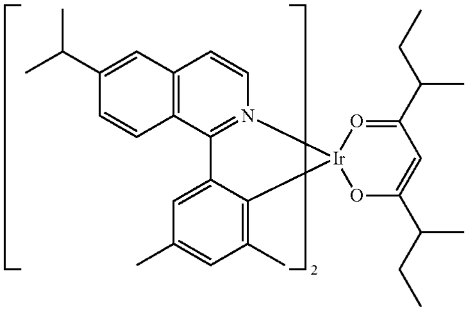
D-115
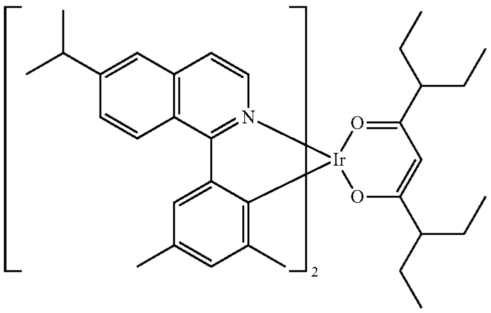
D-116
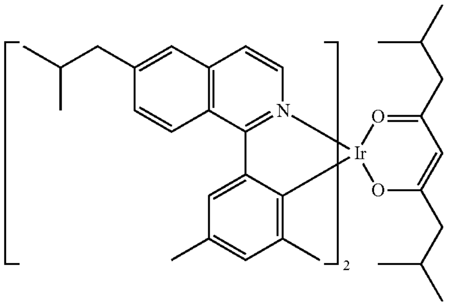
D-117
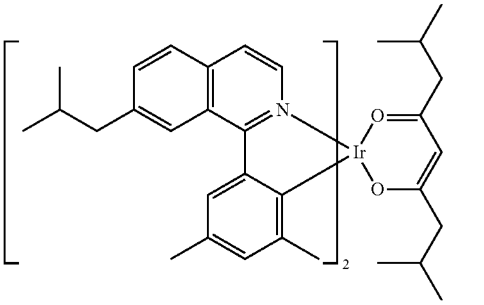
D-118
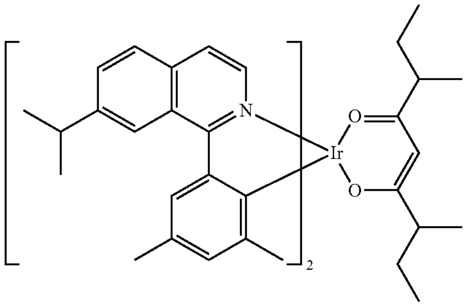
D-119
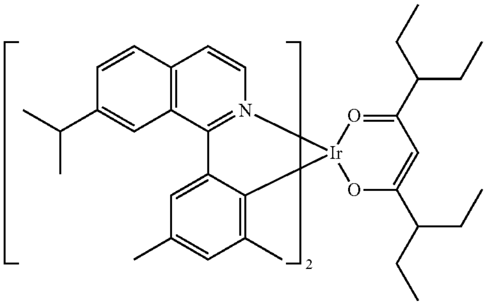
D-120
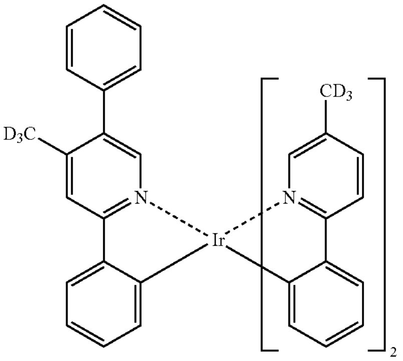
D-121
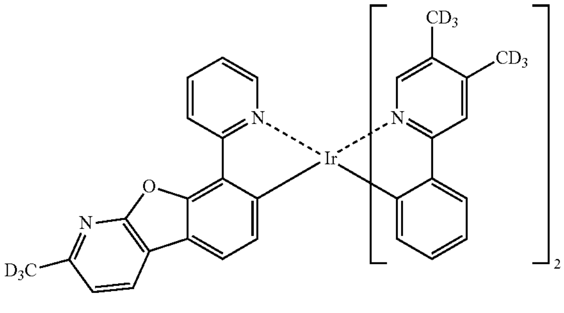

-continued
D-122
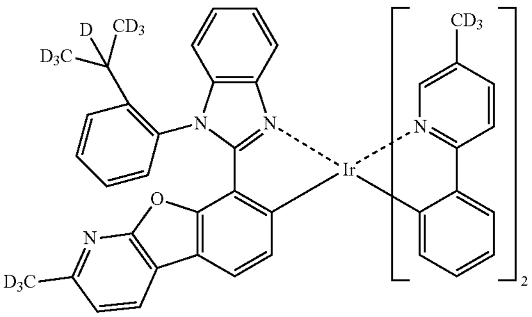
D-123
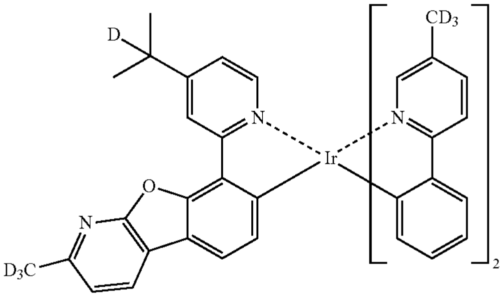
D-124
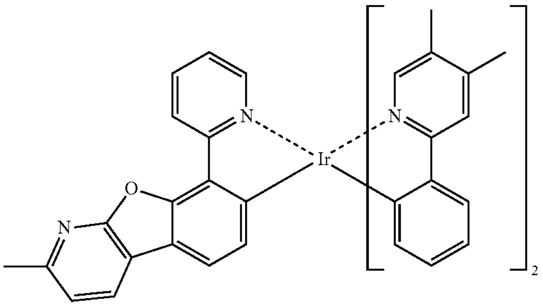
D-125
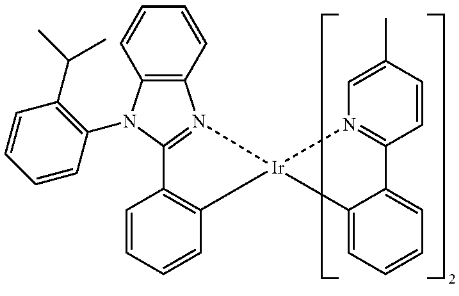
D-126
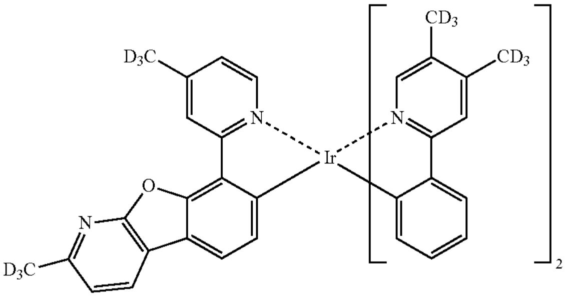
-continued
D-127
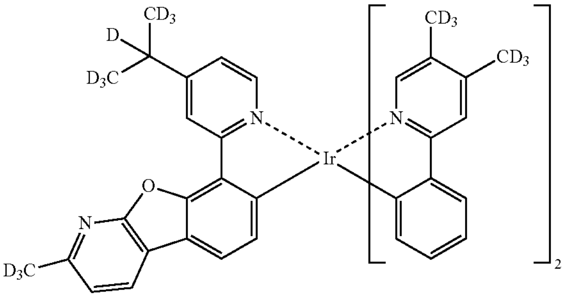
D-128
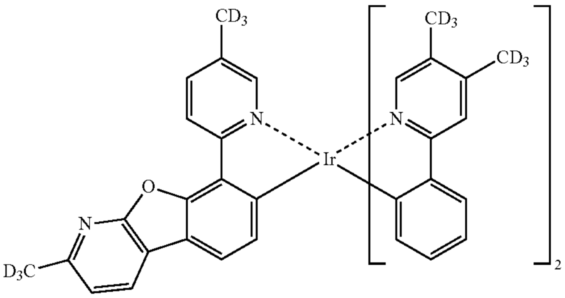
D-129
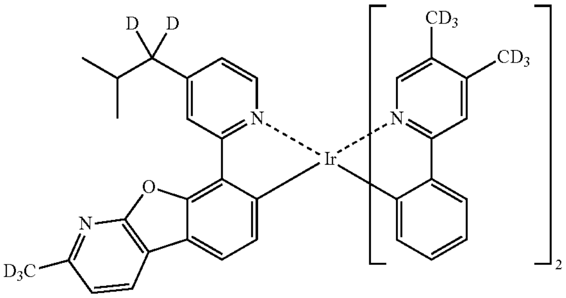
D-130
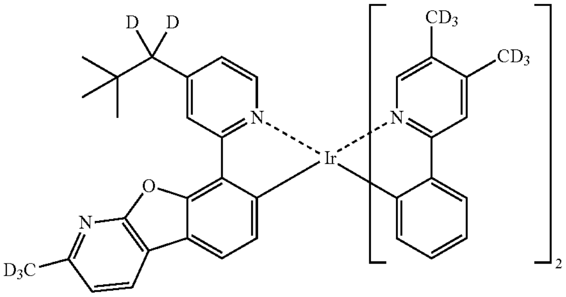
D-131
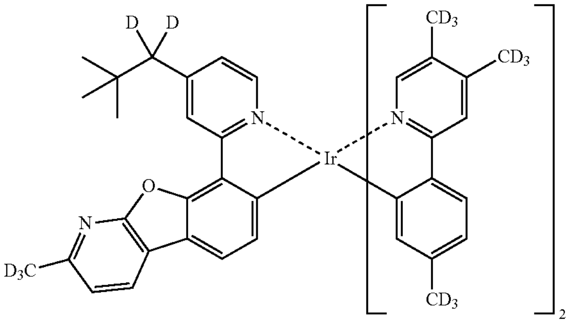

-continued
D-132
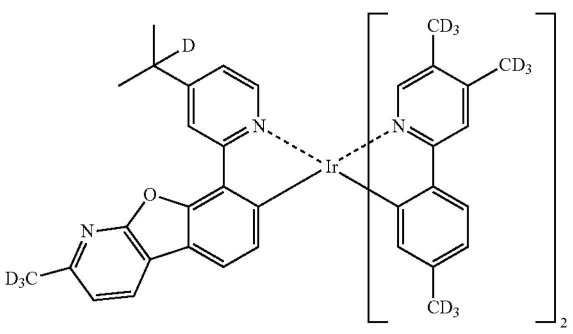
D-133
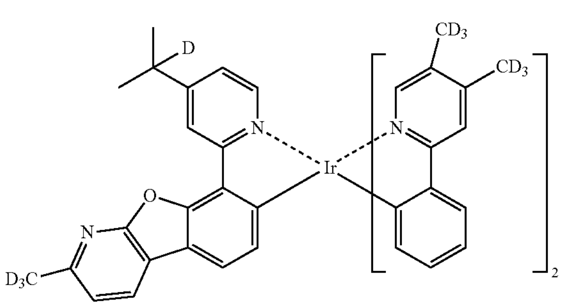
D-134
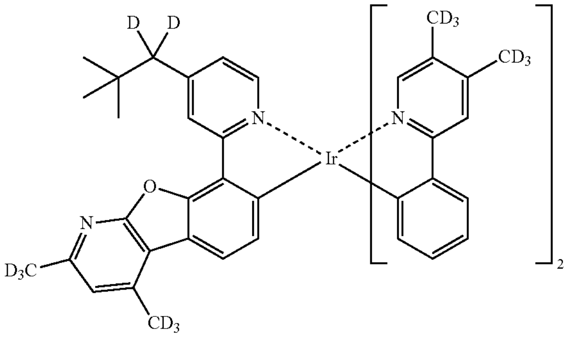
D-135
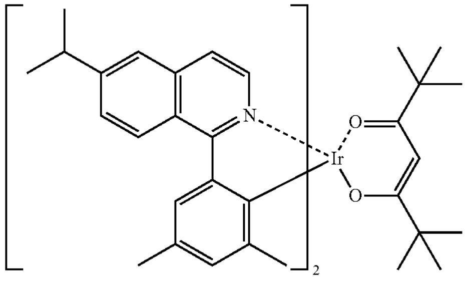
D-136
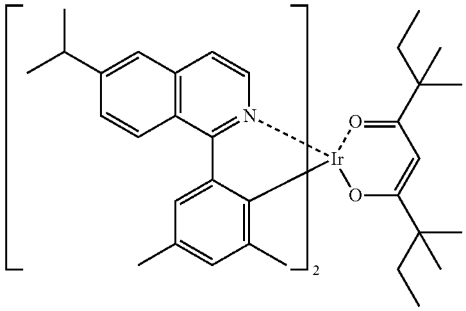
-continued
D-137
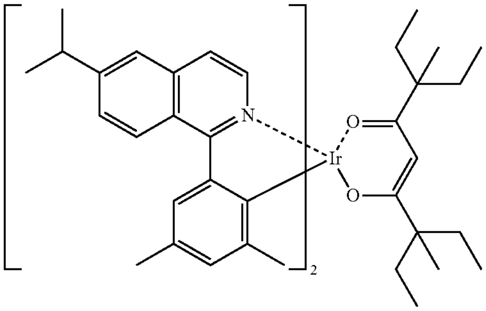
D-138
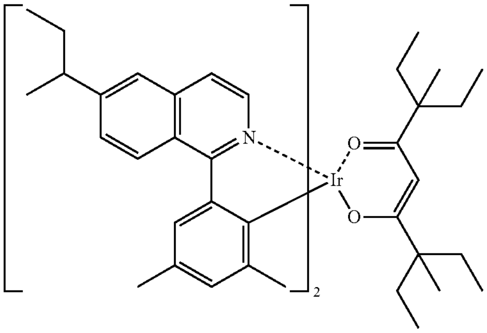
D-139
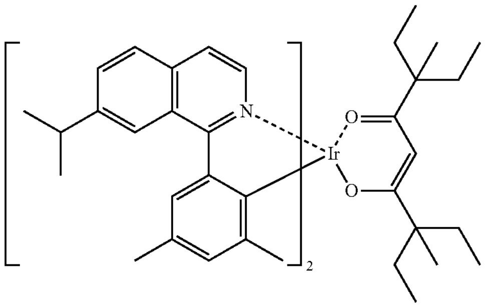
D-140
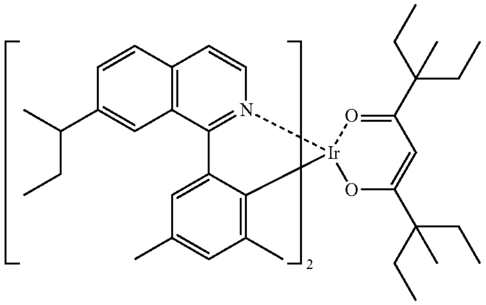
D-141
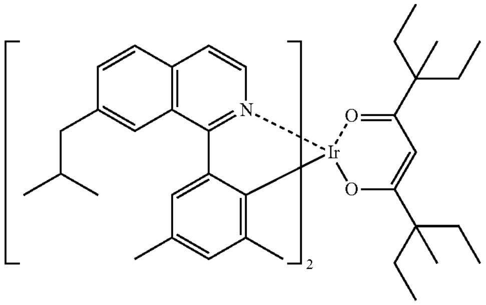

-continued
D-142
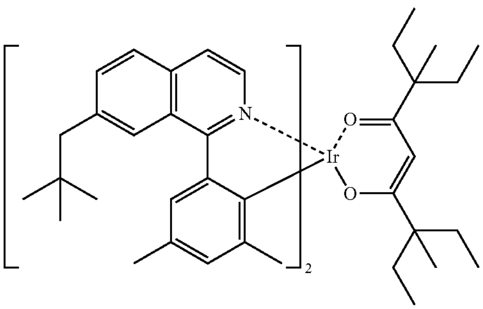
D-143
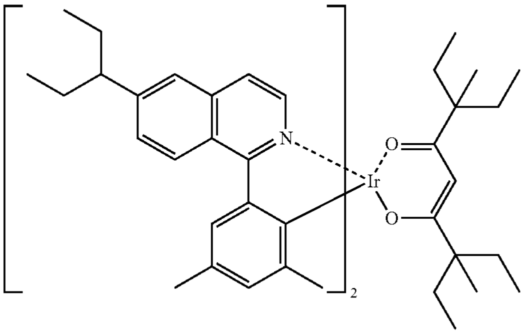
D-144
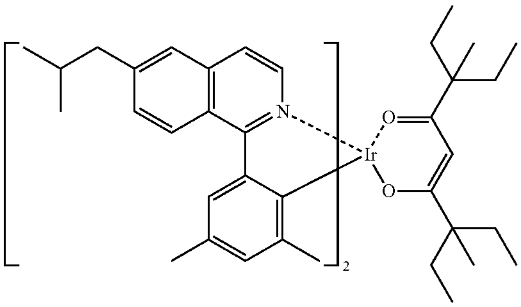
D-145
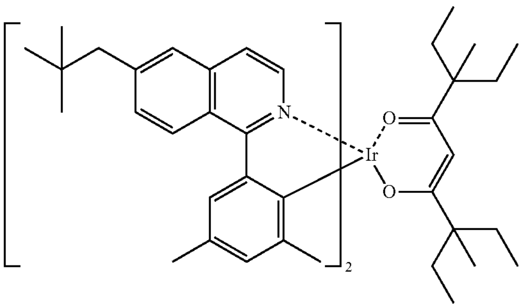
-continued
D-146
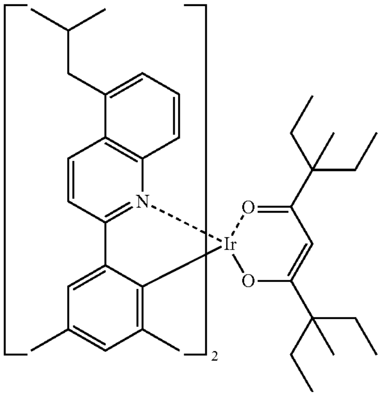
D-147
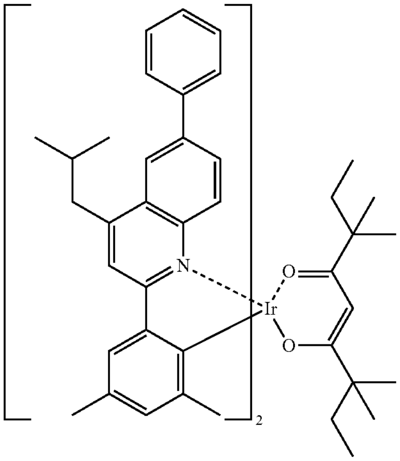
D-148
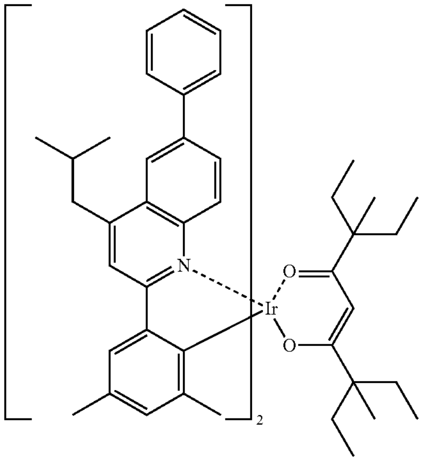

-continued

D-149

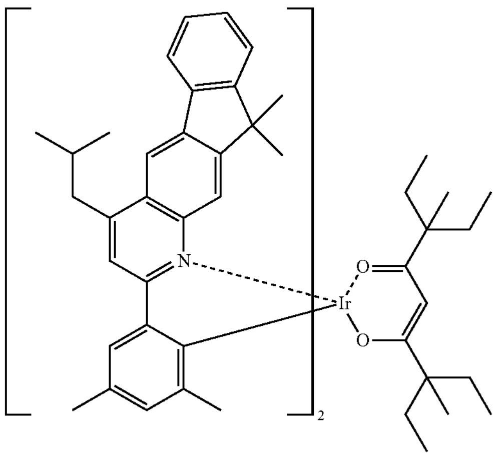

The present disclosure provides a composition for preparing an organic electroluminescent device as an additional embodiment. The composition is preferably a composition for preparing a hole transport layer, a hole auxiliary layer, a light-emitting auxiliary layer, or an electron blocking layer of an organic electroluminescent device, and includes the compound of the present disclosure. When there are two or more layers in a hole transport layer, the compound of the present disclosure may be included in the composition for preparing a hole transport layer (hole auxiliary layer) adjacent to the light-emitting layer.

In addition, the organic electroluminescent device of the present disclosure has a first electrode; a second electrode; and at least one organic layer interposed between the first electrode and the second electrode, and the organic layer comprises a hole transport layer, a hole auxiliary layer, a light-emitting auxiliary layer, or an electron blocking layer. The hole transport layer, the hole auxiliary layer, the light-emitting auxiliary layer, or the electron blocking layer may comprise the composition for organic electroluminescent device according to the present disclosure.

The organic electroluminescent device of the present disclosure comprises the organic electroluminescent compound of formula 1, and at the same time, may further comprise at least one compound selected from the group consisting of an arylamine-based compound and a styrylarylamine-based compound.

In addition, in the organic electroluminescent device of the present disclosure, the organic layer may further comprise at least one metal selected from the group consisting of metals of Group 1, metals of Group 2, transition metals of the $4^{th}$ period, transition metals of the $5^{th}$ period, lanthanides and organic metals of d-transition elements of the Periodic Table, or at least one complex compound comprising said metal, besides the organic electroluminescent compound of formula 1.

In addition, the organic electroluminescent device of the present disclosure may emit white light by further including at least one light-emitting layer containing a blue, red, or green light-emitting compound, which is known in the art, besides the organic electroluminescent compound of the present disclosure. In addition, it may further include a yellow or orange light-emitting layer, if necessary.

In the organic electroluminescent device of the present disclosure, at least one layer selected from a chalcogenide layer, a metal halide layer and a metal oxide layer (hereinafter, "a surface layer") may be preferably placed on an inner surface(s) of one or both electrodes. Specifically, a chalcogenide (including oxides) layer of silicon or aluminum is preferably placed on an anode surface of an electroluminescent medium layer, and a metal halide layer or a metal oxide layer is preferably placed on a cathode surface of an electroluminescent medium layer. The surface layer may provide operation stability for the organic electroluminescent device. Preferably, the chalcogenide includes $SiO_X$ ($1 \leq X \leq 2$), $AlO_X$ ($1 \leq X \leq 1.5$), SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

A hole injection layer, a hole transport layer, an electron blocking layer, or a combination thereof may be used between the anode and the light-emitting layer. The hole injection layer may be multilayers in order to lower the hole injection barrier (or hole injection voltage) from the anode to the hole transport layer or the electron blocking layer, wherein two compounds may be simultaneously used in each of the multilayers. In addition, the hole injection layer may be doped with p-dopant. The electron blocking layer may be placed between the hole transport layer (or hole injection layer) and the light-emitting layer, and may block overflowing electrons from the light-emitting layer and confine the excitons in the light-emitting layer to prevent light leakage. The hole transport layer or the electron blocking layer may be multilayers, wherein a plurality of compounds may be used in each of the multilayers.

An electron buffer layer, a hole blocking layer, an electron transport layer, an electron injection layer, or a combination thereof may be used between the light-emitting layer and the cathode. The electron buffer layer may be multilayers for the purpose of controlling electron injection and improving interfacial properties between the light-emitting layer and the electron injection layer, wherein two compounds may be simultaneously used in each of the multilayers. The hole blocking layer or the electron transport layer may also be multilayers, wherein a plurality of compounds may be used in each of the multilayers. In addition, the electron injection layer may be doped with n-dopant.

Here, the hole auxiliary layer or the light-emitting auxiliary layer is placed between the hole transport layer and the light-emitting layer, and may be used for controlling a hole transport rate. The hole auxiliary layer or the light-emitting auxiliary layer may provide an effect of improving the efficiency and lifetime of the organic electroluminescent device.

The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or the hole transport, or for preventing the overflow of electrons. When the light-emitting auxiliary layer is placed between the cathode and the light-emitting layer, it can be used for promoting the electron injection and/or the electron transport, or for preventing the overflow of holes. In addition, the hole auxiliary layer may be placed between the hole transport layer (or hole injection layer) and the light-emitting layer, and may be effective to promote or block the hole transport rate (or the hole injection rate), thereby enabling the charge balance to be controlled. Further, the electron blocking layer may be placed between the hole transport layer (or hole injection layer) and the light-emitting layer, and may block overflowing electrons from the light-emitting layer and confine the excitons in the light-emitting layer to prevent light leakage. When an organic electroluminescent device includes two or more hole transport layers, the additional hole transport layer may be used as a hole auxiliary layer or an electron blocking layer. The hole auxiliary layer and the electron blocking layer has an effect of improving the efficiency and/or the lifetime of the organic electroluminescent device.

In the organic electroluminescent device of the present disclosure, a mixed region of an electron transport compound and a reductive dopant, or a mixed region of a hole transport compound and an oxidative dopant is preferably placed on at least one surface of a pair of electrodes. In this case, the electron transport compound is reduced to an anion, and thus it becomes easier to inject and transport electrons from the mixed region to an electroluminescent medium. Further, the hole transport compound is oxidized to a cation, and thus it becomes easier to inject and transport holes from the mixed region to the electroluminescent medium. Preferably, the oxidative dopant includes various Lewis acids and acceptor compounds; and the reductive dopant includes alkali metals, alkali metal compounds, alkaline earth metals, rare-earth metals, and mixtures thereof. A reductive dopant layer may be employed as a charge-generating layer to prepare an organic electroluminescent device having two or more light-emitting layers, which emits white light.

An organic electroluminescent material according to one embodiment of the present disclosure may be used as light-emitting materials for a white organic light-emitting device. The white organic light-emitting device has been suggested in various structures such as a parallel side-by-side arrangement method, a stacking arrangement method, or CCM (color conversion material) method, etc., according to the arrangement of R (Red), G (Green) or YG (yellowish green), and B (blue) light-emitting units. In addition, the organic electroluminescent material according to one embodiment of the present disclosure may also be applied to the organic electroluminescent device comprising a QD (quantum dot).

In order to form each layer of the organic electroluminescent device of the present disclosure, dry film-forming methods such as vacuum evaporation, sputtering, plasma, ion plating, etc., or wet film-forming methods such as ink jet printing, spin coating, dip coating, flow coating, etc., can be used.

When using a wet film-forming method, a thin film can be formed by dissolving or diffusing the materials forming each layer into any suitable solvent such as ethanol, chloroform, tetrahydrofuran, dioxane, etc. The solvent is not specifically limited as long as the material forming each layer is soluble or dispersible in the solvents, which do not cause any problems in forming a film.

It is possible to produce a display system, e.g., a display system for smartphones, tablets, notebooks, PCs, TVs, or cars, or a lighting system, e.g., an outdoor or indoor lighting system, by using the organic electroluminescent device of the present disclosure.

Hereinafter, the preparation method of the compound of the present disclosure, and the properties thereof, and the luminous property of the organic electroluminescent device comprising the same will be explained in detail with reference to the representative compounds of the present disclosure. However, the present disclosure is not limited to the following examples.

Example 1: Preparation of Compound A-100

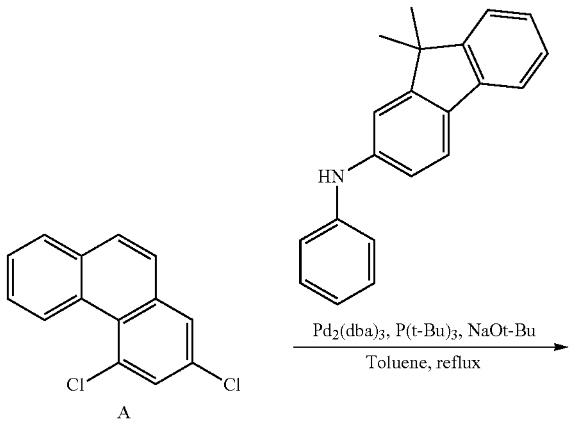

-continued

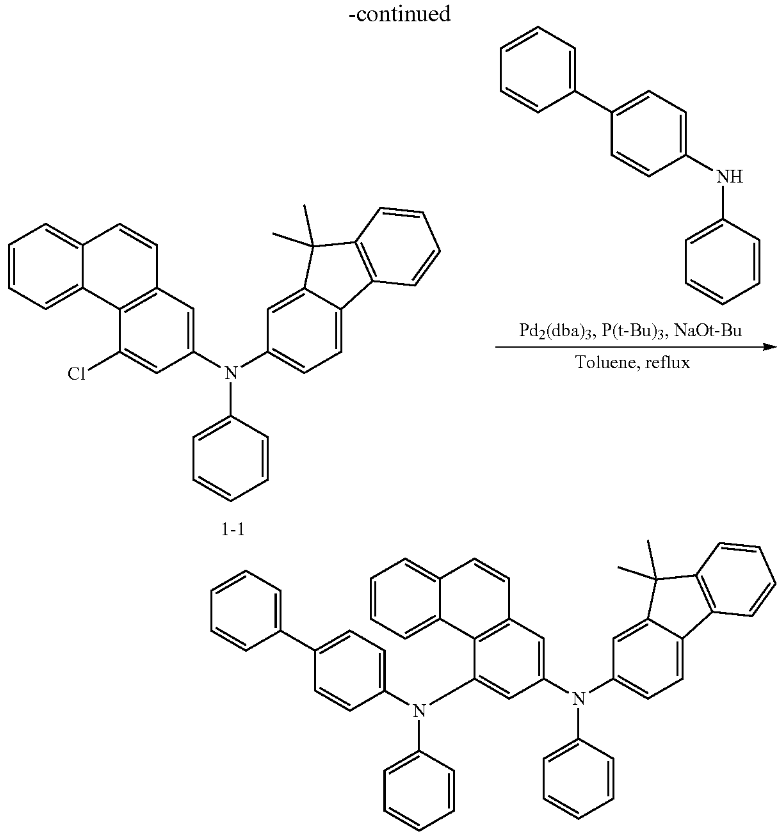

1-1

A-100

Synthesis of Compound 1-1

Compound A (4.0 g, 16.18 mmol), 9,9-dimethyl-N-phenyl-9H-fluoren-2-amine (4.6 g, 16.18 mmol), tris(dibenzylidineacetone)dipalladium (0.74 g, 0.81 mmol), tri-tert-butylphosphine (0.8 mL, 1.62 mmol), sodium tert-butoxide (2.4 g, 24.27 mmol), and 81 mL of toluene were added to a reaction vessel, and stirred under reflux for 1 hour. After the reaction was completed, the mixture was washed with distilled water and the organic layer was extracted with ethyl acetate. After the organic layer was dried with magnesium sulfate, the solvent was removed by a rotary evaporator, and then purified by column chromatography to obtain compound 1-1 (5.6 g, yield: 70%).

Synthesis of Compound A-100

Compound 1-1 (5.6 g, 11.31 mmol), N-phenyl-[1,1'-biphenyl]-4-amine (3.6 g, 14.70 mmol), tris(dibenzylidineacetone)dipalladium (0.52 g, 0.57 mmol), tri-tert-butylphosphine (0.55 mL, 1.13 mmol), sodium tert-butoxide (1.63 g, 16.97 mmol), and 57 mL of toluene were added to a reaction vessel, and stirred under reflux for 1 hour. After the reaction was completed, the mixture was washed with distilled water and the organic layer was extracted with ethyl acetate. After the organic layer was dried with magnesium sulfate, the solvent was removed by a rotary evaporator, and then purified by column chromatography to obtain compound A-100 (1.8 g, yield: 22%).

| | MW | M.P. |
|---|---|---|
| A-100 | 704.3 | 226° C. |

Example 2: Preparation of Compound A-11

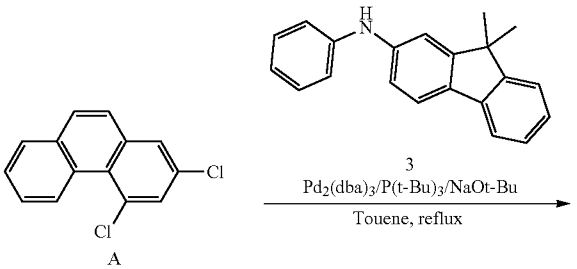

3

A

-continued

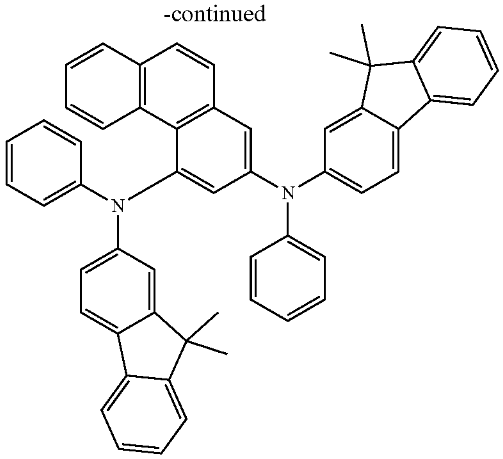

A-11

Compound A (5.0 g, 20.23 mmol), 9,9-dimethyl-N-phenyl-9H-fluoren-2-amine (12.7 g, 44.51 mmol), tris(dibenzylideneacetone)dipalladium(0) (1.9 g, 2.02 mmol), tri-tert-butylphosphine (1.9 mL, 4.04 mmol), sodium tert-butoxide (5.8 g, 60.69 mmol), and 100 mL of toluene were added to a reaction vessel, and stirred under reflux for 4 hour. After the reaction was completed, the reaction mixture was cooled to room temperature, and the solid was filtered and washed with ethyl acetate. The filtrate was distilled under reduced pressure and purified by column chromatography to obtain compound A-11 (4 g, yield: 26%).

| | MW | M.P. |
|---|---|---|
| A-11 | 744.98 | 172° C. |

Device Example 1: Producing an OLED Comprising a Compound According to the Present Disclosure An OLED comprising an organic electroluminescent compound according to the present disclosure was produced. First of all, a transparent electrode indium tin oxide (ITO) thin film (10 Ω/sq) on a glass substrate for an OLED (GEOMATEC CO., LTD., Japan) was subjected to an ultrasonic washing with acetone, ethanol, and distilled water, sequentially, and then was stored in isopropyl alcohol before use. After evacuating until the degree of vacuum in the chamber reached $10^{-6}$ torr, the ITO substrate was mounted on a substrate holder of the vacuum vapor deposition apparatus. Compound HT-1 was introduced into a cell of the vacuum vapor deposition apparatus as a first hole injection compound, and compound HI-1 was introduced into another cell. The two materials were evaporated at different rates to deposit a hole injection layer with a thickness of 10 nm by doping compound HI-1 in an amount of 3 wt % based to the total amount of compound HT-1 and compound HI-1. Subsequently, the material of compound HT-1 was evaporated to the first hole transport layer, thereby depositing a first hole transport layer on the hole injection layer with a thickness of 90 nm. Subsequently, compound A-11 according to the present disclosure was introduced into another cell of the vacuum vapor deposition apparatus and was evaporated by applying an electric current to the cell, thereby depositing a second hole transport (or auxiliary) layer with a thickness of 60 nm on the first hole transport layer. After forming the hole injection layer and the hole transport (or auxiliary) layers, a light-emitting layer was deposited thereon as follows: Compound RH was introduced into a cell of the vacuum vapor deposition apparatus as a host of the light-emitting layer, and compound D-39 was introduced into another cell as a dopant. The two materials were evaporated to deposit a light-emitting layer with a thickness of 40 nm on the second hole transport layer by doping the dopant in an amount of 2 wt % based on the total amount of the host and dopant. Subsequently, compound ET-1 and compound EI-1 in two different cells were evaporated at a rate of 1:1 to deposit an electron transport layer with a thickness of 35 nm on the light-emitting layer. After depositing compound EI-1 to a thickness of 2 nm as an electron injection layer, an Al cathode was deposited to a thickness of 80 nm by using another vacuum vapor deposition apparatus to produce an OLED.

As a result, the driving voltage based on 1,000 nit of the organic electroluminescent device of Device Example 1 was 3.1 V, and the power efficiency was 28.8 lm/W.

Device Example 2: Producing an OLED Comprising a Compound According to the Present Disclosure An OLED was produced in the same manner as in Device Example 1, except that compound A-100 was used as a material for the second hole transport (or auxiliary) layer.

As a result, the driving voltage based on 1,000 nit of the organic electroluminescent device of Device Example 2 was 3.5 V, and the power efficiency was 28.4 lm/W.

Comparative Example: Producing an OLED Comprising a Conventional Compound

An OLED was produced in the same manner as in Device Example 1, except that compound B-1 was used as a material for the second hole transport (or auxiliary) layer.

As a result, the driving voltage based on 1,000 nit of the organic electroluminescent device of Comparative Example was 4.4 V, and the power efficiency was 23.6 lm/W.

It was confirmed that the power efficiency of the organic electroluminescent device comprising the compound of the present disclosure in a hole transport (or auxiliary) layer exhibited a lower driving voltage than that of the conventional organic electroluminescent device. In addition, the organic electroluminescent device comprising the compound of the present disclosure is expected to reduce power consumption from the result of showing high power efficiency.

The compounds used in the Device Examples and Comparative Example are shown in Table 1 below.

TABLE 1
| | |
|---|---|
| Hole Injection Layer/First Hole Transport Layer | 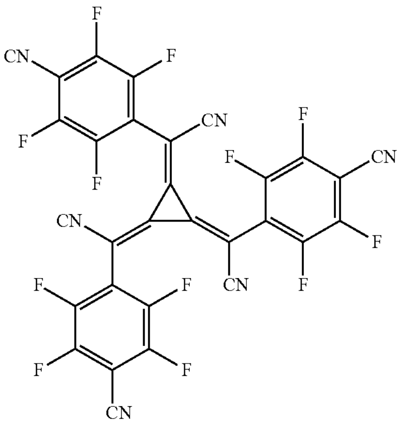 HI-1 |
| | 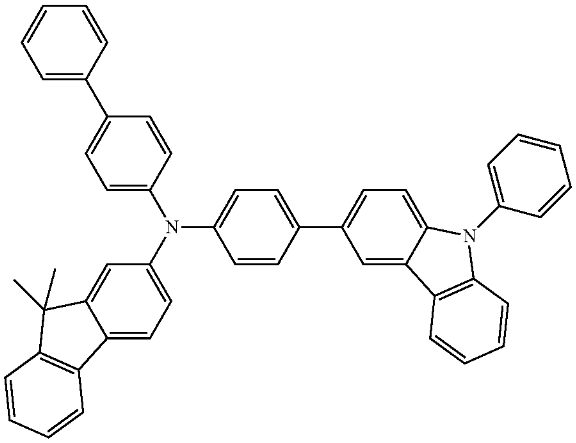 HT-1 |
| Second Hole Transport Layer | 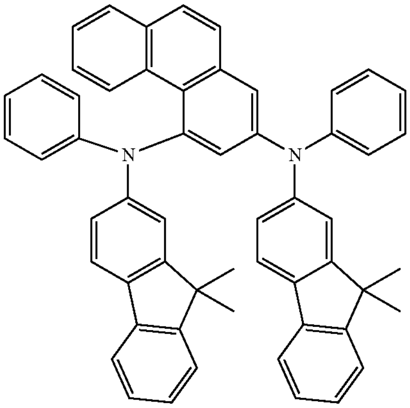 A-11 |

TABLE 1-continued
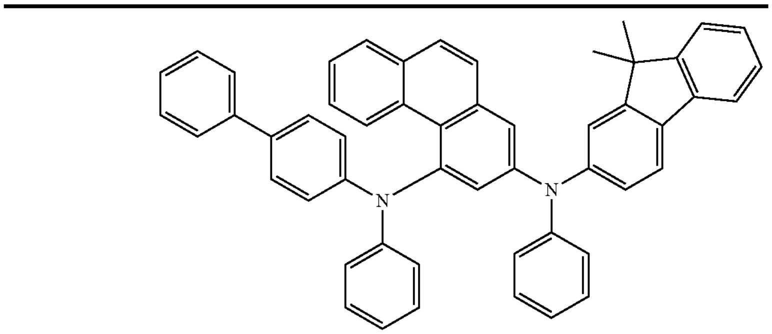
A-100
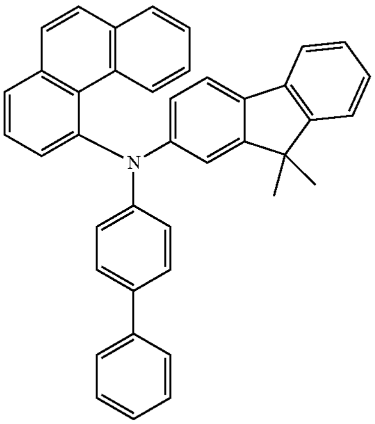
B-1
Light-Emitting Layer
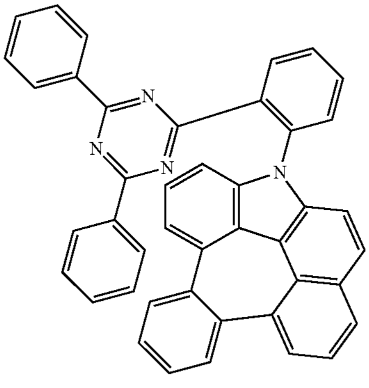
RH
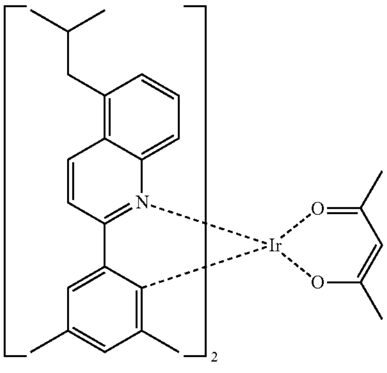
D-39

TABLE 1-continued

| | |
|---|---|
| Electron Transport Layer/Electron Injection Layer | 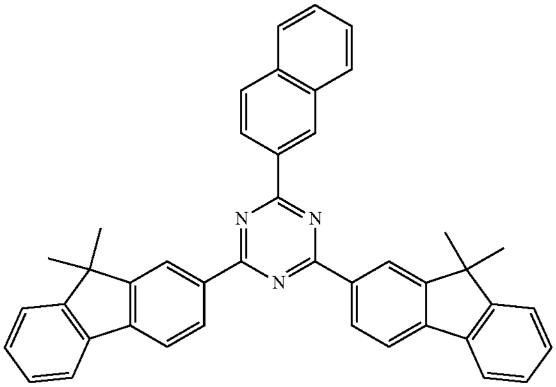 ET-1 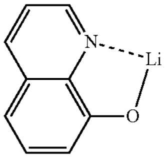 EI-1 |

The invention claimed is:

1. An organic electroluminescent compound represented by the following formula 1-1:

(1-1)

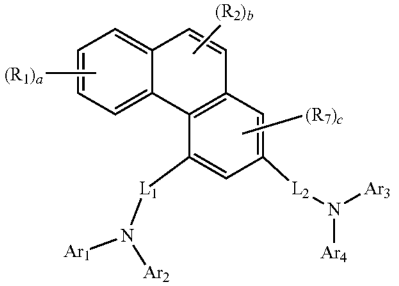

wherein $L_1$ and $L_2$ each independently represents a single bond, a substituted or unsubstituted (C6-C30)arylene or a substituted or unsubstituted (3- to 30-membered)heteroarylene;

$Ar_1$ to $Ar_4$ each independently represent a substituted or unsubstituted (C6-C30)aryl, a substituted or unsubstituted (3- to 30-membered)heteroaryl, or a substituted or unsubstituted fused ring of a (C3-C30)aliphatic ring(s) and a (C6-C30)aromatic ring(s);

$R_1$ and $R_2$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl or $-L_3-N-(Ar_5)(Ar_6)$;

$R_7$ represents hydrogen or deuterium;

$L_3$ each independently represents a single bond, a substituted or unsubstituted (C6-C30)arylene, or a substituted or unsubstituted (3- to 30-membered)heteroarylene;

$Ar_5$ and $Ar_6$ each independently represent a substituted or unsubstituted fused ring of a (C3-C30)aliphatic ring(s) and a (C6-C30)aromatic ring(s), a substituted or unsubstituted (C6-C30)aryl, or a substituted or unsubstituted (3- to 30-membered)heteroaryl;

a is an integer of 1 to 4, b and c are 1 or 2, and when a, b and c are each an integer of 2 or more, each of $R_1$, $R_2$ and $R_7$ may be the same or different from each other; and when there are a plurality of substituents represented by the same symbol, each of the substituents represented by the same symbol may be the same or different from each other.

2. The organic electroluminescent compound according to claim 1, wherein the substituents of the substituted (C1-C30)alkyl, the substituted (C6-C30)aryl, the substituted (C6-C30)arylene, the substituted (3- to 30-membered)heteroaryl, the substituted (3- to 30-membered)heteroarylene and the substituted (C3-C30)cycloalkyl, substituted fused ring of a (C3-C30)aliphatic ring(s) and a (C6-C30)aromatic ring(s)

each independently, are at least one selected from the group consisting of (1)deuterium; a halogen; a cyano; a carboxyl; a nitro; a hydroxyl; a phosphine oxide; a (C1-C30)alkyl; a halo(C1-C30)alkyl; a (C2-C30)alkenyl; a (C2-C30) alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; and a (5- to 50-membered) heteroaryl, each of which is unsubstituted or substituted with at least one of a (C1-C30)alkyl(s), a (C6-C30)aryl(s), or a di(C6-C30)arylamino(s); and (2) a (C6-C30)aryl which is unsubstituted or substituted with at least one of a (C1-C30)alkyl(s), and (3) a (3- to 50-membered)heteroaryl(s), and a mono- or di-(C6-C30)arylamino(s); and (4) a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C2-C30)alkenylamino; and a mono- or di-(C6-C30)arylamino, each of which is unsubstituted or substituted with at least one of a (C1-C30)alkyl(s), a (5- to 30-membered)heteroaryl(s), or a di(C6-C30)arylamino(s); and (5) a mono- or di-(3- to 30-membered)heteroarylamino; a (C1-C30)alkyl(C2-C30)alkenylamino; a (C1-C30)alkyl(C6-C30)arylamino; a (C1-C30)alkyl (3- to 30-membered)heteroarylamino; a (C2-C30) alkenyl(C6-C30)arylamino; a (C2-C30)alkenyl(3- to 30-membered)heteroarylamino; a (C6-C30)aryl(3- to 30-membered)heteroarylamino; a (C1-C30)alkylcarbonyl; a (C1-C30)alkoxycarbonyl; a (C6-C30) arylcarbonyl; a (C6-C30)arylphosphine; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl.

3. The organic electroluminescent compound according to claim 1, wherein $L_1$ and $L_2$ each independently represents a single bond, or a substituted or unsubstituted (C6-C12)arylene;

$Ar_1$ to $Ar_4$ each independently represent a substituted or unsubstituted (C6-C25)aryl, a substituted or unsubstituted (5- to 20-membered)heteroaryl, or a substituted or unsubstituted fused ring of a (C3-C10)aliphatic ring(s) and a (C6-C15)aromatic ring(s);

$R_1$ and $R_2$ each independently represent hydrogen, deuterium, a substituted or unsubstituted (C6-C15)aryl, a substituted or unsubstituted (5- to 15-membered)heteroaryl, or $-L_3-N—(Ar_5)(Ar_6)$;

$R_7$ represents hydrogen or deuterium;

$L_3$ each independently represents a single bond; and $Ar_5$ and $Ar_6$ each independently represent a substituted or unsubstituted (C6-C12)aryl.

4. The organic electroluminescent compound according to claim 1, wherein $L_1$ and $L_2$ each independently represents a single bond, or a substituted or unsubstituted (C6-C12)arylene;

$Ar_1$ to $Ar_4$ each independently represent a (C6-C25)aryl unsubstituted or substituted with at least one of a (C1-C6)alkyl(s) and a (C6-C12)aryl(s); a (5- to 20-membered)heteroaryl unsubstituted or substituted with at least one (C6-C12)aryl(s); or a fused ring of a (C3-C10)aliphatic ring(s) and a (C6-C15)aromatic ring(s) unsubstituted or substituted with at least one (C1-C6)alkyl(s);

$R_1$ and $R_2$ each independently represent hydrogen; a (C6-C15)aryl unsubstituted or substituted with at least one (C1-C6)alkyl(s); a (5- to 15-membered)heteroaryl unsubstituted or substituted with at least one (C6-C12) aryl(s); or $-L_3-N—(Ar_5)(Ar_6)$;

$R_7$ represents hydrogen;

$L_3$ each independently represents a single bond; and $Ar_5$ and $Ar_6$ each independently represent an unsubstituted (C6-C12)aryl.

5. The organic electroluminescent compound according to claim 1, wherein the compound represented by formula 1-1 is selected from the following compounds:

A-1

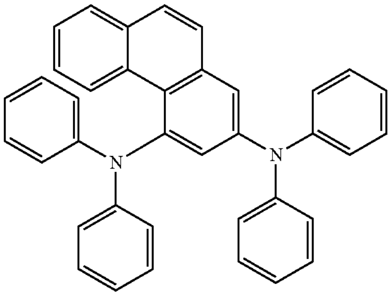

A-2

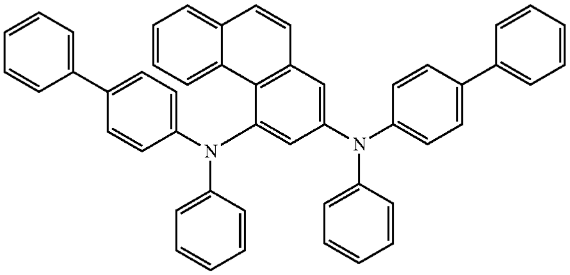

A-3

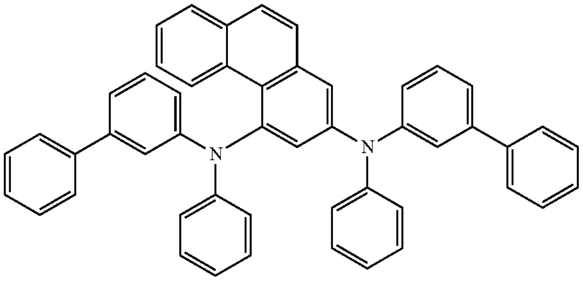

A-4

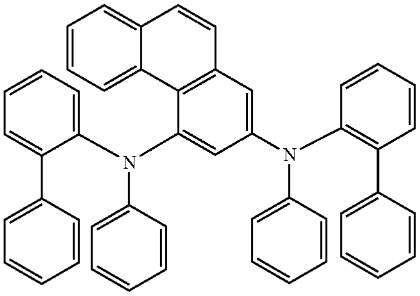

-continued
A-5
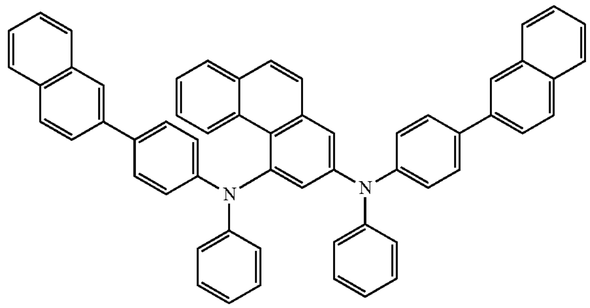
A-6
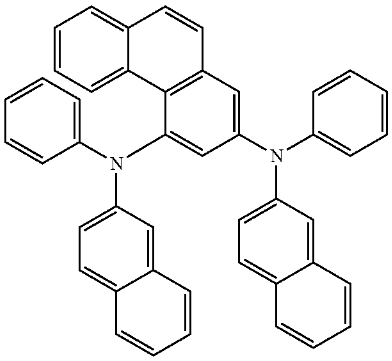
A-7
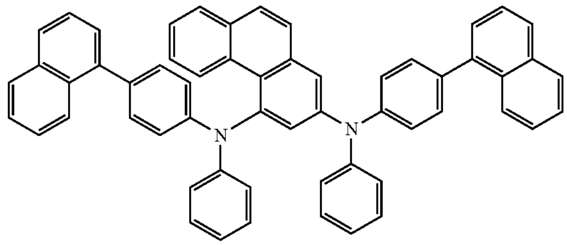
A-8
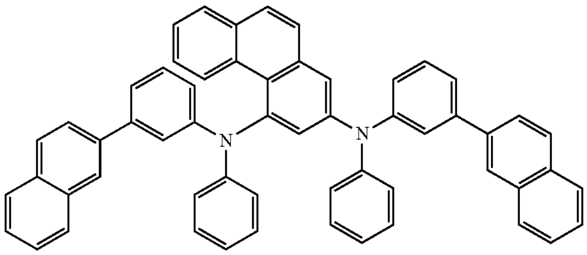
A-9
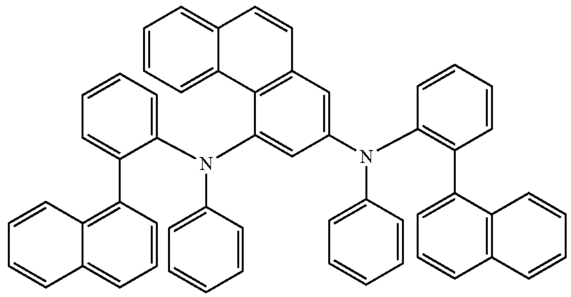
A-10
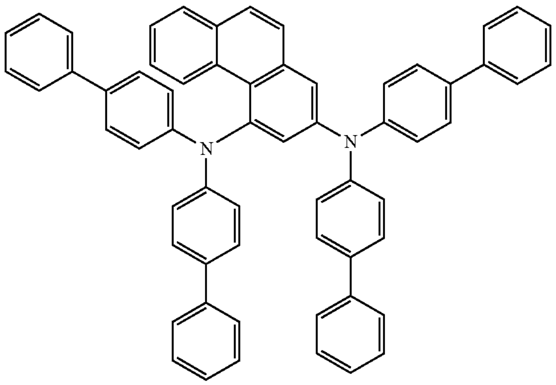
A-11
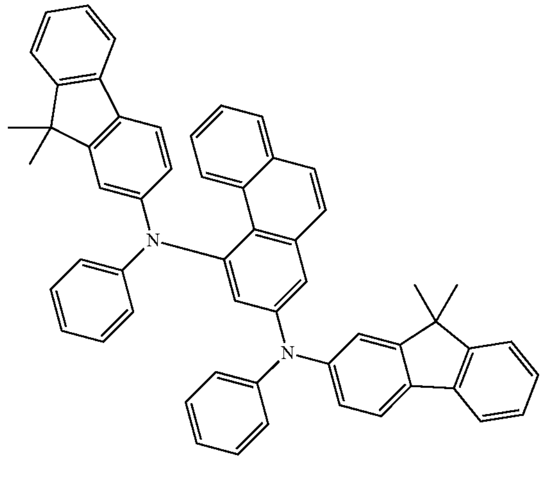

-continued
A-12
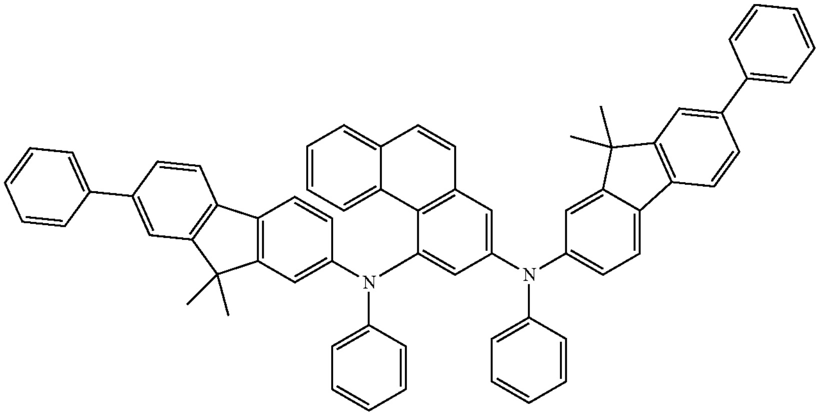
A-13
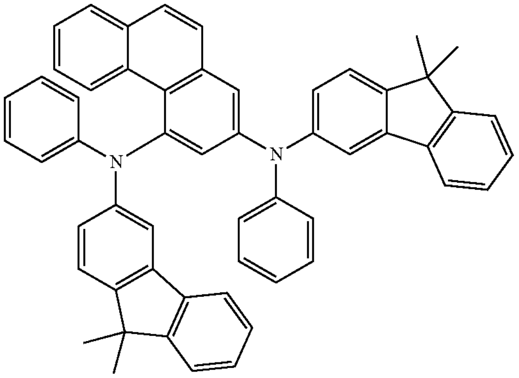
A-14
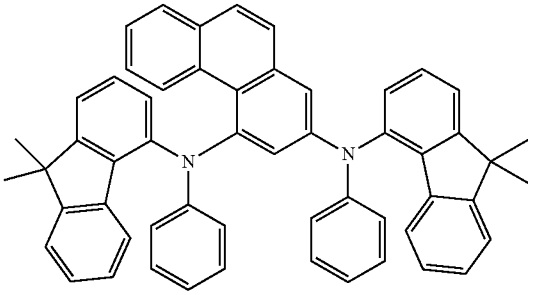
A-15
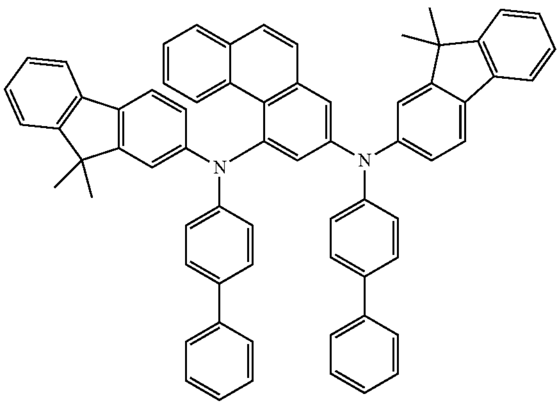
A-16
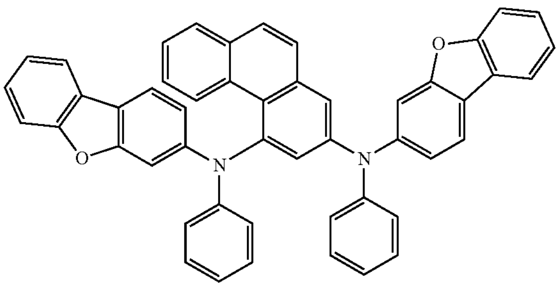
A-17
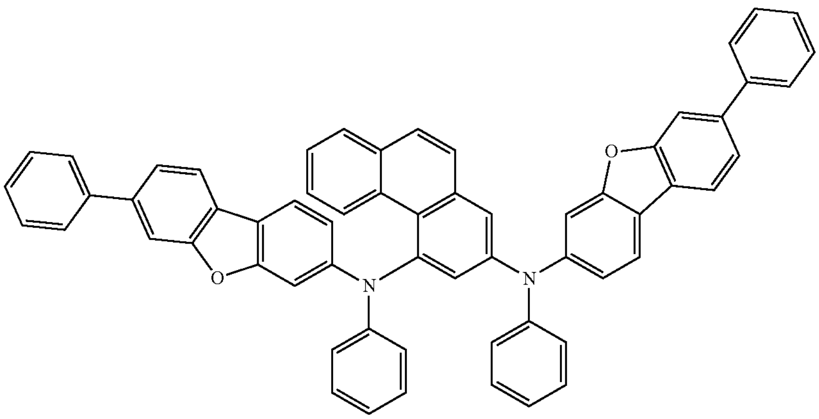

-continued
A-18
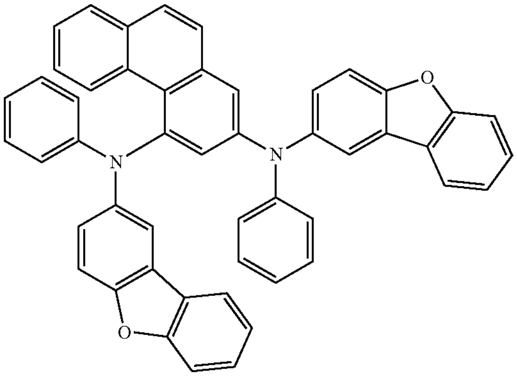
A-19
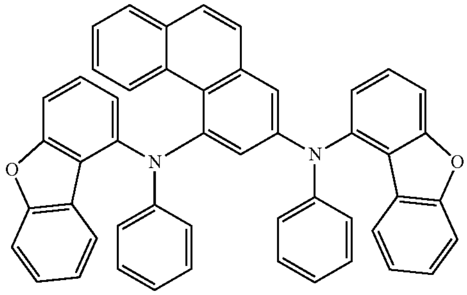
A-20
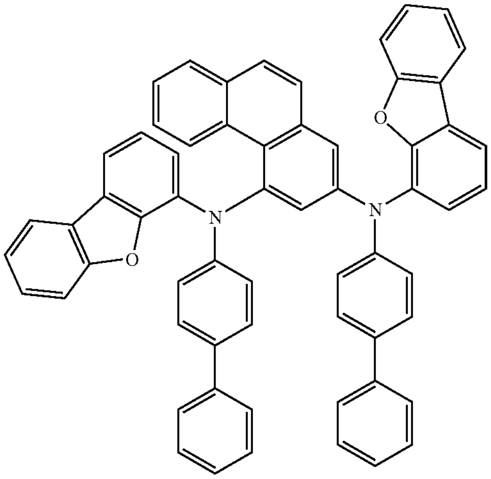
A-21
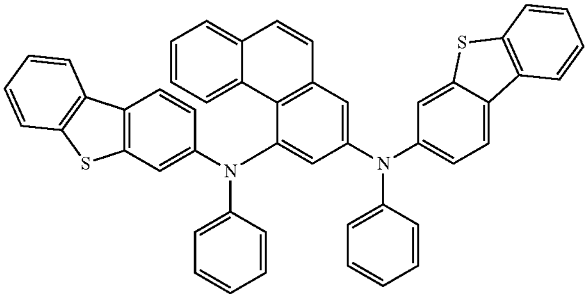
A-22
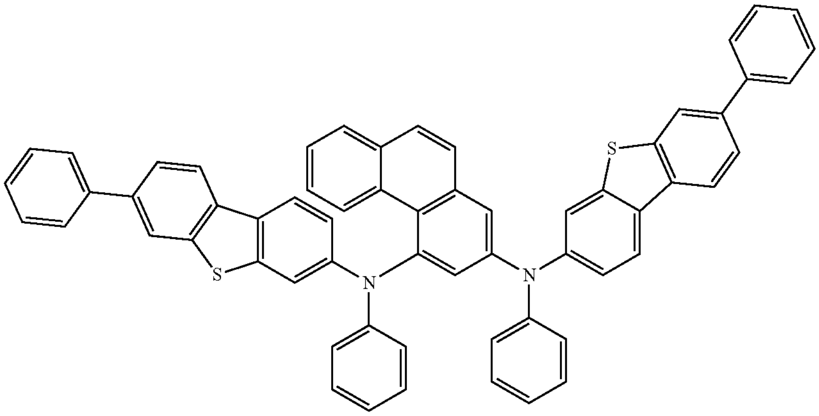

-continued
A-23
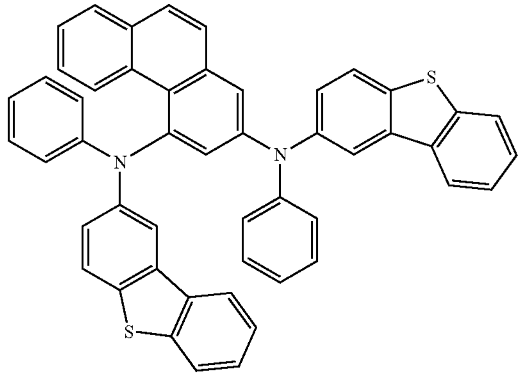
A-24
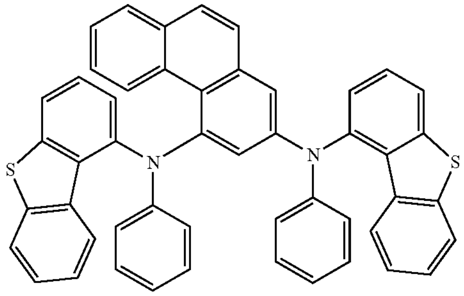
A-25
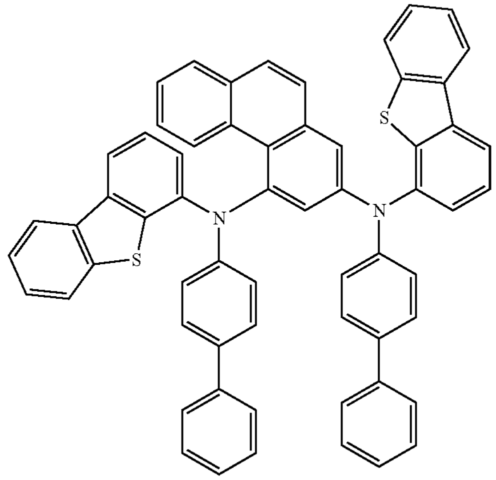
A-26
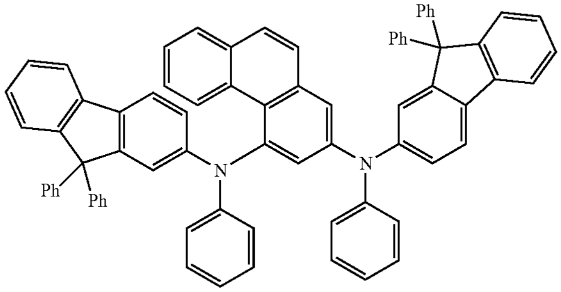
A-27
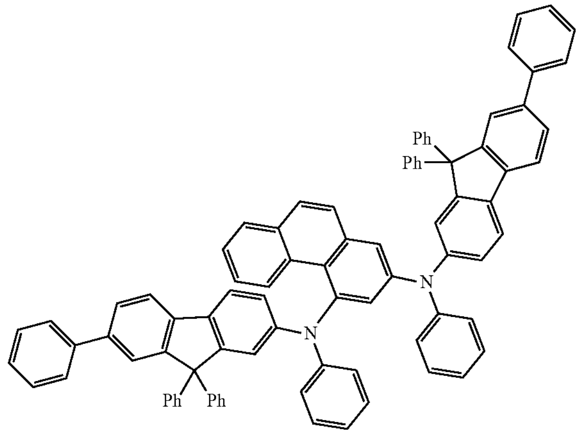
A-28
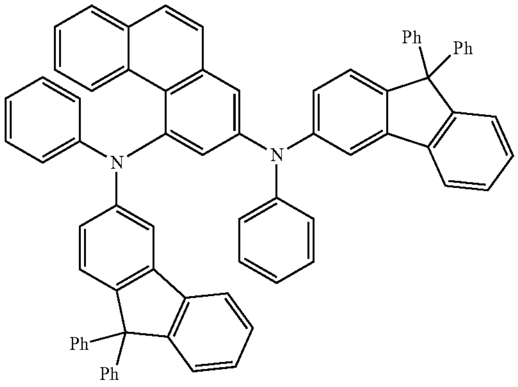

-continued
A-29
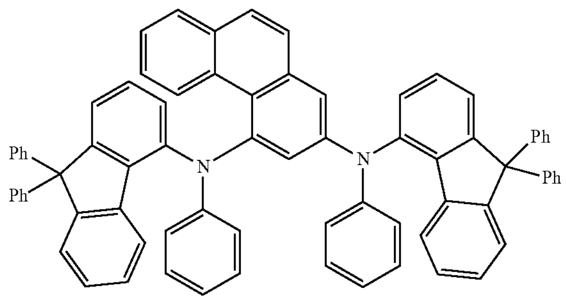
A-30
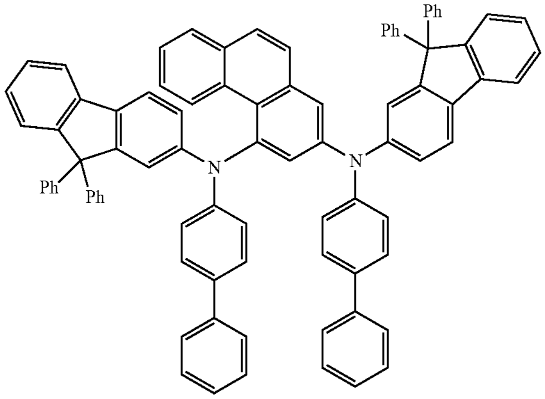
A-31
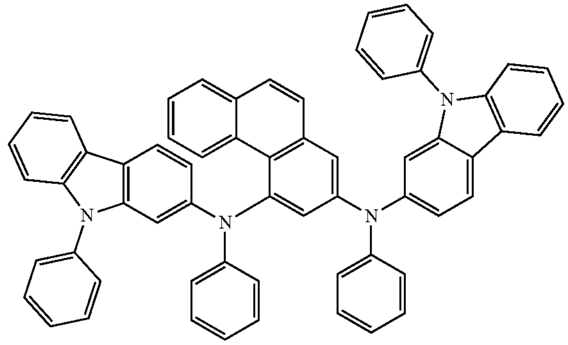
A-32
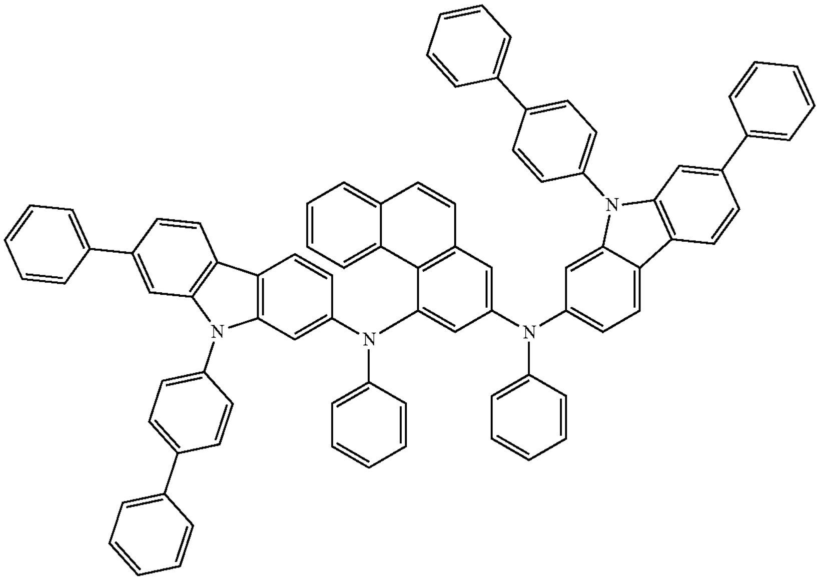

-continued
A-33
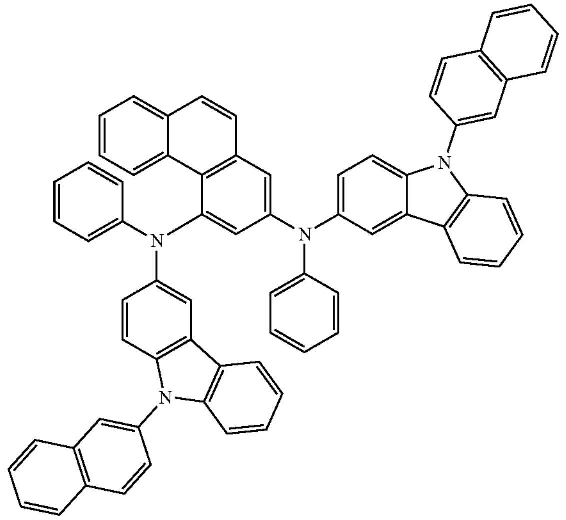
A-34
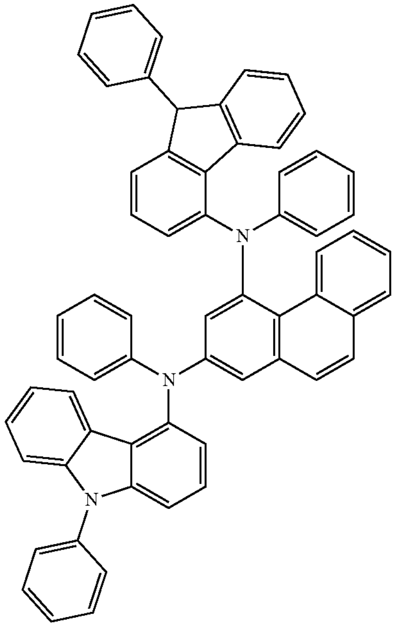
A-35
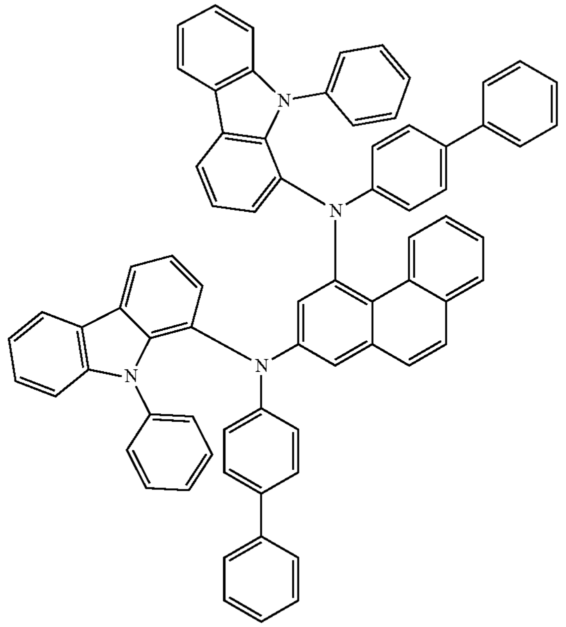
A-36
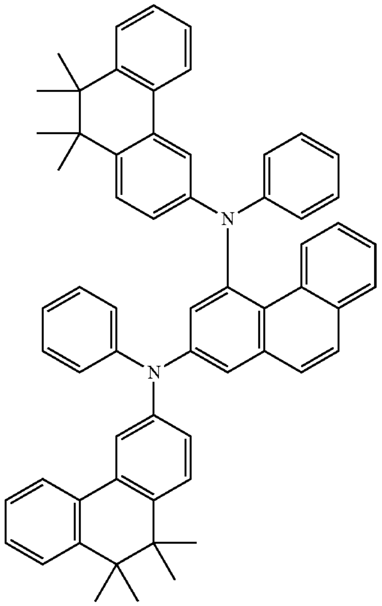
A-37
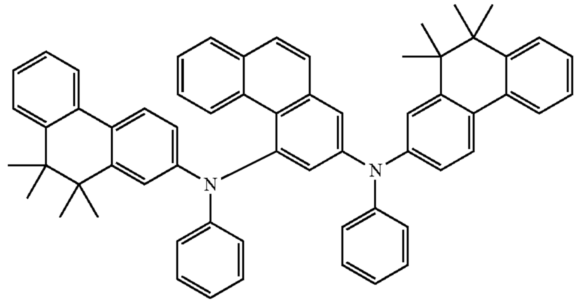
A-38
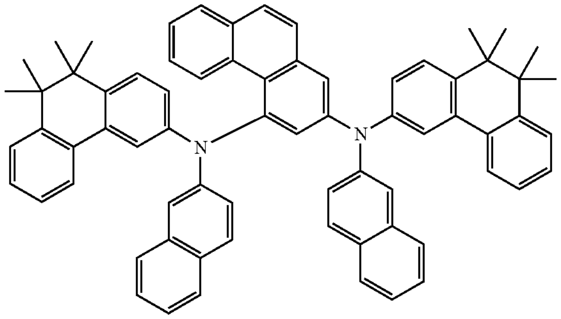

-continued
A-39
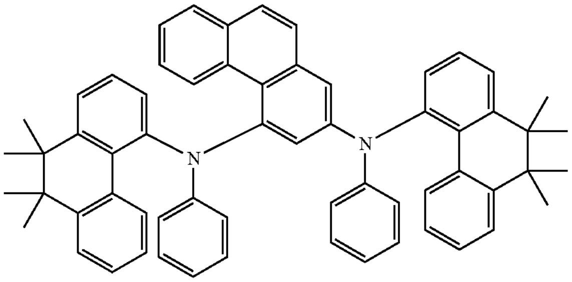
A-40
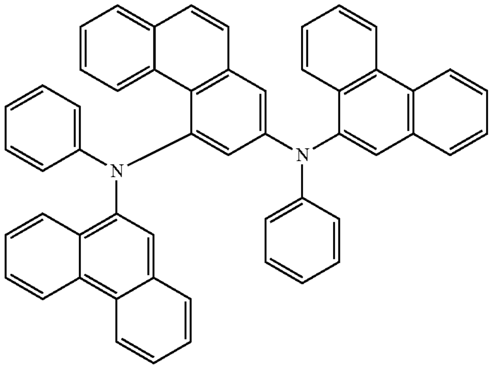
A-41
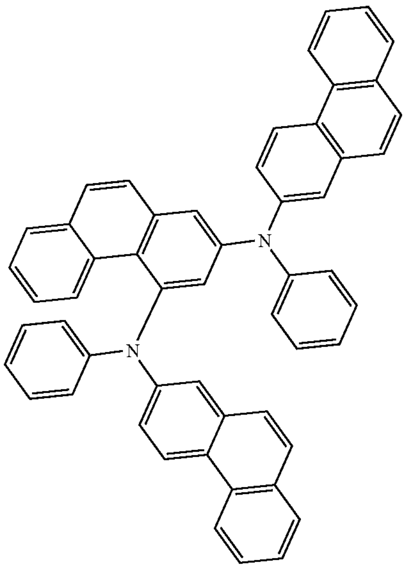
A-42
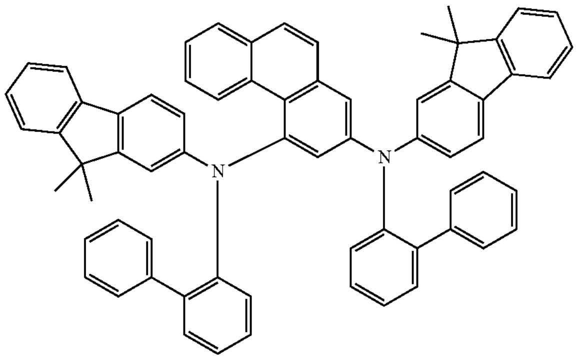
A-43
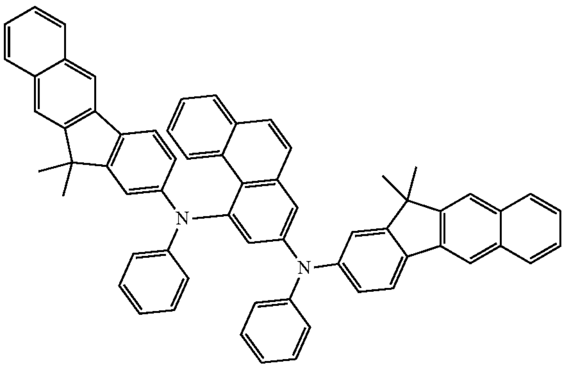
A-44
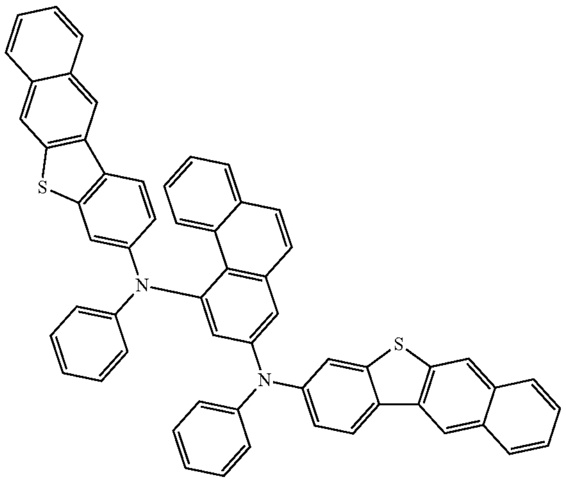

-continued
A-45
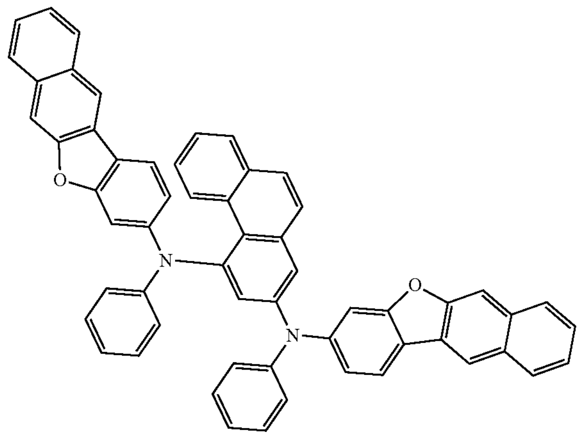
A-46
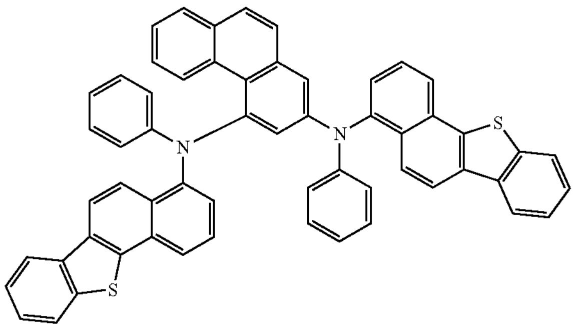
A-47
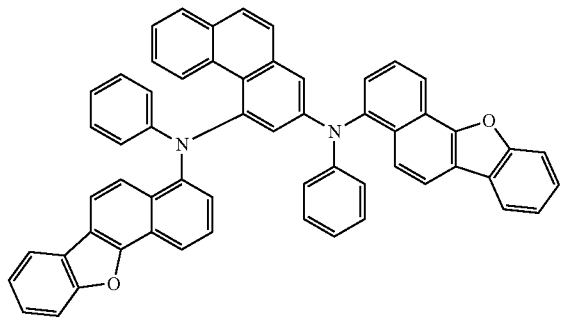
A-48
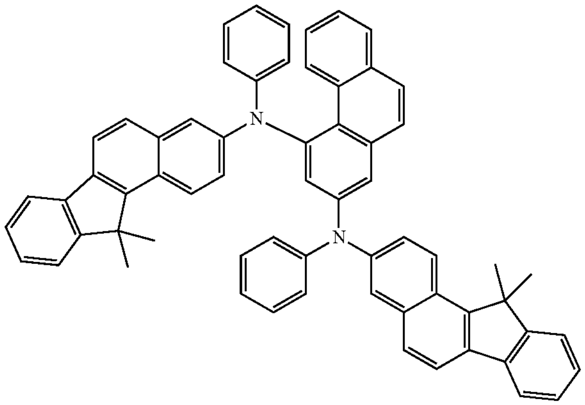
A-49
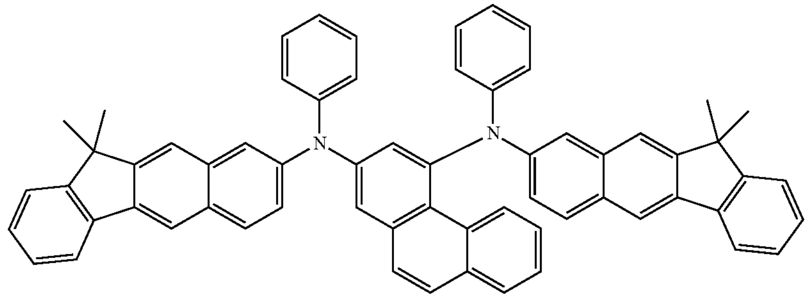
A-99
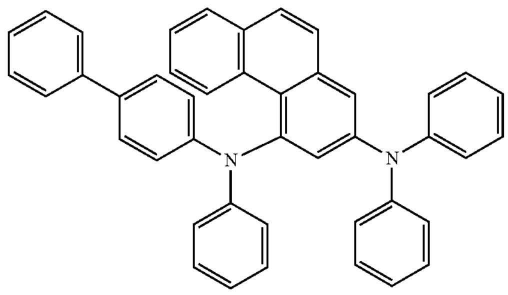
A-100
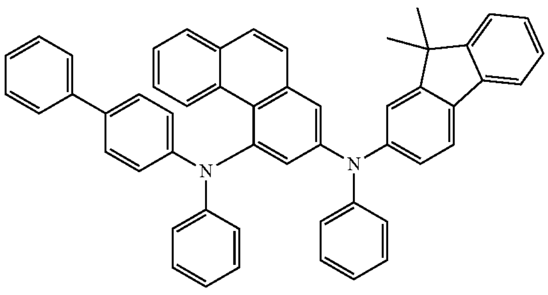

-continued
A-101
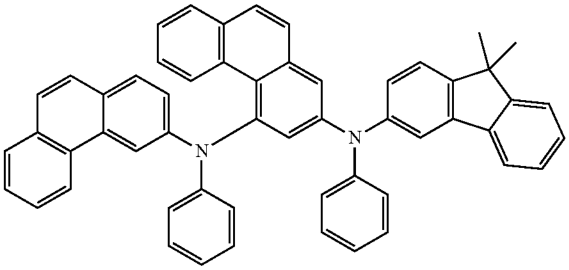
A-102
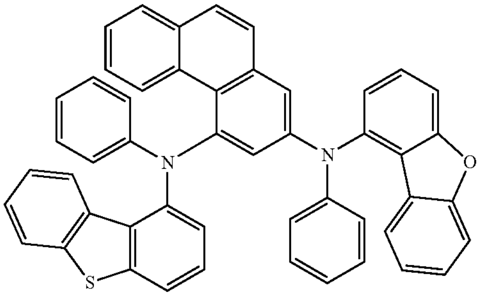
A-103
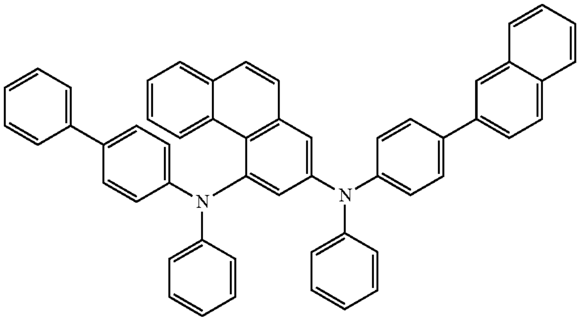
A-104
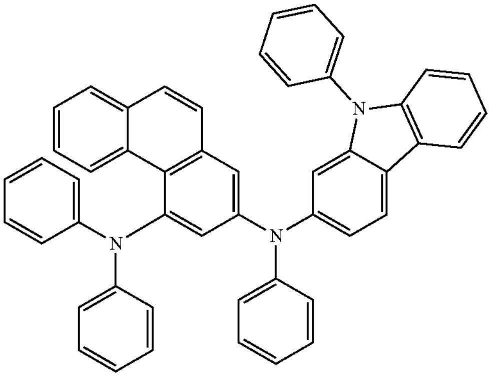
A-105
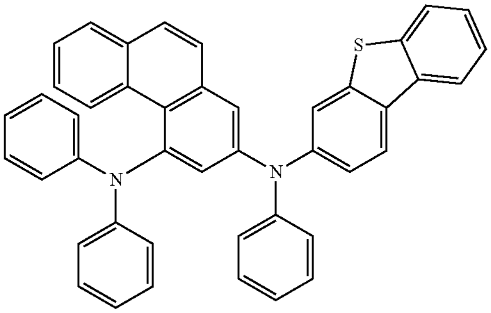
A-106
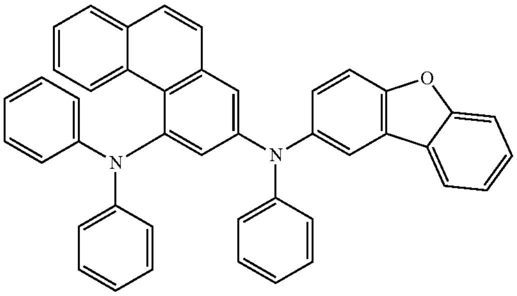
A-107
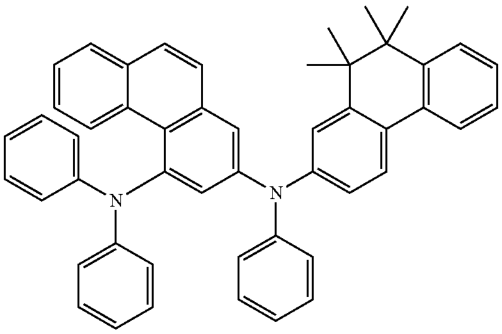
A-108
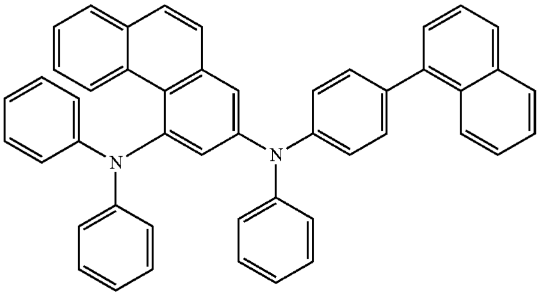

-continued
A-109
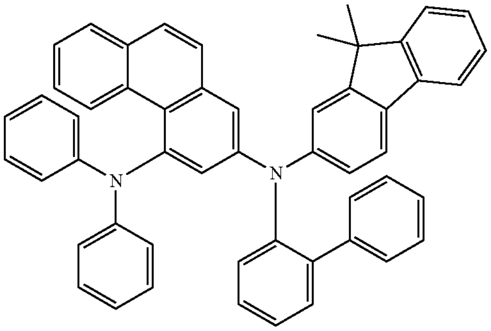
A-110
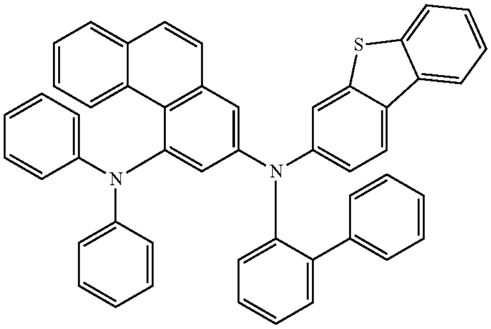
A-111
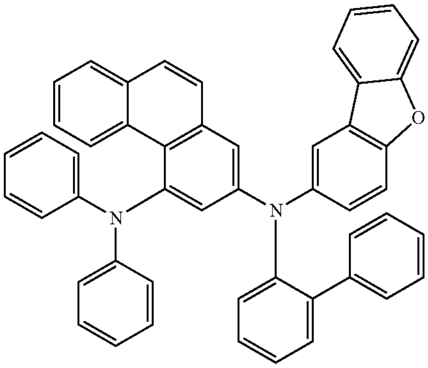
A-112
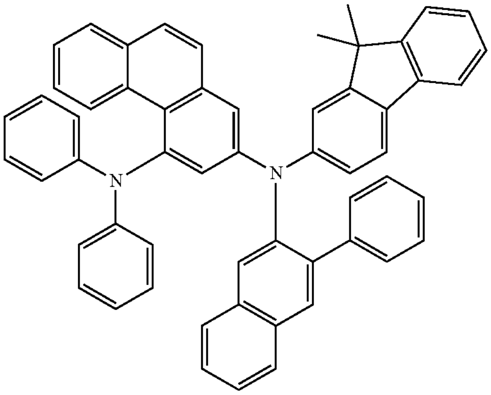
A-113
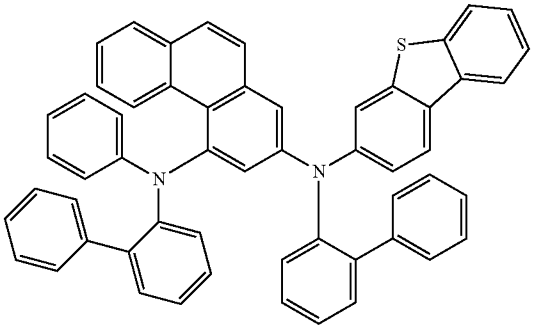
A-114
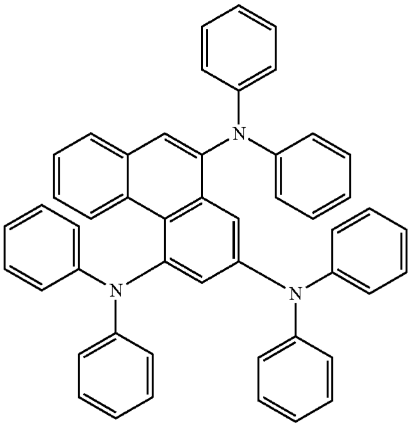
A-115
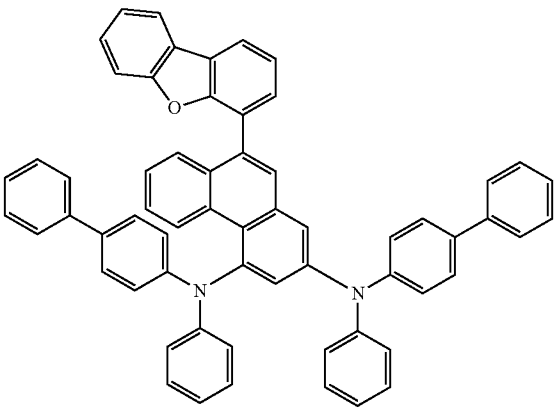
A-116
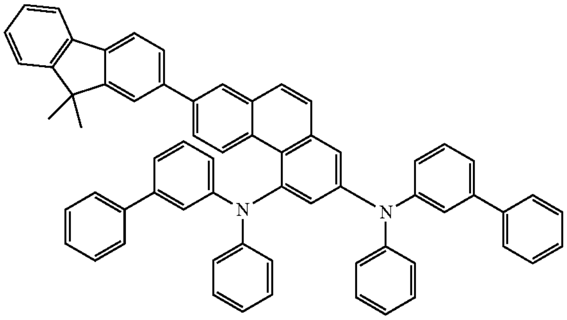

-continued
A-117
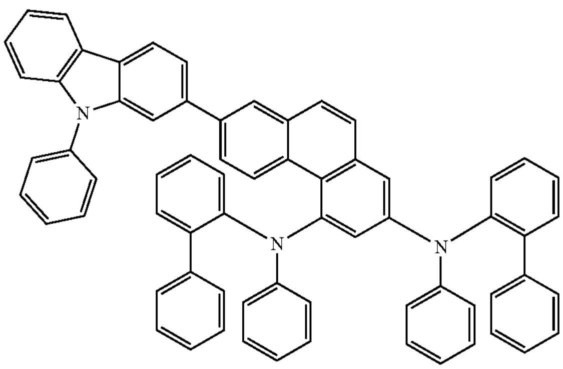
A-118
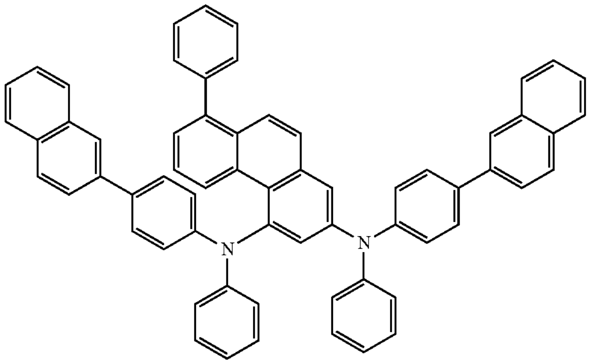
A-130
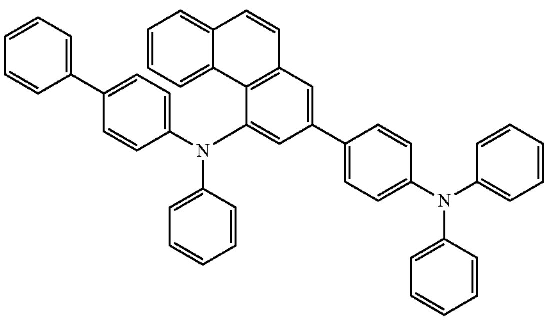
A-131
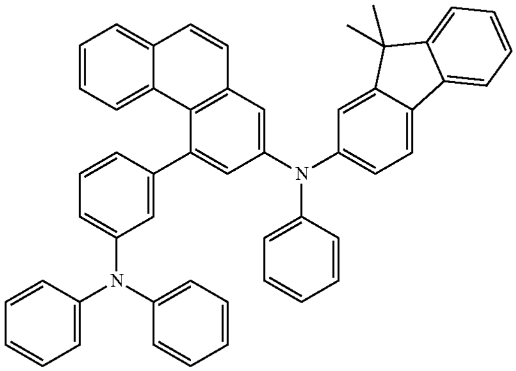
A-132
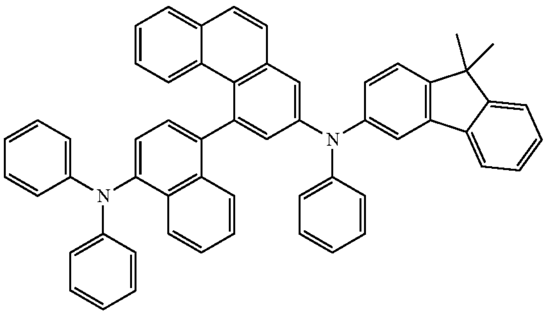
A-133
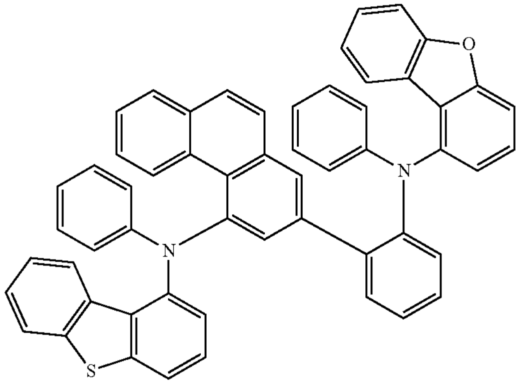
A-134
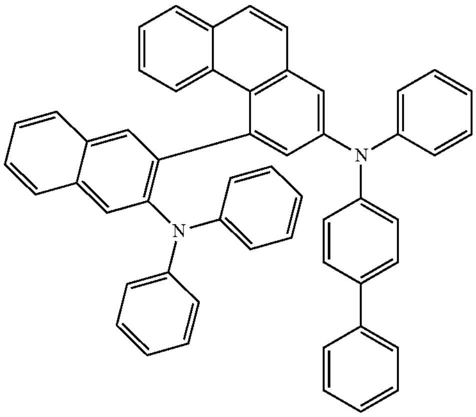
A-135
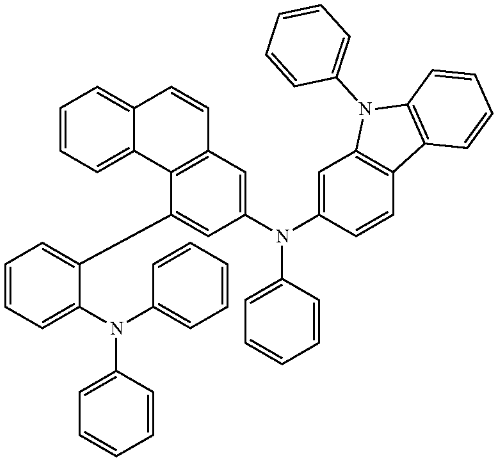

-continued

A-136

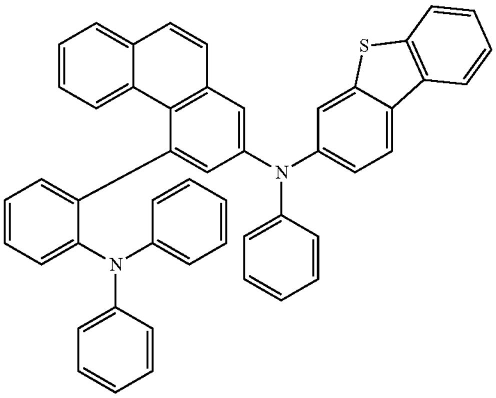

A-137

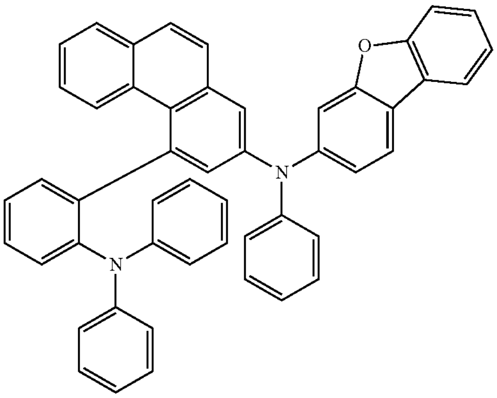

A-138

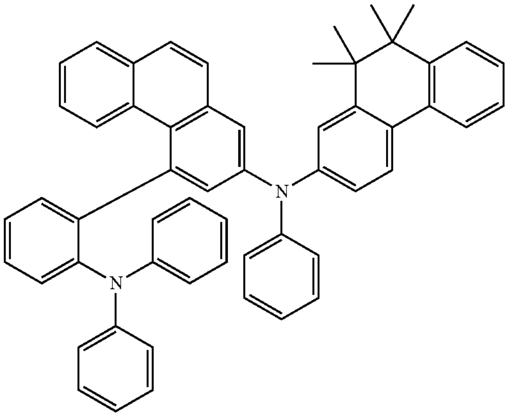

and

A-139

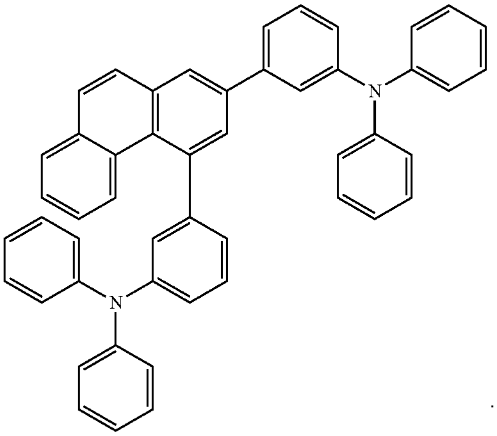

.

6. An organic electroluminescent material comprising the organic electroluminescent compound according to claim 1.

7. An organic electroluminescent device comprising the organic electroluminescent compound according to claim 1.

8. The organic electroluminescent device according to claim 7, wherein the organic electroluminescent compound is comprised in a hole transport zone.

* * * * *